United States Patent [19]

Banno et al.

[11] Patent Number: 4,567,187

[45] Date of Patent: Jan. 28, 1986

[54] CARBOSTYRIL DERIVATIVES AND ANTIHISTAMINIC AGENTS CONTAINING THE CARBOSTYRIL DERIVATIVES

[75] Inventors: Kazuo Banno; Takafumi Fujioka; Masaaki Osaki; Kazuyuki Nakagawa, all of Tokushima, Japan

[73] Assignee: Otsuka Pharmaceutical Co., Ltd., Japan

[21] Appl. No.: 366,336

[22] Filed: Apr. 7, 1982

Related U.S. Application Data

[62] Division of Ser. No. 240,306, Mar. 4, 1981, abandoned.

[30] Foreign Application Priority Data

Mar. 6, 1980 [JP] Japan ................................. 55-28805
Aug. 20, 1980 [JP] Japan ................................. 55-115022

[51] Int. Cl.⁴ ..................... A61K 31/47; C07D 215/22
[52] U.S. Cl. .................................. 514/312; 546/157; 546/158
[58] Field of Search .................. 546/157, 158; 424/258

[56] References Cited

U.S. PATENT DOCUMENTS

| | | | |
|---|---|---|---|
| 3,629,266 | 12/1971 | Havera | 546/158 |
| 3,994,901 | 11/1976 | Nakagawa et al. | 424/258 X |
| 4,022,776 | 5/1977 | Nakagawa et al. | 546/157 X |
| 4,022,784 | 5/1977 | Nakagawa et al. | 424/258 X |
| 4,026,897 | 5/1977 | Nakagawa et al. | 546/157 |
| 4,068,076 | 1/1978 | Nakagawa et al. | 544/128 |
| 4,223,137 | 9/1980 | Yoshizaki et al. | 544/128 |

FOREIGN PATENT DOCUMENTS

| | | |
|---|---|---|
| 0118771 | 10/1976 | Japan . |
| 0118772 | 10/1976 | Japan . |
| 0016478 | 2/1979 | Japan ................................. 546/158 |
| 0083749 | 6/1980 | Japan ................................. 424/258 |

OTHER PUBLICATIONS

Schmidle, et al., J. Am. Chem. Soc., vol. 78, pp. 1702-1705 (1956).
Ariëns, et al., Arch. Int. Pharmacodyn., vol. 110, Nos. 2-3, pp. 275-299 (1957).
van Rossum, Arch. Int. Pharmacodyn., vol. 143, Nos. 3-4, pp. 299-330 (1963).

Primary Examiner—Donald G. Daus
Assistant Examiner—Diana G. Rivers
Attorney, Agent, or Firm—Finnegan, Henderson, Farabow, Garrett & Dunner

[57] ABSTRACT

Novel carbostyril derivatives and their salts having antihistaminic effect and central nervous system controlling effect and are useful as antihistaminic agents and central nervous system controlling agents, represented by the general formula (1),

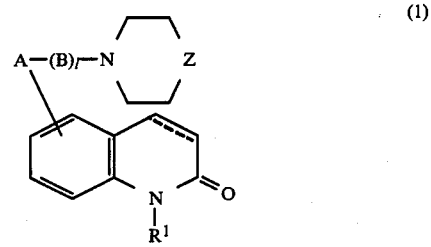

wherein $R^1$ is a hydrogen atom, a lower alkyl group, a phenyl-lower alkyl group, a lower alkenyl group, a lower alkynyl group; A is a group of the formula

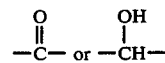

or a group of the formula

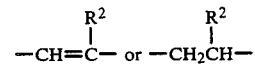

(wherein $R^2$ is a hydrogen atom or a lower alkyl group); B is a lower alkylene group; l is 1 when A is a group of the formula

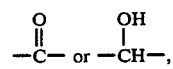

or l is 0 or 1 when A is a group of the formula

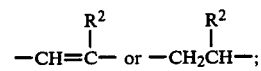

Z is a group of the formula

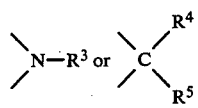

(wherein $R^3$ is a substituted-phenyl group having 1 to 3 substituents, on the phenyl ring, selected from the group consisting of a halogen atom, a lower alkyl group, a lower alkoxy group, a lower alkoxy-carbonyl group, a carboxyl group, a lower alkylthio group, a lower alkanoyl group, a hydroxyl group, a nitro group, an amino group and a cyano group; or $R^3$ is a substituted-phenyl group having a lower alkylenedioxy group as the substituent, a phenyl-lower alkyl group or a 1,2,3,4-tetrahydronaphthyl group; $R^4$ is a substituted-phenyl group having 1 to 3 substituents, on the phenyl group, selected from the group consisting of a halogen atom, a lower alkyl group and a lower alkoxy group; or $R^4$ is a substituted-phenyl group having a lower alkylenedioxy (Abstract continued on next page.)

group as the substituent, a phenyl-lower alkyl group, a 1,2,3,4-tetrahydronaphthyl group or a group of the formula

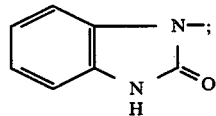

$R^5$ is a hydrogen atom, a hydroxyl group or a lower alkanoyl group; or when $R^5$ is a hydrogen atom the carbon-carbon bond between 3- and 4-positions in the piperidine ring is a double bond which is dehydrogenated the hydrogen atoms bonded at 3- and 4-positions of piperidine ring; the carbon-carbon bond between 3- and 4-positions in the carbostyril skeleton is a single or double bond.

The carbostyril derivatives of the present invention have antihistaminic effects and central nervous system controlling effects and are useful for antihistaminic agents and central nervous system controlling agents.

21 Claims, No Drawings

CARBOSTYRIL DERIVATIVES AND ANTIHISTAMINIC AGENTS CONTAINING THE CARBOSTYRIL DERIVATIVES

This is a division of application Ser. No. 240,306, filed Mar. 4, 1981, now abandoned.

The present invention relates to novel carbostyril derivatives. More particularly, the present invention relates to novel carbostyril derivatives and their salts represented by the general formula (1) as follows:

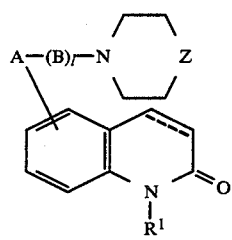

(1)

wherein $R^1$ is a hydrogen atom, a lower alkyl group, a phenyl-lower alkyl group, a lower alkenyl group, a lower alkynyl group; A is a group of the formula

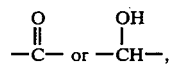

or a group of the formula

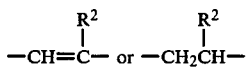

(wherein $R^2$ is a hydrogen atom or a lower alkyl group); B is a lower alkylene group; l is 1 when A is a group of the formula

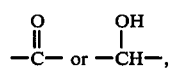

or l is 0 or 1 when A is a group of the formula

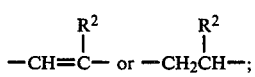

Z is a group of the formula

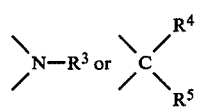

(wherein $R^3$ is an unsubstituted or is a substituted-phenyl group having 1 to 3 substituents, on the phenyl group, selected from the group consisting of a halogen atom, a lower alkyl group, a lower alkoxy group, a lower alkoxy-carbonyl group, a carboxyl group, a lower alkylthio group, a lower alkanoyl group, a hydroxyl group, a nitro group, an amino group and a cyano group; or $R^3$ is a substituted-phenyl group having a lower alkylenedioxy group as the substituent on the phenyl group, a phenyl-lower alkyl group or a tetralinyl group (i.e., a 1,2,3,4-tetrahydronaphthyl group); $R^4$ is an unsubstituted or a substituted-phenyl group having 1 to 3 substituents, on the phenyl group, selected from the group consisting of a halogen atom, a lower alkyl group and a lower alkyl group and a lower alkoxy group; $R^4$ is a substituted-phenyl group having a lower alkylenedioxy group as the substituent on the phenyl group, a phenyl-lower alkyl group, a 1,2,3,4-tetrahydronaphthyl group or a group of the formula

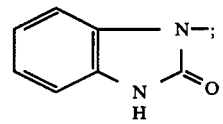

$R^5$ is a hydrogen atom, a hydroxyl group or a lower alkanoyl group; or when $R^5$ is a hydrogen atom, the carbon-carbon bond between 3- and 4-positions in the piperidine ring is a double bond which is dehydrogenated the hydrogen atoms bonded at 3- and 4-positions in the piperidine ring); the carbon-carbon bond between 3- and 4-positions in the carbostyril skeleton is a single or double bond.

The carbostyril derivatives of the present invention have antihistaminic effects and central nervous system controlling effects, and are useful for antihistaminic agents and central nervous system controlling agents.

The carbostyril derivatives of the present invention have strong controlling activities for fighting motion of mouse being singly isolated from others for a long period of time. Thus as compared with Diazepam, which has been known as a compound having strong such activities, compounds of the present invention have outstanding controlling effect for fighting motion of mouse, therefore the present compounds are quite useful, particularly, as sedatives, antianxiety drugs, antimanic depressive psychosis drug. Furthermore, compounds of the present invention have strong effects for increasing anesthesia and sleep when they are used in combination with anesthetics and hypnotics. Compound of the present invention are also useful for pre-anesthetics and sleep-inducing agents in addition to above-mentioned strong controlling effect for fighting motion of mouse.

Furthermore, as to the central nervous system controlling activities, compounds of the present invention have various pharmacological activities such as muscle relaxizating action, ptosis action, hypothermy action, spontaneous movement controlling action, hypermotion controlling action of rat whose olfactory bulb is enucleated (OB-rat), anti-methanphetamine action, methanphetamine group toxicities lowering action, analgetic action and anti-epinephrine action, but they have only weak activities in anti-choline action, cardio-inhibitory action and catalepsy inducing action. Therefore, compounds of the present invention are useful for central nervous system controlling agents such as central muscle relaxizating agents, sleep-inducing agents, pre-operative drugs, anti-schizophrenia agents, sedatives, antianxiety drugs, antimanic depressive psychosis agents, antipyretic agents, analgetic agents and depressors, without showing side-effects such as thirst feeling, constipation, tachycordia, parkinsonism, and/or delayed dyscinesia which are showed by conventional central nervous system controlling agents.

The compounds of the present invention also have antihistaminic effects with the following features and are useful for antihistaminic agents.

As there are described in various articles of medical and pharmaceutical publications, for example, Goodman-Gilman's: "Pharmacology" (the first volume), "YAKUBUTSU CHIRYO NO KISO TO RINSHO" (Fundamental and Clinic of Pharmacotherapy), pages 781–835 [published from Hirokawa Shoten Co., (1974)]; "SHIN-OYO YAKURIGAKU" (New Applied Pharmacology) by Hisashi Uno, pages 307 to 319 [published from Nagai Shoten Co., (1970)] "SHIN-YAKU TO RINSHO" (Journal of New Remedies & Clinic), Vol. 20, No. 11, pages 129–133 (1971); and "KISO TO RINSHO" (Laboratory and Clinic), Vol. 10, No. 10, pages 17–27 (1976), that generally an antihistaminic agent does not inhibit the isolation of combined type histamine formed by the antigen-antibody reaction in allergies, but does inhibits the combination (a competitive antagonism) of an active type histamine with a histamine-acceptor to show antihistaminic effect. The antihistaminic agents of the present invention are, therefore, effective as treating agents and prophylactic agents for various allergic diseases and symptoms caused by the combination of histamine and histamine-acceptor, for example allergic symptoms in respiratory tract, such as sneezing, sniffles, prickling at eyes, nose and throat, hay fever, pollinosis, acute uriticaria (itching, edama, flare and the like), vascular edema, pruritus, atopic dermatitis, insect bite, contact-type dermatitis such as "urushi kabure" (ivy poisoning), urticaria and edemic disorder in serum disease, allergic rhinitis, allergic cunjuctivitis or corneitis. Furthermore, an antihistaminic agents of the present invention can also be used as supplemental agents for curing systemic anaphylaxis in which autacoids other than histamine may perform as important role. Additionally the carbostyril derivatives of the present invention can also be used as diagnostic reagents for measuring the activity of excretion of gastric juice.

Some carbostyril derivatives having useful pharmacological effects, such as antiinflammatory effect, inhibitory effect on blood platelet aggregation, central nervous system controlling effect and $\beta$-adrenergic nerve blocking effect are known in prior art literatures, for example U.S. Pat. Nos. 3,994,900, 4,147,869; DOS Nos. 2302027, 2711719; Japanese Patent Application Kokai (Laid-open) Nos. 106977/1975, 142576/1975. However, these prior art literatures do not disclose that these carbostyril derivatives have antihistaminic effects.

On the other hand, other carbostyril derivatives having antihistaminic effects are known in other prior art literatures, for example, DOS No. 2912105, Japanese Patent Application Kokai (Laid-open) Nos. 16478/1979, 2693/1980, 89221/1980, 89222/1980. However, these carbostyril derivatives having antihistaminic effects known in the art are different from the carbostyril derivatives of the present invention respect to the type and the substituted positions of the substituted groups.

Furthermore, European Patent Application No. 5828 discloses a phenylpiperazino-propoxy-indoline or quinoline derivative which is useful as psychotropic and cardiovascular agent. European Patent Application No. 6506 discloses piperazinyl-alkoxy quinoline derivative which is useful as anti-allergic agent. However, these prior art derivatives are again different from the carbostyril derivatives of the present invention with respect to the type of the substituted side chain groups.

In these carbostyril derivatives known in the prior art, the main side chains are bonded to the benzene ring of the carbostyril skeleton through oxygen linkage (—O—), whereas, in compounds of the present invention, the side chains are bonded to 5- to 8-positions of the carbostyril skeleton through a group of the formula

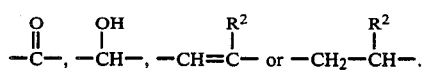

On the other hand, some carbostyril derivatives having useful pharmacological effects are known in other prior art literatures, for example Japanese Patent Application Kokai (Laid-open) No. 118771/1976, 118772/1976, 9777/1978 and Japanese Patent Publication No. 12515/1978, 12516/1978 and 16478/1979. The linkage between the side chain and the carbostyril skeleton in these carbostyril derivatives of the above-mentioned prior art literature are similar to those of the compounds of the present invention. However, again, such prior art derivatives are different from compounds of the present invention with respect to the type of the substituted side chain groups.

Among the compounds of the general formula (1) of the present invention, compounds having a group of the formula

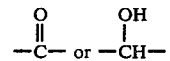

as for the definition of "A" can easily be metabolized in vivo with relatively lower side-effects against the lever and perform as short time-active type central nervous system controlling agents and antihistaminic agents. Among such compounds, compounds having a group of the formula N—$R^3$ as for the definition of "Z" are useful as sleep-inducing agents and pre-operative drugs.

Among the compounds of the general formula (1), compounds having a group of the formula

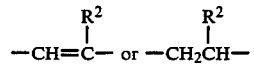

as for the definition of "A" and having a group of the formula >N—$R^3$ as for the definition of "Z" have strong central nervous system controlling activities for long period of time with relatively low toxicities. Furthermore, such compounds also have anti-dopamine effect as well as anti-epinephrine effect and are particularly useful as treating agents for schizophrenia and analgetic agents.

Among the compounds of the general formula (1); compounds having a group of the formula

as for the definition of "Z" have weak central nervous system controlling activities, but have antihistaminic effects selectively and are specifically useful as antihistaminic agents.

In the present specification, the specific examples of the groups defined in the respective symbols of A, B, $R^1$, $R^2$, $R^4$ and $R^5$ are shown below.

The term "a lower akoxycarbonyl group" means an alkoxycarbonyl group in which the alkyl group is a straight or branched chain having 1 to 6 carbon atoms, and the examples including methoxycarbonyl, ethoxycarbonyl, propoxycarbonyl, isopropoxycarbonyl, butoxycarbonyl, tert-butoxycarbonyl, pentyloxycarbonyl and hexyloxycarbonyl groups and the like.

The term "a lower alkylenedioxy group" means an alkylenedioxy group in which the alkylene group is a straight or branched chain having 1 to 4 carbon atoms, and the examples including methylenedioxy, ethylenedioxy, trimethylenedioxy and tetramethylenedioxy groups and the like.

The term "a lower alkylthio" group means an alkylthio group in which the alkyl group is a straight or branched chain having 1 to 6 carbon atoms, and the examples including methylthio, ethylthio, propylthio, iso-propylthio, butylthio, tert-butylthio, pentylthio and hexylthio groups and the like.

The term "a lower alkyl group" means a straight or branched alkyl group having 1 to 6 carbon atoms, and the examples including methyl, ethyl, propyl, isopropyl, butyl, tert-butyl, pentyl and hexyl groups and the like.

The term "a phenyl-lower alkyl group" means a phenyl-alkyl group in which the alkylene group is a straight or branched chain having 1 to 6 carbon atoms, and the examples including benzyl, 2-phenylethyl, 1-phenylethyl, 8-phenylpropyl, 4-phenylbutyl, 1,1-dimethyl-2-phenylethyl, 5-phenylpentyl, 6-phenylhexyl and 2-methyl-3-phenylpropyl groups and the like.

The term "a lower alkenyl group" means a straight or branched alkenyl group having 2 to 6 carbon atoms, and the examples including vinyl, allyl, 2-butenyl, 3-butenyl, 1-methylallyl, 2-pentenyl and 2-hexenyl groups and the like.

The term "a lower alkynyl group" means a straight or branched alkynyl group having 2 to 6 carbon atoms, the examples including ethynyl, 2-propynyl, 2-butynyl, 3-butynyl, 1-methyl-2-propynyl, 2-pentynyl and 2-hexynyl groups and the like.

The term "halogen atom" means fluorine, chlorine, bromine and iodine atoms.

The term "a lower alkoxy group" means an alkoxy group in which the alkyl group is a straight or branched chain having 1 to 6 carbon atoms, and the examples including methoxy, ethoxy, propoxy, isopropoxy, butoxy, tertbutoxy, pentyloxy and hexyloxy groups and the like.

The term "a lower alkanoyl group" means a straight or branched alkanoyl group having 1 to 6 carbon atoms, and the examples including formyl, acetyl, propionyl, butyryl, isobutyryl, pentanoyl, tert-butylcarbonyl and hexanoyl groups and the like.

The term "a lower alkylene group" means a straight or branched alkylene group having 1 to 6 carbon atoms, and the examples including methylene, ethylene, trimethylene, 2-methyltrimethylene, 2,2-dimethyltrimethylene, 1-methyltrimethylene, methylmethylene, ethylmethylene, tetramethylene, pentamethylene, and hexamethyene groups and the like.

The term "a substituted-phenyl group having 1 to 3 substituents, on the phenyl ring, selected from the group consisting of a halogen atom, a lower alkyl group, a lower alkoxy group; or a substituted-phenyl group having lower alkylenedioxy group as the substituent" means a substituted-phenyl group having 1 to 3 substituents, on the phenyl ring, selected from the group consisting of a halogen atom, an alkyl group having 1 to 6 carbon atoms, an alkoxy group having 1 to 6 carbon atoms, or a substituted-phenyl group having 1 to 4 alkylenedioxy groups, on the phenyl ring, and the examples including phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 4-iodophenyl, 3,4-methylenedioxyphenyl, 3,4-ethylenedioxyphenyl, 3,4-trimethylenedioxyphenyl, 2,3-methylenedioxyphenyl, 3,5-dichlorophenyl, 2,6-dichlorophenyl, 3,4-dichlorophenyl, 3,4-difluorophenyl, 3,5-dibromophenyl, 3,4,5-trichlorophenyl, 2-methylphenyl, 3-methylphenyl, 4-methylphenyl, 2-ethylphenyl, 3-ethylphenyl, 4-ethylphenyl, 3-isopropylphenyl, 4-hexylphenyl, 3,4-dimethylphenyl, 2,5-dimethylphenyl, 3,4,5-trimethylphenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-hexyloxyphenyl, 3,4-dimethoxyphenyl, 3,4-diethoxyphenyl, 3,4,5-trimethoxyphenyl and 2,5-dimethoxyphenyl grounds and the like.

The term "a substituted-phenyl group having 1 to 3 substituents, on the phenyl ring, selected from the group consisting of a halogen atom, a lower alkyl group, a lower alkoxy group, a lower alkoxy-carbonyl group, carboxyl group, a lower alkylthio group, a lower alkanoyl group, a hydroxyl group, a nitro group, an amino group and a cyano group; or a substituted-phenyl group havng a lower alkylenedioxy group as the substituent on the phenyl group" means a substituted-phenyl group having 1 to 3 substituents, on the phenyl ring, selected from the group consisting of a halogen atom a lower alkyl group having 1 to 6 carbon atoms, a lower alkoxy group having 1 to 6 carbon atoms, a lower alkoxy-carbonyl group having 1 to 6 carbon atoms, a carboxyl group, a lower alkylthio group having 1 to 6 carbon atoms, a lower alkanoyl group having 1 to 6 carbon atoms, a hydroxyl group, a nitro group, an amino group and a cyano group; or a substituted-phenyl group having a lower alkylenedioxy group having 1 to 4 carbon atoms as the substituent on the phenyl ring, and the examples including phenyl, 2-chlorophenyl, 3-chlorophenyl, 4-chlorophenyl, 2-fluorophenyl, 3-fluorophenyl, 2-bromophenyl, 3-bromophenyl, 4-bromophenyl, 2-iodophenyl, 4-iodophenyl, 3,5-dichlorophenyl, 2,6-dichlorophenyl, 3,4-dichlorophenyl, 3,4-difluorophenyl, 3,5-dibromophenyl, 3,4,5-trichlorophenyl, 2-methylphenyl, 3-methylphenyl, 4-methylphenyl, 2-ethylphenyl, 3-ethylphenyl, 4-ethylphenyl, 3-isopropylphenyl, 4-hexylphenyl, 3,4-dimethylphenyl, 2,5-dimethylphenyl, 3,4,5-trimethylphenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-hexyloxyphenyl, 3,4-dimethoxyphenyl, 3,4-diethoxyphenyl, 3,4,5-trimethoxyphenyl, 2,5-dimethoxyphenyl, 2-carboxyphenyl, 3-carboxyphenyl, 4-carboxyphenyl, 3,4-dicarboxyphenyl, 2-methoxycarbonylphenyl, 3-methoxycarbonylphenyl, 4-methoxycarbonylphenyl, 2-ethoxycarbonylphenyl, 3-ethoxycarbonylphenyl, 4-ethoxycarbonylphenyl, 4-isopropoxycarbonylphenyl, 4-hexyloxycarbonylphenyl, 3,4-diethoxycarbonylphenyl, 2-methylthiophenyl, 3-methylthiophenyl, 4-methylthiophenyl, 2-ethythiophenyl, 3-ethylthiophenyl, 4-ethylthiophenyl, 4-isopropylthiophenyl, 4-hexylthiophenyl, 3,4-dimethylthiophenyl, 2-acetylphenyl, 3-acetylphenyl, 4-acetylphenyl, 4-formylphenyl, 2-propionylphenyl, 3-butyrylphenyl, 4-hexanoylphenyl, 3,4-diacetylphenyl, 2-nitrophenyl, 3-nitrophenyl, 4-nitrophenyl, 2,4-dinitrophenyl, 2-aminophenyl, 3-aminophenyl, 4-aminophenyl, 2,4-diaminophenyl, 2-cyanophenyl, 3-cyanophenyl, 4-cyanophenyl, 2,4-dicyanophenyl, 3,4-methylenedioxyphenyl, 3,4-ethylenedioxyphenyl, 2,3-methylenedioxyphenyl, 3-methyl-4-chlorophenyl, 2-chloro-6-methylphenyl, 2-methoxy-3-chlorophenyl, 2-hydroxyphenyl, 3-hydroxyphenyl, 4-hydroxyphenyl, 3,4-dihydroxyphenyl and 3,4,5-trihydroxyphenyl groups and the like.

The compounds of the present invention is prepared by various processes and a preferable example of the process is expressed as the following reaction process formula-1:

REACTION PROCESS FORMULA-1

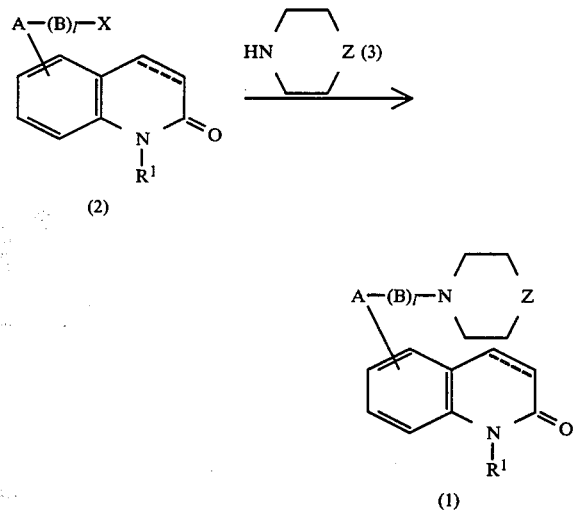

wherein X is a halogen atom, a lower alkanesulfonyloxy group, an arylsulfonyloxy group or an aralkylsulfonyloxy group; A, B, $R^1$, l, Z and the carbon-carbon bond between 3- and 4-positions in the carbostyril skeleton have the same meanings as defined previously.

Thus the compound represented by the general formula (1) is prepared by reacting a compound represented by the general formula (2) with a compound represented by the general formula (3). The reaction is carried out without or in a common inert solvent at a room temperature to about 200° C., preferably at a room temperature to 150° C. and is completed in about 1 to 30 hours.

As to the inert solvent, an ether such as dioxane, tetrahydrofuran, ethylene glycol dimethyl ether, diethyl ether or the like; an aromatic hydrocarbon such as benzene, toluene, xylene or the like; a lower alcohol such as methanol, ethanol, isopropanol or the like; a polar solvent such as dimethylformamide, dimethylsulfoxide, hexamethylphosphoryl triamide, acetone, acetonitrile or the like can be used.

The reaction is advantageously be carried out by using a basic compound as the deacidification agent. As to the deacidification agent, potassium carbonate, sodium carbonate, sodium hydroxide, sodium hydrogencarbonate, sodium amide, sodium hydride, a tertiary amine such as triethylamine, tripropylamine, pyridine, quinoline or the like can be exemplified.

The reaction can also be effected by adding an alkali metal iodide (such as potassium iodide or sodium iodide) or hexamethylphosphoryl triamide as a reaction accelerator.

The ratio of the amount of a compound represented by the general formula (2) to the amount of a compound represented by the general formula (3) in the above reaction there is not any specific restriction, and it is selected from a wide range, and it is usually desirable that the latter is used in an equimolar to an excess quantity, preferably an equimolar to 5 times the molar quantity, more preferably an equimolar to 1.2 times the molar quantity to the former.

The compound represented by the general formula (2) used as the starting material in the reaction process formula-1 includes either known compound or novel compound and such compound is prepared by the following reaction process formulas-2 to -10.

The compound represented by the general formula (3) used as another starting material in the reaction process formula-1 is a known compound and it can easily be prepared by a method disclosed in Japanese Patent Application Kokai (Laid-open) Nos. 2693/1980, 160389/1979 or DOS No. 2912105 or a metal similar to that disclosed in these prior art literatures.

REACTION PROCESS FORMULA-2

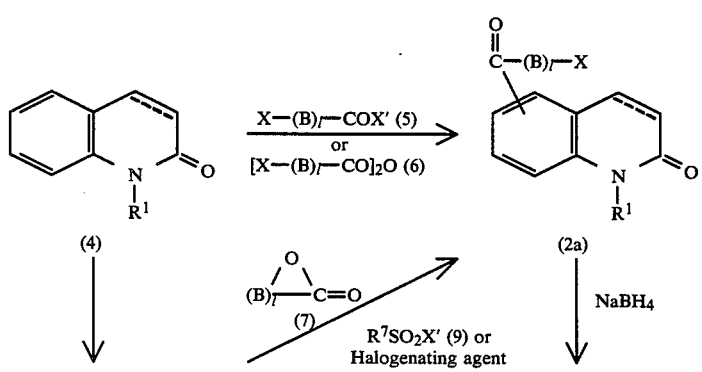

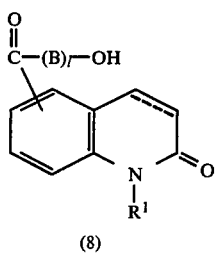

(8)

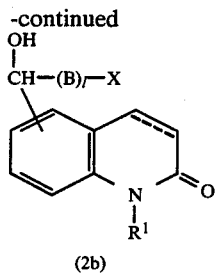

(2b)

wherein X' is a halogen atom; R⁷ is a lower alkyl group, an aryl group or an aralkylgroup; $R^1$, B, X, l and the carbon-carbon bond between 3- and 4-positions in the carbostyril skeleton are the same as defined previously.

In the reaction process formula-2, among the compounds represented by the general formula (2), a compound having a group of the formula

as the definitions of A [a compound of the general formula (2a)] is prepared by reacting a compound of the general formula (4) with a known compound of the general formula (5) or by reacting a known compound of the general formula (4) with a known compound of the general formula (7) to obtain a compound of the general formula (8), then reacting the thus obtained compound of the general formula (8) with a compound of the general formula (9). Among the compounds represented by the general formula (2), a compound having a group of the formula

as the definition of A [a compound of the general formula (2b)] is prepared by reacting a compound of the general formula (2a) with sodium borohydride.

The reaction of a compound of the general formula (4) with a compound of the general formula (5) or a compound of the general formula (6) is generally called as Friedel-Crafts Reaction, and this reaction is carried out in a solvent in the presence of a Lewis acid. As to the solvent used in this reaction, a common solvent used in this type of reaction can advantageously be used, the example of the solvents including carbon disulfide, nitrobenzene, chlorobenzene, dichloromethane, dichloroethane, trichloroethane, tetrachloroethane and the like. As to the Lewis acid, those used in this type of reaction can preferably be used, for example, aluminum chloride, zinc chloride, ferric chloride, stannic chloride, boron tribromide, boron trifluoride, a polyphosphoric acid, a concentrated sulfuric acid can be used. The ratio of the amount of the Lewis acid to be used is optionally selected, and generally the acid is used in 2 to 6 times the molar quantity, preferably 3 to 4 times the molar quantity to the compound of the general formula (4). The ratio of the amount of a compound represented by the general formula (5) or (6) to the amount of a compound represented by the general formula (4) is generally desirable that the former is used in an equimolar quantity or more, preferably 1 to 2 times the molar quantity of the latter. The reaction temperature is optionally selected, and generally the reaction is carried out at 20° to 120° C., preferably at 40° to 70° C. The reaction time varies depend on the starting materials, catalysts and the reaction temperature, and generally the reaction is compounded in 0.5 to 24 hours, preferably 0.5 to 6 hours.

The reaction of a compound of the general formula (4) with a compound of the general formula (7) may be carried out by a method similar to that used in the reaction of a compound of the general formula (4) with a compound of the general formula (5) or (6).

The reaction of a compound of the general formula (8) with a compound of the general formula (9) is carried out in the presence of the deacidification agent in a suitable inert solvent, generally at −30° to 50° C., preferably at 0° to a room temperature, for 1 to 12 hours. The ratio of the amount of a compound of the general formula (8) to the amount of a compound of the general formula (9) is optionally selected from a wide range, and generally, the latter is used in an equimolar quantity or more, preferably 1 to 2 times the molar quantity to the former.

As to the inert solvent, a halogenated hydrocarbon such as methylene chloride, chloroform or the like; an aromatic hydrocarbon such as benzene, toluene or the like; dimethyl sulfoxide, dimethylformamide, pyridine or the like can be exemplified.

In the general formula (9) as to the aryl group as defined in the symbol R⁷ is specifically exemplified such as a substituted or unsubstituted aryl group including phenyl, 4-methylphenyl, 2-methylphenyl, 4-nitrophenyl, 4-methoxyphenyl, 3-chlorophenyl, naphthl groups and the like, and an aralkyl group as defined is specifically exemplified such as a substituted or unsubstituted aralkyl group, including benzyl, 2-phenylethyl, 4-phenylbutyl, 4-methylbenzyl, 2-methylbenzyl, 4-nitrobenzyl, 4-methoxybenzyl, 3-chlorobenzyl, α-naphthylmethyl groups or the like.

The reaction of a compound of the general formula (8) with a halogenating agent is carried out in a suitable inert solvent. As to the halogenating agent used in this reaction N,N-diethyl-1,2,2-trichlorovinylamide, phosphorus pentachloride, phosphorus pentabromide, phosphorus oxychloride, thionyl chloride and the like can be exemplified. As to the inert solvent, an ether such as dioxane, tetrahydrofuran, and the like; a halogenated hydrocarbon such as chloroform, methylene chloride can be exemplified. The ratio of the amount of a compound of the general formula (8) to the amount of a the halogenating agent is at least 2 times the molar quantity, generally an excess amount of the latter is used to the former. The reaction is generally carried out at a room temperature to about 100° C., preferably, at a room temperature to 70° C., and is completed in 1 to 24 hours.

The reaction of a compound of the general formula (2a) with sodium borohydride is carried out in a suitable solvent at a temperature of −60° to 50° C., preferably at −30° to a room temperature for 10 minutes to about 3 hours. As to the inert solvent, water, a lower alcohol such as methanol, ethanol, propanol and the like, an ether such as dioxane, tetrahydrofuran and the like can be exemplified. The ratio of the amount of sodium borohydride to the amount of a compound of the general formula (2a) is at least an equimolar quantity, preferably, 1 to 3 times the molar quantity to the compound of the general formula (2a).

REACTION PROCESS FORMULA-2a

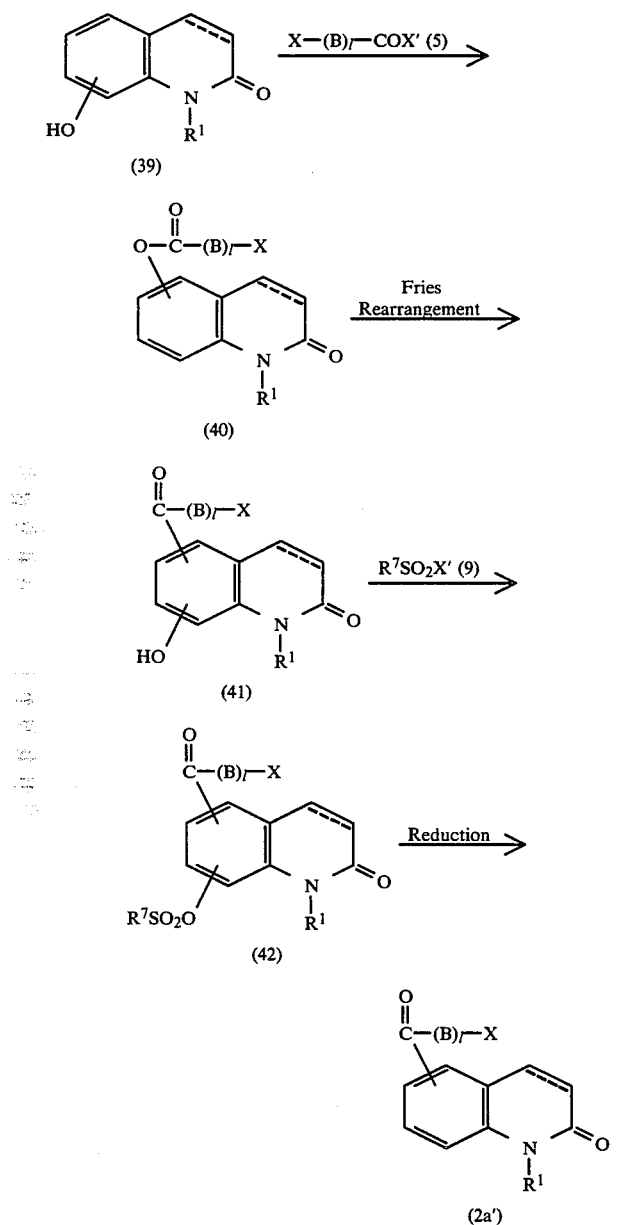

wherein $R^1$, $R^7$, B, l, X, X' and the carbon-carbon bond between 3- and 4-positions in the carbostyril skeleton are the same as defined previously. The substituted position of a group of the formula

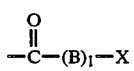

in the general formula (41) is an ortho- or para-position to the hydroxyl group.

The reaction of a known compound of the general formula (39) with a known compound of the general formula (5) is carried out in the presence of a common Lewis acid, for example aluminum chloride, zinc chloride, ferric chloride, stannic chloride or the like as the catalyst. The reaction can be carried out without or in a solvent. As to the solvent, carbon disulfide, nitrobenzene, ether, dioxane and the like are exemplified. In this reaction, the ratio of the amount of halogenoacetyl halide to the amount of hydroxy-carbostyril is an equimolar quantity or a large excess quantity, preferably 1.5 to 5 times the molar quantity of the former to the latter. The reaction is carried out at a temperature of −10° to 100° C., preferably at 0° to 60° C.

The rearrangement reaction of a compound of the general formula (40) is generally known as Fries rearrangement, and the reaction is carried out in the presence of a common Lewis acid for example, aluminum chloride, zinc chloride, ferric chloride, stannic chloride or the like as a catalyst. The reaction can be carried out without or in a solvent. As to the solvent, carbon disulfide, nitrobenzene, diethyl ether, dioxane or the like are exemplified. The reaction is carried out at a room temperature to 150° C., preferably at 50° to 100°. This reaction can be carried out in the presence of a halogenoacetyl halide.

The reaction of a compound of the general formula (41) with a compound of the general formula (9) is carried out by reacting a compound of the general formula (41) with an alkali metal hydride such as sodium hydride, potassium hydride or the like; an alkali metal amide such as sodium amide, potassium amide or the like; an alkali metal such as potassium metal, sodium metal or the like; an alkali metal alkoxide such as sodium methoxide, sodium ethoxide, potassium ethoxide or the like; an alkali metal hydroxide such as sodium hydroxide, potassium hydroxide, lithium hydroxide; or a metal alkyl such as n-butyl lithium, so as to introduce the hydroxyl group in the carbostyril ring into the corresponding alkali metal salt. The reaction for obtaining the alkali metal salt can be carried out in a suitable solvent for example, an aromatic hydrocarbon solvent such as benzene, toluene, xylene or the like, n-hexane, cyclohexane, an ether type solvent such as diethyl ether, 1,2-dimethyxyethane, dioxane, tetrahydrofuran, an aprotic polar solvent such as dimethylformamide, hexamethylphosphoryl triamide, dimethyl sulfoxide or the like, at a temperature of 0° to 200° C., preferably at a room temerature for 30 minues to 5 hours. Thus obtained alkali metal salt of hydroxycarbostyril derivative is then reacted with a compound of the general formula (9) at a temperature of 0° to 200° C., preferably at 0° C. to a room temperature for 1 to 5 hours to obtain a compound of the general formula (42). The ratio of the amount of the alkali metal hydroxide or a compound of said alkali metal hydroxide to the amount of a compound of the general formula (41) is generally 1.0 to 5.0 times the molar quantity, referably 1.0 to 1.2 times the molar quantity of the former to the latter. The ratio of the amount of a compound of the general formula (9) to the amount of a compound of the general formula (41) is generally 1.0 to 5.0 times the molar quantity, preferably 1.0 to 1.2 times the molar quantity of the former to the latter.

The hydrogenation reaction of a compound of the general formula (42) is carried out ina solvent such as water, 10% metal hydroxide aqueous solution, methanol, ethanol, isopropanol, diethyl ether, dioxane or the like. The hydrogenation reaction is carried out in the presence of a catalyst for example palladium black, palladium carbon, Raney nickel or the like, preferably 5 to 20% of palladium carbon is used as the hydrogenation catalyst, under a ordinary pressure to 10 atmospheric pressure, preferably under hydrogen gas stream of ordinary pressure at a temperature of 0° to 40° C., preferably at a room temperature, for 5 to 20 hours, with shaking or stirring. The reaction can be proceeded preferably by using the catalyst in the amount of 0.1 to 30%, preferably 5 to 20% or 10 to 20% of palladium carbon to the amount of the compound of the general formula (42).

REACTION PROCESS FORMULA-2b

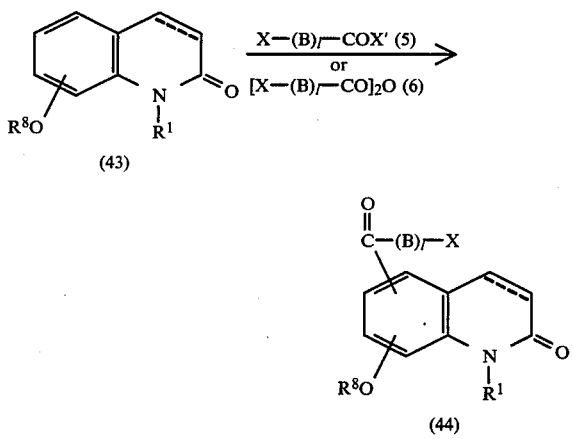

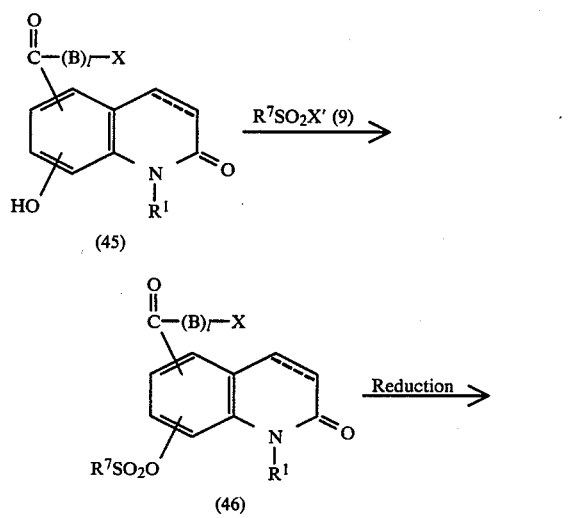

wherein $R^1$, $R^7$, l, X, X', and the carbon-carbon bond betweend 3- and 4-positions in the carbostyril skeleton are the same as defined previously; and the substituted position of a group of the formula

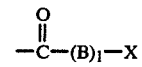

in the general formula (44) is the ortho- or para-position to $OR^8$; and $R^8$ is a lower alkyl group.

The reaction of a compound of the general formula (43) with a compound of the general formula (5) or (6) can be carried out by a method similar to that used in the reaction of a compound of the general formula (4) with a compound of the general formula (5) or (6) in reaction process formula-2.

The dealkylation reaction of a compound of the general formula (44) is carried out by reacting it with a hydrogen halide. As to the hydrogen halide used in this reactin, hydrogen bromide, hyddrogen chloride, hydrogen iodide or the like are exemplified. The hydrogen halide is generally used in a suitable solvent, specifically, it is used in the form of a hydrohalic acid in water used as the solvent. Hydrogen bromide can be exemplified as a preferable hydrogen halide, and generally 10 to 50% (preferably 47%) aqueous solution of hydrogen bromide is used. The ratio of amount of hydrogen halide to the amount of a compound of (44) is generally an equimolar quantity or an excess amount, preferably an excess amount of hydrogen halide is used to the latter. The reaction can advantageously be carried out under heating condition, and generally at a temperture of 100° to 150° C. (preferably under refluxing condition by heating) for 5 to 20 hours.

The reaction of a compound of the general formula (45) with a compound of the general formula (9) and the reduction of a compound of the general formula (46) can be carried out under conditions similar to those used in the reaction of a compound of the general formula (41) with a compound of the general formula (9) and reduction of a compound of the general formula (42).

REACTION PROCESS FORMULA-3

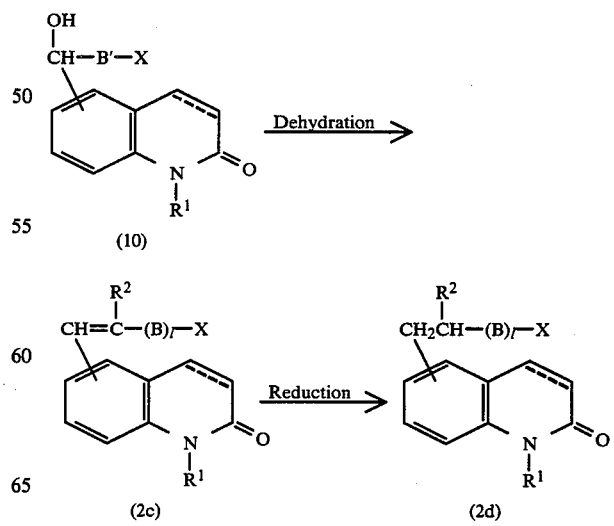

wherein B' is a group of the formula

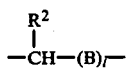

(wherein $R^2$, B and l are the same as defined previously) and $R^1$, $R^2$, B, l, X and the carbon-carbon bond between 3- and 4-positions in the carbostyril skeleton are the same as defined previously.

The dehydration reaction of a compound of the general formula (10) is carried out in a solvent by reacting it with an acid or a basic compound. As to the solvent used in this reaction can be selected from those usually used in this type of reaction and are exemplified usch as pyridine, diacetone alcohol, colidine, dimethylformamide, tetrahydrofuran, benzenesulfonic acid, benzene, xylene, acetic anhydride, acetic acid, methanol, ethanol, dimethyl sulfoxide and the like. As to the acid, hydrochloric acid, sulfuric acid, boric acid, N-bromoacetamide-sulfur dioxide, Florisil (a trademark for a powdered magnesia-silica), hydrobromic acid, iodine, mesityl chloride-sulfur dioxide, methylchlorosulfide, naphthalene-βsulfonic acid, oxalic acid, phosphoryl chloride, phthalic anhydride, thionyl chloride, p-toluenesulfonic acid, p-toluenesulfonyl chloride, potassium hydrogensulfate, phosphorus pentaoxide and the like are exemplified.

As to the basic compound, sodium hydroxide, potassium hydroxide, and the like are exemplified. The ratio of the amount of the acid or basic compound to the amount of the compound of the general formula (10) is generally an equimolar to 10 times the molar quantity, preferably quimolar to 8 times the molar quantity of the former to the latter. The reaction is generally carried out at 20° to 150° C., preferably at 20° to 100° C., and is generally completed in 10 minutes to 16 hours.

The reduction of a compound of the general formula (2c) is carried out by a method of reduction by using a hydrogenating reducing agent or by a method of catalytic reduction. In the method of reduction by using a hydrogenating reducing agent, sodium borohydride, lithium aluminium hydride or the like, preferably sodium borohydride is used as the hydrogenating reducing agent. The hydrogenating reducing agent may be used at least an equimolar quantity, preferably 1 to 3 times the molar quantity to the amount of a compound of the general formula (2c). The reduction by using hydrogenating reducing agent can be carried out in a suitable solvent, for example water, a lower alcohol such as methanol, ethanol, isopropanl or the like, an ether such as tetrahydrofuran, diethyl ether or the like, at a temperature of −60° to 50° C., preferably −30° to a room temperature, and generally the reaction is completed in 10 minutes to 3 hours. The reduction by using lithium aluminium hydride as the reducing agent, an anhydrous solvent for example diethyl ether, tetrahydrofuran or the like may be used. In case of applying a catalytic reduction, a catalyst for catalytic reduction commonly used for example, platinum oxide, palladium black, palladium carbon, platinum black, Raney nickel or the like may be used as the reducing catalyst. The ratio of the amount of catalyst to the amount of a compound of the general formula (2c) is usually 0.2 to 0.5 time by weight of the former to the latter.

The catalytic reduction is carried out in a suitable solvent, for example water, methanol, ethanol, isopropanol, dioxane, tetrahydrofuran, ethyl ether or the like, and generally at a pressure of 1 to 10 atmospheric pressure, preferably 1 to 3 atmospheric pressure of hydrogen gas, under a well-shaking condition. The catalytic reduction is carried out, in general, at −30° C. to the boiling point of the solvent used, preferably at 0° C. to a room temperature.

In the reduction mentioned above, in case of catalytic reduction at a lower temperature about 0° C. to a room temperature, or in case of a reduction by using hydrogenation reducing agent, the double bond between 3- and 4-positions in the carbostyril skeleton is not reduced substantially, but it is formed a compound wherein the carbonyl group bonded at 5-8-position in the carbostyril skeleton is reuced. In the reduction mentioned above, a compound having halogen atoms, lower alkoxycarbonyl groups, lower alkylthio groups, lower alkanoyl groups, nitro group or cyano groups as the substituents on the phenyl ring of the substituted-phenyl group as defined in symbol $R^3$, and a compound having a lower alkenyl group or a lower alkynyl group as the substituent as defined in symbol $R^1$, there are some cases that such groups of the substituents are reduced at the same time.

REACTION PROCESS FORMULA-4

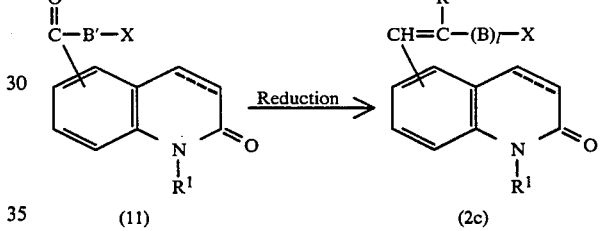

(11)  (2c)

wherein $R^1$, $R^2$, B, B', l, X and the carbon-carbon bond between 3- and 4-positions in the carbostyril skeleton are the same as defined previously.

The reaction for obtaining a compound of the general formula (2c) by reducing a compound of the general formula (11) is called the Bamford-Stevens Reaction and is carried out in a suitable solvent in the presence of a basic compound by reacting with p-toluenesulfonylhydrazide. As to the solvent, any solvent which may be used in this type of reaction can be used in the reaction and are exemplified as mehanol, ethanol, ethylene glycol, diethylene glycol, diethyl ether, tetrahydrofuran, hexane and the like. Also, as to the basic compound, any basic compound which may be used in this type of reaction can preferably be used, and sodium methoxide, sodium ethoxide, sodium glycoside, lithium aluminium hydride, sodium borohydride, n-butyl lithium and the like are exemplfied.

The ratio of the amount of the basic compound to the amount of a comound of the general formula (11) can be selected from a wide range, and generally 2 times the molar quantity or an excess amount of the former is used to the latter. The ratio of the amount of p-toluenesulfonylhydrazide to the amount of a compound of the general formula (11) is generally used at least an equimolar or more quantity, preferably 1 to 2 times the molar quantity of the former to the latter. The reaction is carried out generally at a temperature of 0° to 200° C., preferably, at 25° to 165° C. and generally, the reaction is completed in 0.5 to 6 hours.

REACTION PROCESS FORMULA-5

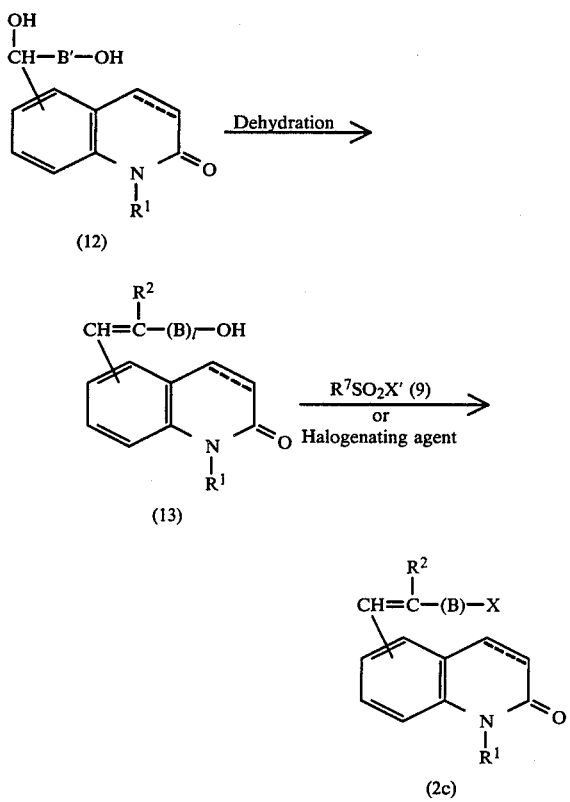

wherein $R^1$, $R^2$, B, B', l, $R^7$, X, X' and the carbon-carbon bond between 3- and 4-positions in the carbostyril skeleton are the same as defined previously.

The dehydration reaction of a compound of the general formula (12) can be carried out by a method similar to that used in the dehydration of a compound of the general formula (10).

The reaction of a compound of the general formula (13) with a compound of the general formula (9) can be carried out by a method similar to that used in the reaction of a compound of the general formula (8) with a compound of the general formula (9). Further, the reaction of a compound of the general formula (13) with a halogenating agent can be carried out by a method simiar to that used in the reaction of a compound of the general formula (8) with a halogenating agent.

REACTION PROCESS FORMULA-6

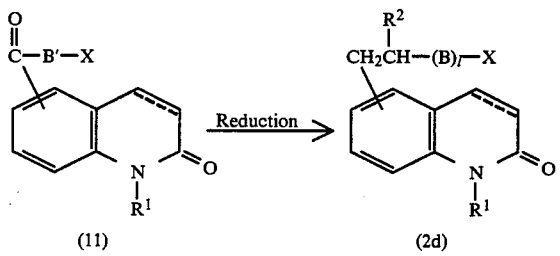

wherein $R^1$, $R^2$, B, B', l, X and the carbon-carbon bond between 3- and 4-positions in the carbostyril skeleton are the same as defined previously.

The reduction of a compound of the general formula (11) to obtain a compound of the general formula (2b) can be carried out by two methods as follows.

The first method is a method called as Clemmensen Reduction by which the carbonyl group in a compound of the general formula (11) is reduced to methylene group with zinc or mercury and concentrated hydrochloric acid. This reaction can be carried out in a suitable solvent which may be selected from those commonly used in this type of reaction, and toluene and ethanol are exemplified. The ratio of the amount of zinc or mercury to the amount of compound of the general formula (11) is generally 10 to 30 times the molar quantity, preferably 14 to 23 times the molar quantity to the latter. The reaction is carried out generally at 50° to 250° C., preferably, at 70° to 230° C. and is completed in about 8 to 30 hours.

The second method is a method called as Wolff-Kishner Reduction by which the carbonyl group in the compound of the general formula (11) is reduced to methylene group with hydrazine hydrate in the presence of a suitable basic compound in a suitable solvent. As to the solvent used in this reaction, one selected from those used in this type of reaction may advantageously be used, and the examples including methanol, ethanol, n-butanol, ethylene glycol, propylene glycol, triethylene glycol, diethylene glycol, toluene and the like. Examples of the basic compound include sodium methoxide, sodium diethylene glycoside, potassium hydroxide, potassium t-butoxide and the like. The ratio of the amount of the basic compound to the amount of the compound of the general formula (11) is generally 2 to 25 times the molar quantity, preferably 3 to 22 times the molar quantity to the latter. The ratio of the amount of hydrazine hydrate to the amount of the compound of the general formula (11) may be suitably determined, and generally the former is used in 2 to 80 times the molar quantity, preferably 3 to 74 times the molar quantity to the latter. The reaction is generally carried out at 100° to 250° C., preferably at 110° to 210° C. and is completed in 4–60 hours.

REACTION PROCESS FORMULA-7

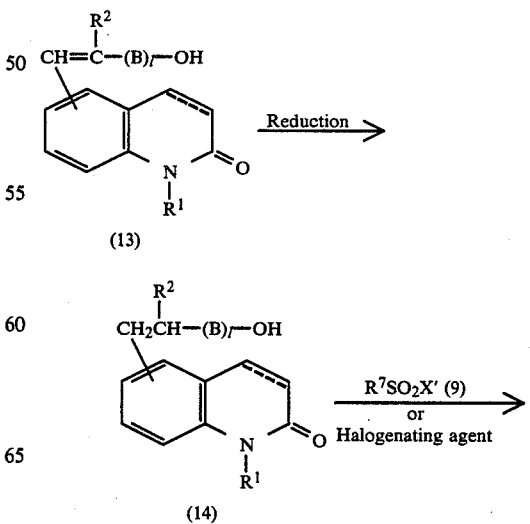

-continued

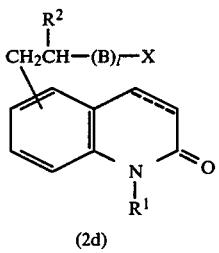

(2d)

wherein $R^1$, $R^2$, $R^7$, B, l, X, X' and the carbon-carbon bond between 3- and 4-positins in the carbostyril skeleton are the same as defined previously.

The reduction of a compound of the general formula (13) to obtain a compound of the general formula (14) can be carried out by a method similar to that used in the reduction of a compound of the general formula (2c) to obtain a compound of the general formula (2d) as in the reaction process formula-3.

The reaction of a compound of the general formula (14) with a compound of the general formula (a) or with a halogenating agent can be carried out by a method similar to that used in the reaction of a compound of the general formula (8) with a compound of the general formula (9) or with a halogenating agent to obtain a compund of the general formula (2a) as in the reaction process formula-2.

REACTION PROCESS FORMULA-8.

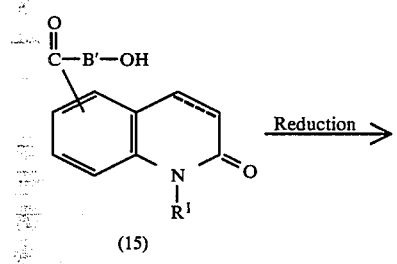

(15)

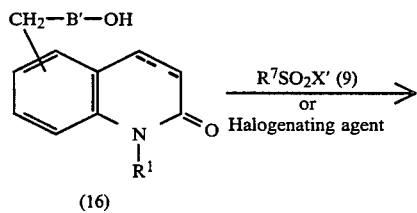

(16)

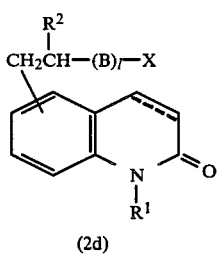

(2d)

wherein $R^1$, $R^2$, $R^7$, B, B', l, X, X' and the carbon-carbon bond between 3- 4-positions in the carbostyril skeleton are the same as defined previously.

The reduction of a compound represented by the formula (15) to obtain a compound represented by the general formula (16) can be carried out in the presence of a reducing catalyst in a suitable solvent, for example water, a lower alcohol such as methanol, ethanok, isopropanol or the like, an ethers such as dioxane, tetrahydrofuran, ethyl ether and the like, and generally at −30° C. to the boiling point of a solvent (preferably at 60° to 100° C.), under 1 to 10 atmospheric pressure (preferably 1 to 3 atmospheric pressure) of hydrogen gas stream. As to the catalyst used in this reduction, any catalyst used in catalytic reductions can be used and the examples including platinum oxide, palladium black, palladium carbon, Raney nickel and the like. The ratio of the amount of the catalyst to the amount of a compound of general formula (15) is generally, 10 to 50% by weight quantity to the latter. The reduction can be promoted by adding an acid for example a concentrated hydrochloric acid into the reaction system.

The reaction of a compound of the general formula (16) with a compund of the general formula (9) or with a halogenating agent can be carried out by a method similar to that used in the reaction of a compound of the general formula (8) with a compound of the general formula (9) or with a halogenating agent to obtain a compound of the general formula (2a) as in the reaction process formula-2.

REACTION PROCESS FORMULA-9

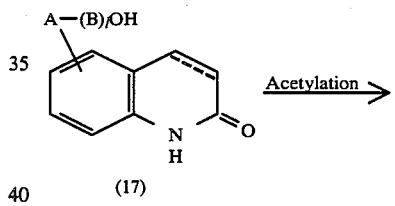

(17)

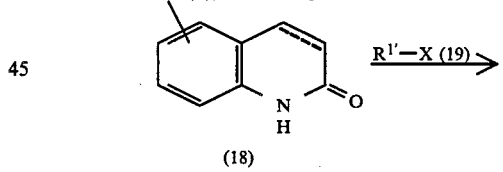

(18)

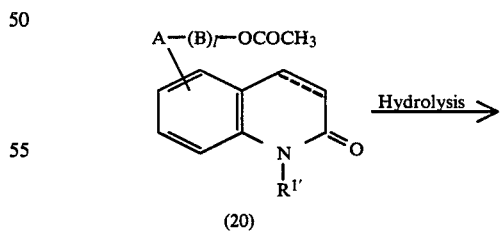

(20)

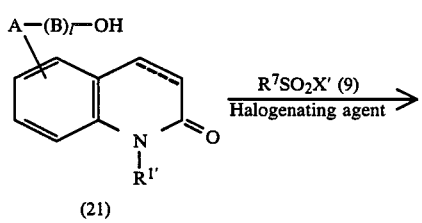

(21)

-continued

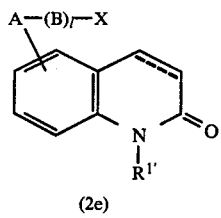

(2e)

wherein $R^{1'}$ is a lower alkyl group, a phenyl-lower alkyl group, a lower alkenyl group or a lower alkynyl group; and A, B, l, $R^7$, X, X' and the carbon-carbon bond between 3- and 4-positions in the carbostyril skeleton are the same as defined previously.

The acetylation of a compound of the general formula (17) can be carried out by reacting it with an acetylating agent in the presence of a suitable catalyst in a suitable solvent. As to the catalysts which can be used in this reaction are exemplified as sulfuric acid, hydrochloric acid, boron trifluoride, pyridine, sodium acetate and the like. As to the solvents which can be used in this reaction are examplified as acetic acid, pyridine and the like. As to the acetylating agents which can be used in this reaction are exemplified as acetic anhydride, acetyl chloride, 2,3-acetoxypyridine and the like. The ratio of the amount of the acetylating agent to the amount of a compound of the general formula (17) is generally 1 to 10 times the molar quantity, preferably 1 to 7 times the molar quanity to the latter. The reaction is generally carried out at 0° to 150° C., preferably at 20° to 110° C. and is generally completed in 0.5 to 6 hours.

The reaction of a compound of the general formula (18) with a compound of the general formula (19) can be carried out in the presence of a basic compound in a suitable solvent. As to the basic ompounds which can be used in this reaction are exemplified as sodium hydride, potassium metal, sodium metal, sodium amide, potassium amide. As to the solvents which can be used in this reaction are exemplified as ethers such as dioxane, diethylene glycol dimethyl ether, diethyl ether and the like, aromatic hydrocarbons such as toluene, xylene and the like, dimethylformamide, dimethyl sulfoxide, hexamethylphosphoryl triamide and the like. The ratio of the amount of a compound of the general formula (18) to the amount of a compound of the general formula (19) is not specifically restricted and the ratio may suitably be selected from a wide range, and generally, the latter is used in an equimolar quantity or more, preferably 1 to 2 times the molar quantity to the former. The reaction is generally carried out at −50° to 70° C., preferably −30° C. to a room temperature and is generally completed in 0.5 to 12 hours.

The hydrolysis of a compound of the general formula (20) can be carried out, in a suitable solvent, by reacting it with an acid or a basic compound. As to the solvents which can be used in this reaction are exemplified as water, methanol, ethanol, isopropanol and the like. As to the acids which can be used in this reaction are exemplified as hydrochloric acid, sulfuric acid and the like. As to the basic compounds which can be used in this reaction are exemplified as potassium carbonate, sodium carbonate, sodium hydrogencarbonate, potassium hydroxide, sodium hydroxide and the like. The ratio of the amount of the acid or the basic compound to the amount of a compound of the general formula (20) is at least an equimolar quantity or more, generally, a great excess amount of the former is used to the latter. The reaction temperature may generally be of a room temperature to 100° C. and the reaction is generally completed in 0.5 to 5 hours.

The reaction of a compund of the general formula (21) with a compound of the general formula (9) or with a halogenating agent can be carried out by a method similar to that used in the reaction of a compound of the general formula (8) with a compound of the general formula (9) or with a halogenating agent to obtain a compound of the general formula (2a) as in the reaction process formula-2.

A compound of the general formula (2e) thus prepared can be converted into mutually from one to another as shown in reaction process formula-10, that is a compound of the general formula (2f) having a single bond between 3- and 4-positions in the carbostyril skeleton can be converted into a compund of the general formula (2g) having a double bond between 3- and 4-positions in the carbostyril skeleton and vice versa.

REACTION PROCESS FORMULA-10

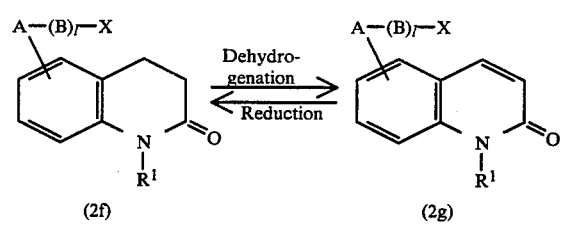

(2f)    (2g)

wherein $R^1$, A, B, and l are the same as defined previously.

Further, a compund of the general formula (1) of the present invention can also be prepared by a method as shown in reaction process formula-11.

REACTION PROCESS FORMULA-11

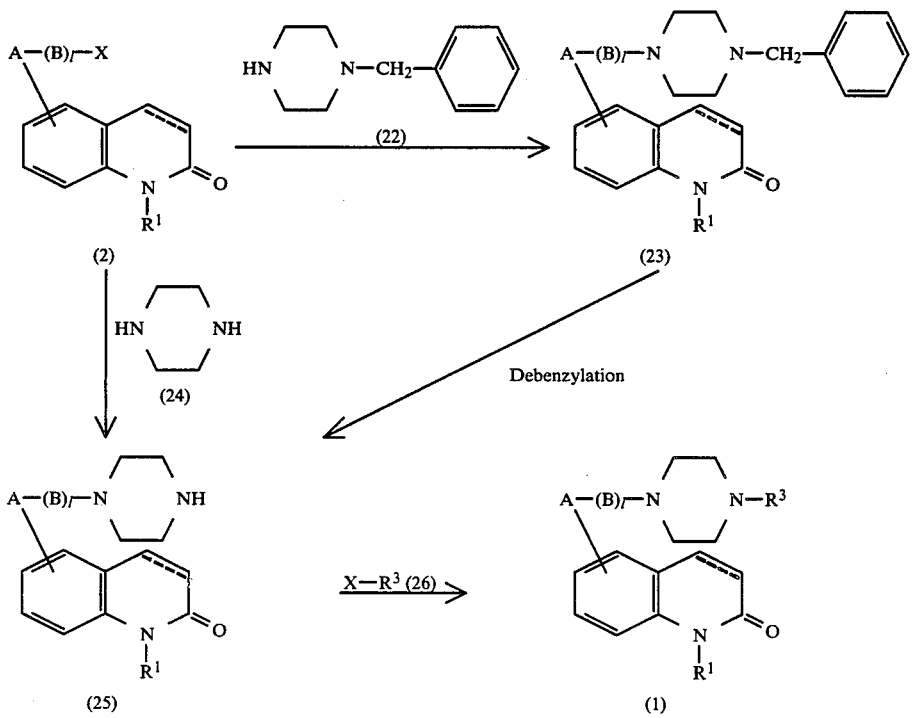

wherein $R^1$, $R^3$, A, B, l, X and the carbon-carbon bond between 3- and 4-positions in the carbostyril skeleton are the same as defined previously.

Thus, a compound of the general formula (1) of the present invention can be prepared by reacting a compound of the general formula (25) with a known compound of the formula (26). A compound of the general formula (25) is prepared by reacting a compund of the general formula (2) with a known compound of the general formula (24), or by reacting a compound of the general formula (2) with a known compund of the general formula (22) to form a compound of the general formula (23), then removing the benzyl group from this compound.

The reaction of a compound of the general formula (2) with a compound of the general formula (24) and the reaction of a compound of the general formula (2) with a compound of the general formula (22) can be carried out by a method similar to that used in the reaction of a compound of the general formula (2) with a compound of the general formula (3) in the reaction process formula-1.

The reaction of a compound of the general formula (25) with a compound of the formula (26) is carried out in a suitable inert solvent in the absence or presence of a basic condensing agent. The solvent used in this reaction is exemplified and including aromatic hydrocarbons such as benzene, toluene, xylene and the like, alcohols such as methanol, ethanol, propanol, butanol, 3-methoxy-1-butanol, ethyl cellosolve, methyl cellosolve and the like, pyridine, acetone, dimethyl sulfoxide, dimethylformamide, hexametylphosphoryl triamide and the like. The basic condensing agent used in this reaction is exemplified and including sodium carbonate, potassium carbonate, sodium hydrogencarbonate, potassium hydrogencarboate, sodium hydroxide, potassim hydroxide, sodium hydride, potassium hydride, triethylamine and the like. The reaction can easily be carried out by adding copper power as a catalyst. The reaction of the amount of a compound of the general formula (25) to the amount of a compound of the general formula (26) is not specifically restricted and can be selected from a wide range, and generally the latter is used in an equimolar quantity or more, preferably 1 to 5 times the molar amount to the former. The reaction is generally carried out at a room temperature to 180° C., preferably at 100° to 150° C. The reaction is generally completed in about 3 to 30 hours.

The debenzylation of a compound of the general formula (23) can be carried out under conditions of an usual removal reaction of N-benzyl group, for example, the reaction can be carried out in the presence of a catalyst for catalytic reduction such as palladium carbon, palladium black, platinum black or the like in a suitable solvent at 0° C. to a room temperature for 0.5 to 5 hours. The solvent used in this reaction is exemplified as water, a lower alcohol such as ethanol, methanol, isopropanol or the like, an ether such as dioxane, tetrahydrofuran or the like, acetic acid, or the like. The catalyst for catalytic reduction is generally used in an amount of 10 to 50% by weight to a compound of the general formula (23). This reaction can also be accelerated by adding an acid such as concentrated hydrochloric acid as a catalyst in the reaction system.

A compound of the general formula (1) of the present invention can also be prepared by a method in the following reaction process formula-12.

REACTION PROCESS FORMULA-12

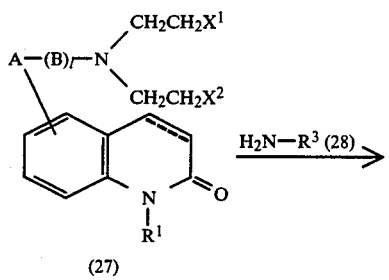

(27)

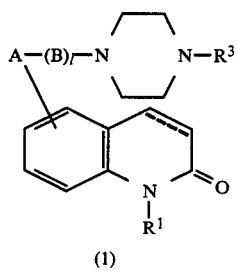

(1)

wherein $X^1$ and $X^2$ are respectively halogen atoms, lower alkanesulfonyloxy groups, arylsulfonyloxy groups, aralkylsulfonyloxy groups or hydroxyl groups; $R^1$, $R^3$, A, B, l, and the carbon-carbon bond between 3- and 4-positions in the carbostyril skeleton are the same as defined previously.

Thus, a compound of the general formula (1) of the present invention is prepared by reacting a compund of the general formula (27) with a known compound of the generald formula (28).

In case a compound of the general formula (27), wherein $X^1$ and $X^2$ are halogen atoms, lower alkanesulfonyloxy groups, arylsulfonyloxy groups or aralkylsulfonyloxy groups is used, the reaction of the compound of the general formula (27) with a compound of the general formula (28) is generally carried out in a suitable inert solvent in the absence or presence of a basic condensing agent. The inert solvent can be exemplified as a aromatic hydrocarbon such as benzene, toluene, xylene, and or like, a lower alcohol such as methanol, ethanol, isopropanol, butanol or the like, acetic acid, ethyl acetate, dimethyl sulfoxide, dimethylformamide, hexamethylphosphoryl triamide or the like. The basic condensing agent cand be exemplified as carbonate such as sodium carbonate, potassium carbonate, sodium hydrogencarbonate, potassium hydrogencarbonate or the like, a metal hydroxide, such as sodium hydroxide, potassium hydroxide, or the like, a metal alcoholate such as sodium methylate, sodium ethylate or the like or a tertiary amine such as pyridine, triethylyamine or the like.

The ratio of the amount of a compund of the general formula (27) to the amount of a compound of the general formula (28) is not specifically restricted and may be selected from a wide range and generally the latter is used in an equimolar or more, preferably 1 to 5 times the molar amount to the former. The reaction is generally carried out at a temperature of 40° to 120° C., preferably at 50° to 100° C., and is completed generally in 5 to 30 hours.

In case a compound of the general formula (27), wherein $X^1$ and $X^2$ are hydroxyl groups is used, the reaction of the compound of the general formula (27) with a compound of the general formula (28) is carried out in the presence of a dehydrating condensing agent in the absence or presence of a suitable solvent. As to the dehydrating condensing agent which can be used in the reaction are exemplified and including a condensed phosphoric acids such as polyphosphoric acid, a phosphoric acid such as orthophosphoric acid, pyrophosphoric acid, metaphosphoric acid, a phosphorous acid such as orthophosphorous acid, a phosphoric anhydride such as phosphorus pentaoxide, an inorganic acid such as hydrochloric acid, sulfuric acid, boric acid, a metal phosphate such as sodium phosphate, boron phosphate, ferric phosphate, aluminum phosphate, activated alumina, sodium bisulphate, Raney nickel and the like. As to the solvent which can be used in the reaction are exemplified as a high boiling point solvent such as dimethylformamide, tetraline or the like. The ratio of the amount of a compound of the general formula (27) to the amount of a compound of the general formula (28) is not specifically restricted and can be selected from a wide range and generally the latter is used in an equimolr amount or more, preferably 1 to 2 times the molar amount to the former. The amount of the dehydrating condensing agent is not specifically restricted and can be selected from a wide range, generally, the condensing agent is used in a catalytic amount or more, preferably 0.5 to 5 times the molar quantity to the amount of a compound of the general formula (27).

In the above mentioned reaction, the reaction may advantageously be carried out in an inert gas stream such as carbon dioxide or nitrogen gas for the purpose of preventing oxidation. The reaction can be carried out either at a normal pressure or under pressure and preferably can be carried out at a normal pressure. The reaction is carried out generally at 100° to 350° C., preferably at 125° to 255° C. and is completed in about 3 to 10 hours. In the above reaction, a compound of the general formula (28) can be used in the form of a salt.

REACTION PROCESS FORMULA-13

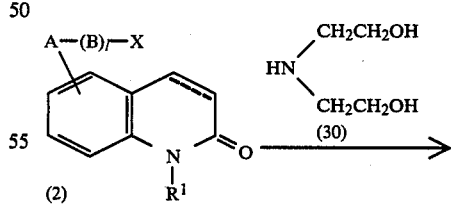

(2)

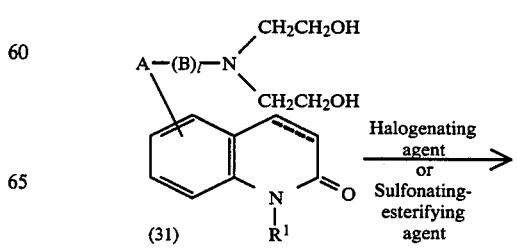

(31)

-continued

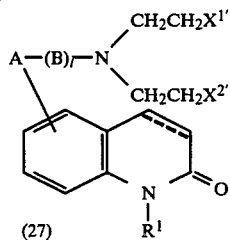

wherein $R^1$, A, B, l, X and the carbon-carbon bond between 3- and 4-positions in the carbostyril skeleton are the same as defined previously; and $X^{1'}$ and $X^{2'}$ are respectively a halogen atom, a lower alkanesulfonyloxy group, an arylsulfonyloxy group or an aralkylsulfonyloxygroup.

REACTION PROCESS FORMULA-14

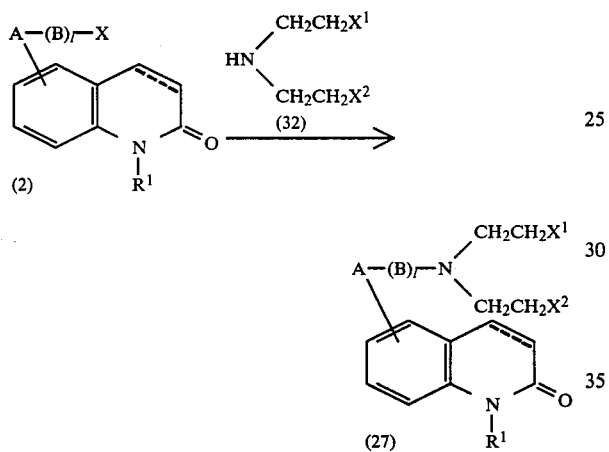

wherein $R^1$ A, B, l, X, $X^1$, $X^2$ and the carbon-carbon bond between 3- and 4-positions in the carbostyril skeleton are the same as defined previously.

According to reaction process formula-13, a compound of the general formula (27) is prepared by reacting a compound of the general formula (2) with a known compound of the formula (30) to obtain a compound of the general formula (31), then reacting this compound with a halogenating agent or sulfonating esterifying agent. The reaction of a compound of the general formula (2) with a compound of the general formula (30) can be carried out by a method similar to that used in the reaction of a compound of the general formula (2) with a compound of the general formula (3) in reaction process formula-1.

The reaction of a compound of the general formula (31) with a halogenating agent can be carried out by a method similar to that in the reaction of a compound of the general formula (13) with a halogenating agent in the reaction process formula-5.

The reaction of a compound of the general formula (31) with a sulfonating-esterifying agent is carried out in a suitable inert solvent in the presence of a basic condensing agent. The sulfonating-esterifying agent is exemplified such as an alkanesulfonyl halide for example mesityl chloride, mesityl bromide, tosyl chloride or the like, or arylsulfonyl halide or the like.

The inert solvent is exemplified such as an aromatic hydrocarbon for example benzene, toluene or the like, an ether for example dioxane, tetrahydrofuran or the like, pyridine, dimethyl sufloxide, dimethylformamide, hexamethylphosphoryl triamide or the like. The basic condensing agent is examplified such as a tertiary amine for example triethylamine, pyridine, N,N-dimethylaniline or the like, or sodium carbonate, potassium carbonate, sodium hydrogencarbonate or potassium hydrogencarbonate.

The ratio of the amount of a compound of the general formula (31) to the sulfonating-esterifying is generally at least 2 times the molar quantity, preferably 2 to 4 times the molar quantity to the former. The reaction is generally carried out at a temperature of $-30°$ to $100°$ C., preferably at $0°$ to $50°$ C., and is generally completed in general in about 1 to 15 hours.

According to reaction process formula-14, a compound of the general formula (27) is prepared by reacting a compound of the general formula (2) with a known compound of the general formula (32). The reaction of a compound of the general formula (2) with a known compound of the general formula (32) can be carried out by a method similar to that used in the reaction of a compound of the general formula (2) with a compound of the general formula (3) as in the reaction process formula-1.

Further, a compound of the general formula (1) of the present invention can also be prepared by the following reaction process formula-15.

REACTION PROCESS FORMULA-15

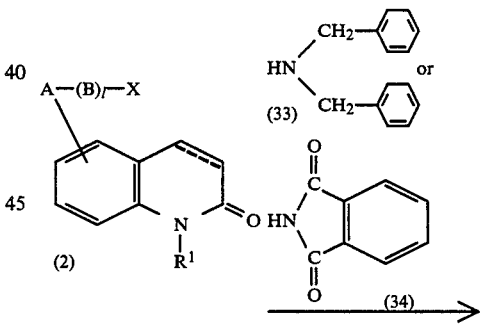

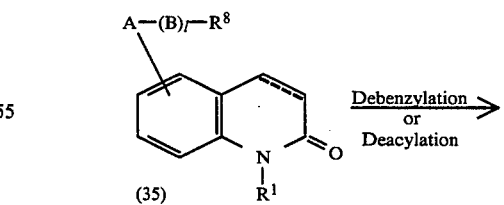

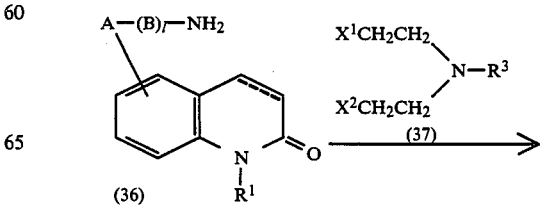

-continued

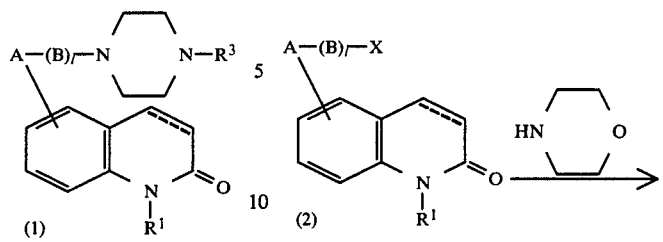

wherein R⁸ is a group of the formula

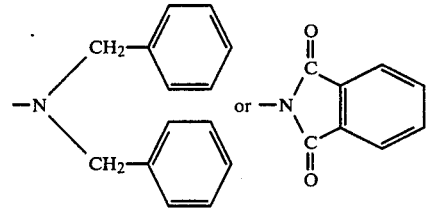

and $R^1$, $R^3$, A, B, l, X, $X^1$, $X^2$ and the carbon-carbon bond between 3- and 4-positions in the carbostyril skeleton are the same as defined previously.

Thus, a compound of the general formula (1) of the present invention is prepared by reacting a carbostyril derivative of the general formula (36) with a known compound of the general formula (37). A compound of the general formula (36) is prepared by reacting a compound of the general formula (2) with a known compound of the general formula (33) or (34) to obtain a compund of the general formula (35), then debenzylation or deacylating a compound of the general formula (35). The reaction of a compound of the general formula (2) with a compound of the general formula (33) or (34) can be carried out by a method smilar to that used in the reaction of a compound of the general formula (2) with a compound of the general formula (3) as in the reaction formula-1.

The debenzylation of a compound of the general formula (35) can be carried out under the conditions used in a common reaction for removing N-benzyl group, for example this reaction can be carried out by heating a compound of the general formula (35) in an aqueous solution of hydrobromic acid. Further, deacylation of a compound of the general formula (35) can be carried out under the conditions similar to those used in a hydrolysis of a compound of the general formula (20) as in the reaction process formula-9. The reaction of a compound of the general formula (36) with a compound of the general formula (37) may be carried out by a method similar to that used in the reaction of a compound of the general formula (27) with a compound of the general formula (28) as in the reaction process formula-12.

A compound of the general formula (1) of the present invention is also prepared by a method as shown in the following reaction process formula-16.

REACTION PROCESS FORMULA-16

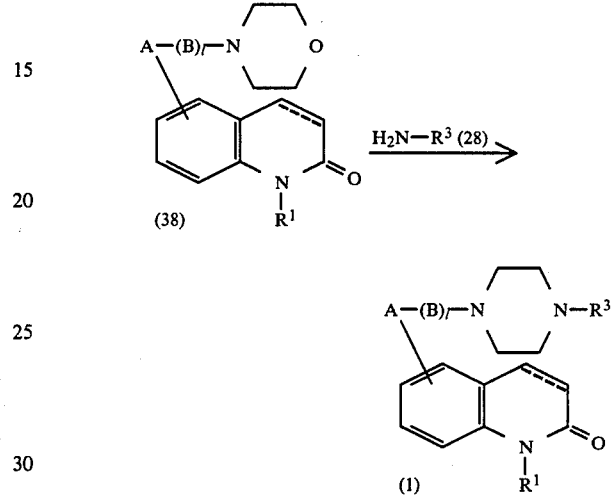

wherein $R^1$, $R^3$, A, B, l, and the carbon-carbon bond between 3- and 4-positions in the carbostyril skeleton are the same as defined previously.

A compound of the general formula (1) of the present invention is prepared by reacting a known carbostyril derivative of the general formula (38) with a known compound of the general formula (28). The compound of the general formula (38) is prepared by reacting a compound of the general formula (2) with morpholine. the reaction of a compound of the general formula (2) with morpholine can be carried out by a method similar to that used in the reaction of a compound of the general formula (2) with a compound of the general formula (3).

The reaction of a compound of the general formula (38) with a compound of the general formula (28) is carried out in the absence or presence of a suitable solvent in the presence of an acid. As to the solvent used in the reaction is a high boiling point solvent and is exemplified such as 1,2,3,4-tetrahydronaphthalene, dimethylformamide, dimethylsulfoxide, hexamethylphosphoryl triamide or the like. As to the acid used in the reaction, it is exemplified such as hydrochloric acid, hydrobromic acid, sulfuric acid or the like. The ratio of the amount of a compound of the general formula (38) to the amount of a compound of the general formula (28) is not specifically restricted and can be selected from a wide range, generally the latter is used at least an equimolar quantity, preferably 1 to 2 times the molar quantity to the former. The reaction may be carried out generally at 50° to 250° C., preferably at 150° to 200° C. and is completed in 1 to 24 hours.

In this reaction, a compound having a lower alkoxycarbony group or cyano group as the subtituent on the substituted-phenyl group, there are some cases that said substituents may be converted at the same time into the corresponding carboxyl broups. Further, in this reaction, a compound having a lower alkoxy group or a lower alkylenedioxy group as the substituent on the substituted-phenyl group, there are some cases that said substituents may be converted at the same time into the corresponding hydroxyl group.

Among the compound of the general formula (38) used in the reaction process formula-16, a compound having a group of the formula

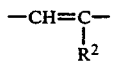

as the symbol A can be converted into a compound having a group of the formula

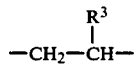

as the symbol A, by reducing the former compound. The reduction can be carried out under the conditions similar to those used in the reduction of a compund of the general formula (2c) as in the reaction process formula-3.

Further, among the compound of the general formula (38) used in the reaction process formula-16, a compound having a group of the formula

as the symbol A can be converted into a compound having a group of the formula

as the symbol a, by reducing the former compound.

The reduction can be carried out under the conditions similar to those used in the reduction of a compound of the general formula (2a) as in the reaction process formula-2.

A compound of the general formula (1) of the present invention is also prepared by a method as shown in the following reaction process formula-17.

REACTION PROCESS FORMULA-17

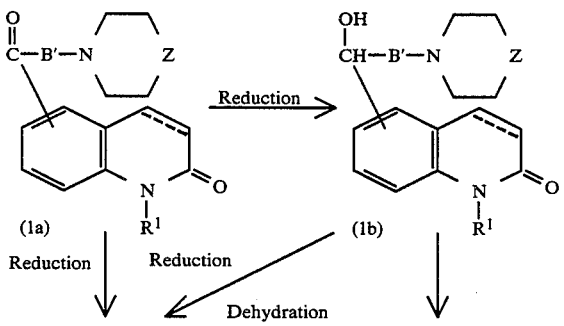

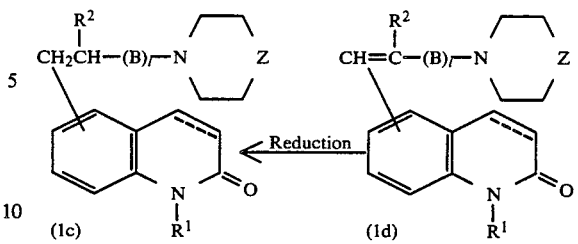

wherein $R^1$, $R^2$, B, B', l, Z, and the carbon-carbon bond between 3- and 4-positions in the carbostyril skeleton are the same as defined previously.

The reduction of a compound of the general formula (1a) is carried out by a method of reduction using a hydrogenating reducing agent, catalytic reduction or the like. In case of applying reduction by using hydrogenating reducing agent, sodium borohydride, lithium aluminium hydroxide or the like, preferably sodium borohydride can be used as the hydrogenating reducing agent. The ratio of the amount of the hydrogenating reducing agent to the amount of a compound of the general formula (1a) is at least an equimolar quantity, preferably 1 to 3 times the molar quantity to the latter. The reduction by using hydrogenating reducing agent is carried out in a suitable solvent such as water a lower alcohol for example, ethanol, ethanol, isopropanol or the like, or an ether for example tetrahydrofuran, diethyl ether or the like, and generally at a temperature of −60° to 50° C., preferably at −30° to a room temperature. The reduction is generally completed in 10 minutes to 3 hours. In case of using litium aluminium hydride as the reducing agent, it is pereferable to use an anhydrous solvent such as diethyl ether, tetrahydrofuran.

In case of applying a method of catalytic reduction, a common catalyst for catalytic reduction such as platinum oxide, palldium black, palladium carbon, Raney nickel or the like is used as the reducing catalyst. The amount of the catalyst to the amount of a compound of the general formula (1a) is generally 0.2 to 0.5 time by weight to the latter. The catalytic reduction is carried out in a solvent for example water, methanol, ethanol, isopropanol, tetrahydrofuran, ethyl ether or the like, and in hydrogen gas stream of generally at 1 to 10 atmospheric pressure, preferably at 1 to 3 atmospheric pressure, under well-shaking condition. Said reduction is carried out generally at −30° to the boiling point of the solvent used, preferably at 0° C. to about room temperature.

When the catalytic reduction is carried out at a lower temperature around 0° to a room temperature by using the hydrogeneating reducing agent, the double bond between 3- and 4-position in the carbostyril skeleton of a compound of the general formula (1a) is not substantially reduced and a corresponding compound of the general formula (1b) wherein the carbonyl group at the end of the side chain being reduced, can mainly be obtained. In said reducing reaction, when a compound having a halogen atoms a lower alkoxycarbonyl group, a lower alkylthio group, a lower alkanoyl group, a nitro group or a cyano group as the substituents on the phehyl ring of the substituted-phenyl group as for the symbol $R^3$ and also having a lower alkenyl group or a lower alkynyl group as for the symbol $R^1$, there are some cases that said substituted groups may be reduced at the same time.

The reaction for obtaining a compound of the general formula (1c) by reducing a compound of the general formula (1d) can be carried out by a method similar to that used in the reaction for obtaining a compound of the general formula (2d) by reducing a compound of the general formula (2c) as in the reaction process formula-3.

The dehydrating reaction of a compound of the general formula (1b) can be carried out by a method similar to that used in the dehydration of a compound of the general formula (10) as in the reaction process formula-3.

The reaction for obtaining a compound of the general formula (1c) by reducing a compound of the general formula (1a), and the reaction for obtaining a compound of the general formula (1c) by reducing a compound of the general formula (1b) can be carried out by the method similar to that used in the reaction for obtaining a compound of the general formula (16) by reducing a compound of the general formula (15) as in the reaction process formula-8.

Among the compound of the general formula (1) of the present invention, a compound having a lower alkyl group, a phenyl-lower alkyl group, a lower alkenyl group or a lower alkynyl goup as for the symbol $R^1$, [that is a compound of the general formula (1f)] can be prepared by reacting a compound having a hydrogen atom as for the symbol $R^1$ (that is a compound of the general formula (1e) with a known compound of the formula (19) as shown in the following reaction process formula-18.

REACTION PROCESS FORMULA-18

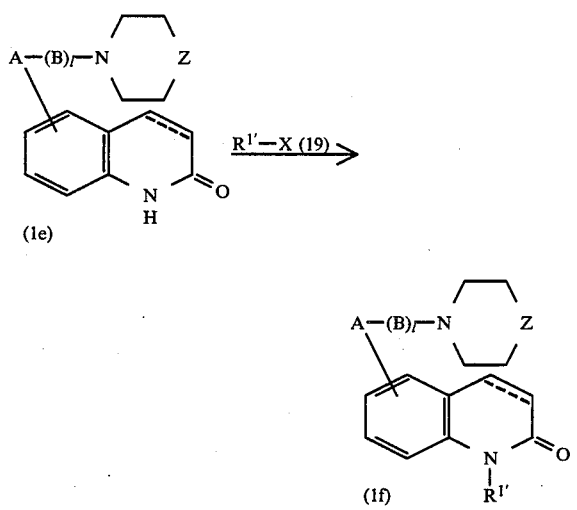

wherein $R^{1'}$ is a loweer alkyl group, a phenyl-lower alkyl, a lower alkenyl group or a lower alkynyl group; A, B, l, Z, X and the carbon-carbon bond between 3- and 4-positions in the carbostyril akeleton are the same as defined previously.

The reaction of a compound of the general formula (1e) with a compound of the general formula (19) may be carried out for example, in the presence of a basic compound in a suitable solvent. As to the basic compound, sodium hydride, potassium metal, sodium metal, sodium amide, potassium amide or the like can be exemplified. As to the solvent, an ether such as dixane, diethylene glycol dimethyl ether, diethyl ether or the like, an aromatic hydrocarbon such as toluene, xylene or the like, dimethylformamide, dimethyl sufoxide, hexamethylphosphoryl triamide or the like can be exemplified. The ratio of the amount of a compound of the general formula (1e) to the amount of a compound of the general formula (19) is not specifically restricted and can be selected from a wide range. Generally, the latter is used at least an equimolar or more, preferably 1 to 2 times the molar quanity to the former. The reaction is generally carried out at 0° to 70° C., preferably 0° to about a room temperature, and is completed in 0.5 to 12 hours. In this reaction, a compound having carboxy group or hydroxyl group as the substituent on the phenyl ring in the substituted-phenyl group, there are some cases that said substituents may be converted into, at the same time, the corresponding ester group or ether group. In such a case, the desired compound can be obtained by hydrolyzing with an acid such as hydrochloric acid or hydrobromic acid under heating condition.

Among the compounds of the general formula (1) of the present invention, a compound having amino group as the substituent on the phenyl ring of the substituted-phenyl group can easily be prepared by reducing a compound having nitro group as the substituent on the phenyl ring of the substituted-phenyl group. This reduction can be carried out by usual conditions in reducing an aromatic nitro group to an aromatic amino group. More specifically, a method by using sodium sulphite or sulfur dioxide as the reducing agent can be applied.

Among the compound of the general formula (1) of the present invention, a compound having carboxy group as the substituent on the phenyl ring of the substitued-phenyl group can easily be prepared by hydrolyzing a compound having a lower alkoxycarbonyl group as the substitutent on the phenyl ring of the substituted-phenyl group. Said hydrolysis may be carried out by usual conditions in hydrolyzing an ester, for example, the hydrolysis may be carried out in the presence of hydrochloric acid, sulfuric acid, sodium hydroxide or the like.

Further, among the compound of the general formula (1) of the present invention, a compound having a single bond between 3- and 4-positions in the carbostyril skeleton and having a substituent or a side chain which is inert to the dehydrogenation, said compound may be converted into the corresponding compound of the formula (1) having a double bond between the 3- and 4-positions of the present invention by dehydrogenizing with a dehydrogenating agent. Alternatively, among the compound of the general formula (1) of the present invention, a compound having a double bond between 3- and 4-positions in the carbostyril skeleton and haing a substituent or a side-chain which is inert to the catalytic reduction, said compound may be converted into the corresponding compound of the formula (1) of the present invention, having a single bond between the 3- and 4-positions by catalytically reducing the said compound.

REACTION PROCESS FORMULA-19

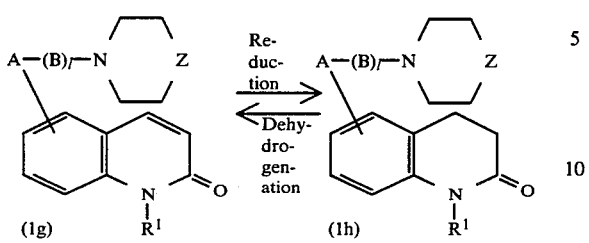

wherein $R^1$, A, B, l and Z are the same as defined previously.

The reduction of a compound of the general formula (1g) can be carried out under conditions simlar to that used in an usual catalytic reduction. As to the catalyst used in this reduction, palladium, palladium-carbon, platinum, Raney nckel or the like is exemplified. Said catalyst may be used in an usual catalytic amount. As to the solvent used in this reduction, methanol, ethanol, isopropanol, dioxane, tetrahydrofuran, hexane, cyclohexane, ethyl acetate or the like can be eemplified. Said reduction can be carried out at a normal pressure or under pressure condition, generally a normal pressure to 10 atmospheric pressure and preferably, a normal pressure to 3 atmospheric pressure. The reduction temperature is generally at 0° to 100° C., preferably at a room temperature to 70° C.

The dehydrogenation of a compound of the general formula (1h) is carried out in a suitable solvent by using an oxidizing agent. As to the oxidizing agent used in this reaction, a benzoquinone such as 2,3-dichloro-5,6-dicyanobenzoquinone, chloranil(2,3,5,6-tetrachlorobenzoquinone) or the like, a halogenating agent such as N-bromosuccinyl imide, N-chlorosuccinyl imide, bromie or the like can be exemplified. As to the ratio of the amount of the oxidizing agent, there is not any restriction thereto and can be selected from a wide range, and generally, 1 to 5 times, preferably 1 to 2 times the molar quantity of the oxidizing agent is used to the amount of a compound of the general formula (1h). As to the solvent used in this reaction, an ether such as dioxane, tetrahydrofuran, methoxyethanol, dimethoxyethane, an aromatic hydrocarbon such as benzene, toluene, xylene, Tetraline, (a trademark for 1,2,3,4-tetrahydronaphthalene), cumene or the like, a halogenated hydrocarbon such as dichloromethane, dichloroethan, chloroform, carbontetrachloride, or the like, an alcohol such as butanol, amyl alcohol, hexanol, a polar protic solvent such as acetic acid, a polar aprotic solvent such as dimethylformamide, dimethyl sulfoxide, hexamethylphosphoryl triamide or the like can be exemplified. The reaction is generally carried out at a room temperature to 300° C., preferably at a room temperature to 200° C., and is completed in generally in 1 to 40 hours.

Among the compound of the general formula (1), of the present invention, a compound having a hydrogen atom as for the symbol $R^1$ and also having a double bond between 3- and 4-positions in the carbostyril skeleton capable of exisiting in tautomeric system in the form of lactim-lactam as shown in the following reaction formula-20.

REACTION PROCESS FORMULA-20

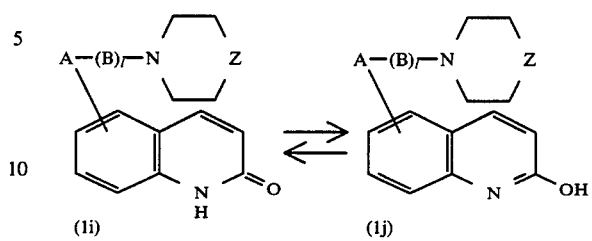

wherein A, B, l and Z are the same as defined previously.

REACTION PROCESS FORMULA-21

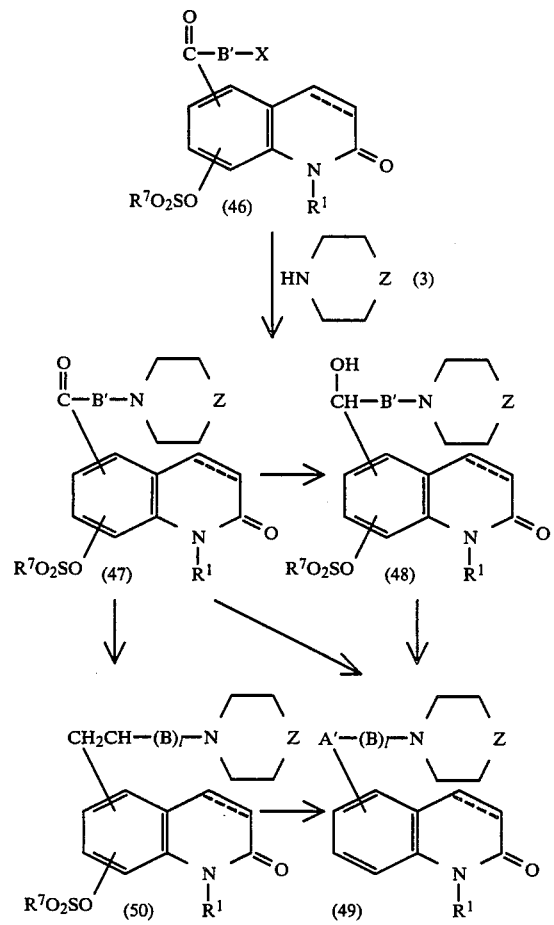

wherein $R^1$, $R^2$, $R^7$, B, B', l, Z and the carbon-carbon bond between 3- and 4-positions in the carbostyril skeleton are the same as defined previously; and A' is a group of the formula

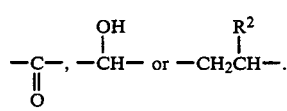

The reaction of a compound of the general formula (46) with a compound of the general formula (3) may be carried out by a method similar to that used in the reaction of a compound of the general formula (2) with a compound of the general formula (3) in the reaction process formula-1.

The reaction of a compound of the general formula (47) to a compound of the general formula (48) can be carried out by a method similar to that used in the reaction of a compound of the general formula (2a) to a compound of the general formula (2b) in the reaction process formula-2. The reaction of a compound of the general formula (47) to a compound of the general formula (50) can be carried out a method similar to that used in the reaction of a compound of the general formula (11) to a compound of the general formula (2d) in the reaction process formula-6. The respective reactions of compounds of the general formulas (47), (48) and (50) to a compound of the general formula (49) can be carried out by using conditions for reducing a compound of the general formula (42) as in the reaction process formula-2a. A compound of the general formula (47) can also be prepared by sulfonylating a precoursor compound of the formula,

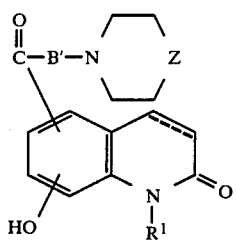

wherein $R^1$, B' and Z and carbon-carbon bond between 3- and 4-positions in the carbostyril skeleton are the same as defined previously, with a compound of the general formula (9) by a method similar to that used in the sulfonylation of a compund of the general formula (45) with a compound of the eneral formula (9) as in the reaction process formula-2b.

Among the compounds of the general formula (1) of the present invention, a compound represented by the general formula (1k) can be prepared by reaction process formula-22 as follows:

REACTION PROCESS FORMULA-22

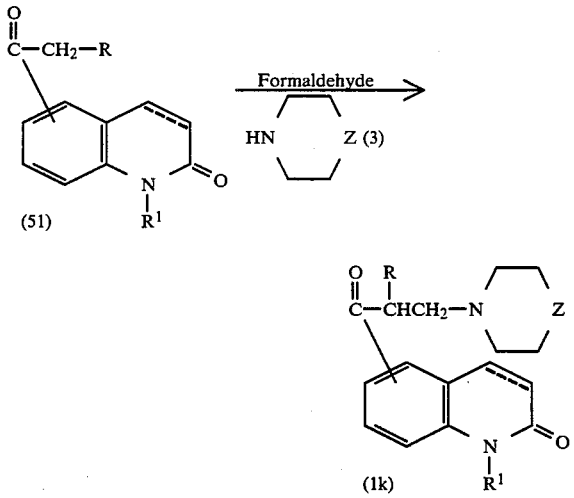

wherein R is a hydrogen atom or a lower alkyl group; $R^1$, Z and the carbon-carbon bond between 3- and 4-positions in the carbostyril skeleton are the same as defined previously.

A compound of the general formula (51) used as the starting material includes known or novel compounds and is prepared by reaction process formulas-2 [reaction of a compound of the general formula (4) with a compound of the general formula (5) or (6)]; -2a; -2b; -9 [reaction of a compound of the general formula (18) with a compound of the general formula (19)]; and -10. Thus a compound to be used as the starting material or the reactant is a compound having a hydrogen atom instead of a group of the symbol X or acetyloxy group.

The reaction of a compound of the general formula (51) with a compound of the general formula (3) can be carried out by using reaction conditions in Mannich reaction. The reaction is carried out in a suitable solvent at a room temperature to 150° C., preferably at 50° to 100° C. for 1–10 hours.

As to the solvent used in this reaction is exemplified as a lower alcohol such as methanol, ethanol, propanol or the like; an ether such as dioxane, tetrahydrofuran or the like; an aliphatic acid such as acetic acid, propionic acid or the like; dimethyl sulfoxide or dimethylformamide or the like.

As to the formaldehyde used in this reaction is exemplified as formalin, paraformaldehyde, trioxane or the like. The ratio of the amount of the formaldehyde and a compound of the general formula (3) to the amount of a compound of the general formula (51) is not specifically restricted and can be selected from a wide range and generally the former is used at least in an equimolar quantity, preferably 1 to 3 times the molar quantity to the latter.

In reaction process formulas-2a or -2b, among compounds of the general formula (2a') or (2a"), those having hydrogen atom as for the symbol X and having halogen atom(s) at α-position in the group of the formula

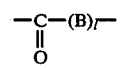

can be prepared by reacting a compound of the general formula (2a''') (wherein the symbol X is a hydrogen atom) with a halogenating agent in a suitable solvent.

As to the solvent used in this reaction, dichloromethane, chloroform, carbon tetrachloride, benzene, acetic acid and the like can be exemplified.

As to the halogenating agent used in this reaction, N-bromosuccinyl imide, N-chlorosuccinyl imide, chlorine, bromine or the like can be exemplified.

The ratio of the amount of the halogenating agent to the amount of a compound of the general formula (2a''') is generally an equimolar quantity, preferably, an excess amount.

The reaction is carried out at a room temperature to 200° C., preferably at a room temperature to 150° C., the reaction may be completed in 6 minutes to 6 hours.

Among the compounds of the general formula (1) in the present invention, compounds having acidic group can easily be converted into their salts by reacting with pharmaceutically acceptable basic compounds. The examples of such basic compounds include sodium hydroxide, potassium hydroxide, calcium hydroxide, sodium carbonate, potassium hydrogencarbonate and the like.

Further, among the compounds of the general formula (1) in the present invention, compounds having basic group can easily be converted into their acid-addition salts by reacting with phamaceutically acceptable acids. The examples of such acids include inorganic acids such as hydrochloric acid, sulfuric acid, phosphoric acid, hydrobromic acid and the like; organic acids such as oxalic acid, maleic acid, fumaric acid, malic acid, tartaric acid, citric acid, benzoic acid and the like.

The desired compounds as prepared by the procedures in the above-mentioned various reaction process formulas can easily be isolated and purified by the usual separation means such as solvent extraction, dilution, recrystallizatioln, column chromatography, preparative thin-layer chromatography.

Compounds of the present invention also including their optical isomers.

As for antihistaminic agents compounds of the general formula (1) can be used in the form of pharmaceutical composition together with usual pharmaceutically acceptable carriers. The examples of the carriers which are used depending on the desired form of pharmaceutical composition including diluents or excipient such as fillers, diluents, binders, wetting agents, disintegrators, surface-active agents, lubricants.

No particular restriction is made to the administration unit forms and the compounds can be selected in any desired unit from as antihistaminic agents and typical unit form including tablets, pills, powders, liquors, suspensions, emulsions, granules, capsules, suppositories, injections (solution and suspensions) and ointments. For the purpose of to shape in the form of tablets, carriers which are widely used in this field can also be used, for example excipients such as lactose, sucrose, sodium chloride, solution of glucose, urea, starch, calcium carbonate, caolin, crystalline cellulose, silicic acid; binding agents such as water, ethanol, propanol, simple syrup, glucose, starch solution, gelation solution, carboxymethyl cellulose, shelac, methyl cellulose, calcium phosphate and polyvinylpyrrolidone; desintegrators such as dried starch, sodium alginate, agar-agar powder, laminalia powder, sodium hydrogencarbonate, calcium carbonate, Tweens, sodium laurylsulfate, monoglyceride of stearic acid, starch, lactose; desintegration inhibitor such as sucrose, stearin, coconut butter, hydrogenated oil; absorption accelerator such as quaternary ammonium base; sodium laurylsulfate; wetting agent such as glycerin of starch; adsorbing agents such as starch, lactose, caoline, bentonite, colloidal silicic acid; lubricants such as purified talc, stearic acid salt, boric acid powder, Macrogol, solid polyethylene glycol. In case of tablets, they can be further coated with the usual coating materials to make sugar coated tablets, gelatin film coated tablets, tablets coated with enteric coatings, tablets coated with films or double layered tablets and multi-layered tablets.

For the purpose of to shape in the form of pills, carriers which a known and widely used in this field can also be used, for example, excipients such as glucose, lactose, starch, coconut butter, hydrogenated vegetable oils, caolin and talc; binders such as powdered Gumi Arabicum, powdered Tragacanth, gelatin and ethanol; desintegrators such laminaria and agaragar are included.

For the purpose of to shape in the form of suppositories, carriers which are known and widely used in this field can also be used, for example, polythylene glycols, coconut butter, higher alcohols, esters of higher alcohols, gelatin and semi-synthesized glycerids are included.

For the purpose of to make in the form of injection preparations, solutions and suspensions are sterilized and are preferably isotonic to blood. In making injection preparations, every carriers which are commonly used in this field can also be used, for example, water, ethyl alcohol, propylene glycol, ethoxylated isostearyl alcohol, polyoxylated isostearyl alcohol, polyoxyethylene sorbitol, sorbritane esters are included. In these instances, adequate amounts of sodium chloride, glucose or glycerin can be added to contain in the desired preparations for the purpose of to have them isotonic. Furthermore, the usual dissolving agents, buffers, analgesic agents, preservitives can be added as well as coloring materials, preservitives, perfums, seansoning agents, sweetening agents and other medicines can also be added into the desired preparations if necessary.

For the purpose of to make preparations in the form of pastes and creams, diluents which are known and widely used in this field can also be used, for example, white vaceline, paraffin, glycerin, cellulose derivatives, polyethylene glycols, silicones and bentonite are included.

The amount of compounds of the general formula (1) or their acid addition salts to be contained in antihistaminic agents is not especially restricted and it can suitably be selected from wide range, but usually 1 to 70% by weight of the whole composition is preferable.

The above-mentioned antihistaminic agents and central nervous system controlling agents can be used in various forms depending on the purpose without any restriction. For example, tablets, pills, solutions, suspensions, emulsions, granules and capsules are administered orally; and injection preparations are administered intreavenously singly or are mixed with injection transfusions such as glucose solutions and amino acid solutiolns; if necessary, the injection preparations are administered singly intramuscularly, intracutaneously, subcutaneously or intraperitoneally. Suppositories are administered into rectum and ointments are administered by coating.

The dosage of the present antihistaminic agents is suitably selected accoding to the usage, purpose and conditions of symptoms and usually pharmaceutical composition containing 40 μg-2 mg/kg. day of the compound of the general formula (1) or its acid addition salt may be administered 3-4 times a day.

EXAMPLE OF PREPARATION OF TABLETS-1

By using an usual procedure, tablets having the following formulation were prepared.

| | |
|---|---|
| 6-{1-Oxo-4-(4-phenyl-1-piperazinyl)butyl}-3,4-dihydrocarbostyril | 10 mg |
| Corn starch | 127 mg |
| Magnesium stearate | 18 mg |
| Lactose | 45 mg |
| Total | 200 mg |

EXAMPLE OF PREPARATIONS OF TABLETS-2

By using a usual procedure, tablets having the following formulation were prepared.

| | |
|---|---|
| 6-{1-Oxo-4-[4-2-chloro- | 5 mg |

| | | |
|---|---|---|
| phenyl)-1-piperazinyl]butyl}-3,4-dihydrocarbostyril | | |
| Corn starch | 132 mg | |
| Magnesium stearate | 18 mg | |
| Lactose | 45 mg | |
| Total | 200 mg | |

EXAMPLE OF PREPARATION OF TABLETS-3

By using a usual procedure, tablets having the following formulation were prepared.

| | |
|---|---|
| 6-[1-Hydroxy-4-(4-phenyl-1-piperaziny)butyl]-3,4-dihydrocarbostyril | 5 mg |
| Corn starch | 132 mg |
| Magnesium stearate | 18 mg |
| Lactose | 45 mg |
| Total | 200 mg |

EXAMPLE OF PREPARTION OF TABLES-4

By using a usual procedure, tablets having the following formulation were prepared.

| | |
|---|---|
| 6-{4-(4-Phenyl-1-piperzinyl)butyl}-3,4-dihydrocarbosatyril | 10 mg |
| Corn starch | 127 mg |
| Magnesium stearate | 18 mg |
| Lactose | 45 mg |
| Total | 200 mg |

EXAMPLE OF PREPARATION OF TABLETS-5

By using a usual procedure, tablets having the following formulation were prepared.

| | |
|---|---|
| 6-{4-[4-(2-Chlorophenyl)-1-piperaziny]-1-propenyl}-3,4-dihydrocarbostyril | 5 mg |
| Corn starch | 132 mg |
| Magnesium stearate | 18 mg |
| Lactose | 45 mg |
| Total | 200 mg |

EXAMPLE OF PREPARATION OF TABLETS-6

By using a usual procedure, tablets having the following formulation were prepared.

| | |
|---|---|
| 6-[1-Oxo-4-(4-phenyl-4-hydroxy-1-piperidyl]-3,4-dihydrocarbostyril | 10 mg |
| Corn starch | 127 mg |
| Magnesium stearate | 18 mg |
| Lactose | 45 mg |
| Total | 200 mg |

EXAMPLE OF PREPARATION OF TABLETS-7

By using a usual procedure, tablets having the following formulation were prepared.

| | |
|---|---|
| 6-[1-Hydroxy-3-(4-benzyl-1-piperidyl)propyl]-3,4- | 5 mg |
| dihydrocarbostyril | |
| Corn starch | 132 mg |
| Magnesium stearate | 18 mg |
| Lactose | 45 mg |
| Total | 200 mg |

Each compounds represented by the general formula (1) in the present invention has low toxicity and can advantageously be used as an active ingredient in a pharmaceutical composition.

Pharmacological activities of compounds of the general formula (1) in the present invention were determined by test methods as explained below with the following results.

Compounds used in the tests are as follows:

COMPOUNDS OF THE PRESENT INVENTION (NOS. 1–32)

| Compound No. | Name of the compound |
|---|---|
| 1 | 6-[1-Oxo-3-(4-phenyl-1-piperazinyl)propyl]-3,4-dihydrocarbostyril |
| 2 | 6-[1-Oxo-4-(4-phenyl-1-piperazinyl)butyl]-3,4-dihydrocarbostyril.monohydrochloride |
| 3 | 6-{1-Oxo-4-[4-(2-chlorophenyl)-1-piperazinyl]butyl}-3,4-dihydrocarbostyril.-monohydrochloride.monohydrate |
| 4 | 6-{1-Oxo-2-[4-(3-chlorophenyl)-1-piperazinyl]butyl}-carbostyril |
| 5 | 6-{1-Hydroxy-4-[4-(3-chlorophenyl)-1-piperazinyl]butyl}-3,4-dihydrocarbostyril |
| 6 | 6-{1-Hydroxy-3-[4-(2,3-dimethylphenyl)-1-piperazinyl]-propyl}-3,4-dihydrocarbostryril |
| 7 | 6-{1-Oxo-3-[4-(3-chlorophenyl)-1-piperazinyl]-propyl}-3,4-dihydrocarbostyril.monohydrochloride |
| 8 | 6-{3-[4-(3-Chlorophenyl)-1-piperazinyl]-1-propenyl}-3,4-dihydrocarbostyril |
| 9 | 6-{3-[4-(2-Ethoxyphenyl)-1-piperazinyl]-1-propenyl}-3,4-dihydrocarbostyril |
| 10 | 6-{3-[4-(3-Methylphenyl)-1-piperazinyl]-1-propenyl}-3,4-dihydrocarbostyril |
| 11 | 6-[4-(4-Phenyl-1-piperazinyl)-1-butenyl]-3,4-dihydrocarbostyril |
| 12 | 6-{4-[4-(2-Ethoxyphenyl)-1-piperazinyl]-1-butenyl}-3,4-dihydrocarbostyril |
| 13 | 6-{3-[4-(4-chlorophenyl)-1-piperazinyl]-1-propenyl}-3,4-dihydrocarbostyril |
| 14 | 6-{4-[4-(2-Chlorophenyl)-1-piperazinyl]-butyl}-3,4-dihydrocarbostyril |
| 15 | 6-{4-[4-(2-Ethoxyphenyl)-1-piperazinyl]-butyl}-3,4-dihydrocarbostyril |
| 16 | 6-{3-[4-(2-Ethoxyphenyl)-1-piperazinyl]-propyl}-3,4-dihydrocarbostyril |
| 17 | 6-{3-[4-(2-Methoxyphenyl)-1-piperazinyl]-propyl}-3,4-dihydrocarbostyril |
| 18 | 6-[3-(4-Phenyl-1-piperazinyl)propyl]-3,4-dihydrocarbostyril |
| 19 | 6-{3-[4-(2-Methoxyphenyl)-1-piperazinyl]-1-piperazinyl}-1-propenyl}-3,4-dihydrocarbostyril |
| 20 | 1-Methyl-6-[1-oxo-3-(4-phenyl-1-piperazinyl)propyl]-3,4-dihydrocarbostyril.-monooxalate |
| 21 | 1-Benzyl-6-{3-[4-(3-methylphenyl)-1-piperazinyl]-1-propenyl}-3,4-dihydrocarbostyril monooxalate |
| 22 | 5-[3-(4-Phenyl-1-piperazinyl)propyl]-3,4-dihydrocarbostyril |
| 23 | 6-{3-[4-(4-Methylphenyl)-1,2,5,6-tetrahydropyridyl]-1-propenyl}-3,4-dihydrocarbostyril |
| 24 | 6-[1-Oxo-3-(4-benzyl-1-piperidylpropyl]-3,4-dihydrocarbostyril |
| 25 | 6-{1-Oxo-4-[4-(4-chlorophenyl)-1,2,5,6- |

-continued

| Compound No. | Name of the compound |
|---|---|
|  | tetrahydropyridyl]butyl}-3,4-dihydrocarbostiryl |
| 26 | 6-{1-Oxo-3-[4-(4-methylphenyl)-1,2,5,6-tetrahydropyridyl]propyl}-3,4-dihydrocarbostiryl |
| 27 | 6-{3-[4-(2-Methoxyphenyl)-1,2,5,6-tetrahydropyridyl]-1-propenyl}-3,4-dihydrocarbostyril monooxalate |
| 28 | 6-[1-Oxo-4-(4-phenyl-1,2,5,6-tetrahydropyridyl)butyl]-3,4-dihydrocarbostyril |
| 29 | 6-{3-[4-(2-Methoxyphenyl)-1-piperidyl]propyl}-3,4-dihydrocarbostyril monooxalate |
| 30 | 6-[4-(4-Phenyl-1-piperazinyl)butyl]-carbostyril |
| 31 | 6-{4-[4-(2-Ethoxyphenyl)-1-piperazinyl]-1-butenyl}carbostyril |
| 32 | 6-{1-Hydroxy-2-[4-(3-chlorophenyl)-1-piperazinyl]butyl}carbostyril |

REFERENCE COMPOUND

Chloropromazine[2-chloro-N,N-dimethyl-10H-phenothiazine-10-propanamine] was used as the reference compound.

(A) Halothane anesthesia increasing activity

Male mice of ddy-strain a having about 20 g body weight were used. One test group consists of 10 mice. An aqueous Gummi Arabicum suspension of test compound (80 mg of a compound to be tested and 1 g of Gummi Arabicum/100 ml of physiological NaCl solution) was administered orally to each mouse at the dosage of 16 mg of test compound/kg body. One hour after the administration, each mouse was placed in gas respiration chamber (13×13×24 cm) and oxygen gas containing 4% of Halothane[2-brome-2-chloro-1,1,1-trifluoroethane] was flown into the chamber at the velocity of 2/min for 3 minutes. A mouse anaesthetized was taken out from the chamber and the time between the introduction of anesthesia to waking was measured by righting reflex as the index. To mice of control group, 1% Gummi Arabicum aqueous physiological solution was orally administered at the dosage of 0.1 ml/kg body. [Reference: M. J. Turnbull and J. W. Watkins: Br. J. Pharmacol., 58, 27–35 (1976)].

The results are shown in Table 1.

TABLE 1

| Compound No. | Time (minutes) |
|---|---|
| 1 | 13.3 |
| 2 | 11.5 |
| 3 | 8.0 |
| 4 | 9.7 |
| 5 | 13.0 |
| 6 | 8.2 |

(B) Activity for inhibiting jumping behavior in mouse induced by Methamphetamine and L-DOPA Individual male mice of ddy-strain having a body weight of 17 to 25 g were used. The mice were were not fed for 24 hours. One test group consisted of 6 mice. A compound to be tested was administered orally. 40 Minutes after the administration 4 mg/kg of Methamphetamine d-N-α-dimethylphenthylamine was intraperitonerally administered, further 15 minutes after the administration of Methamphetamine, 400 mg/kg of L-DOPA was intraperitonerally administered. 60 Minutes after the administration of L-DOPA, [3-(3,4-dihydroxyphenyl)alanine] the mouse was placed in a glass beaker of 2 liters capacity, and the number of jumping of the mouse was recorded. The activity for inhibiting jumping behavior of the test compound was determined as positive in case of number of jumping performed by the administered mouse counted 10 or less. While, the activity for inhibiting jumping behabior of the test compound was determined as negative in case the number of jumping performed by the administered mouse recorded over 10. The effective dosage ($ED_{50}$ value: mg/kg) of the test compound which gives 3 mice were positive over 6 mice of one test group was calculated. The number of jumping performed by the mouse being administered with physiological saline solution as the reference was 150 to 200 per hour. [Cf. H. Lal, F. C. Colpaert, P. Laduron: European J. Pharmacol., 30, 113–116 (1975)]

The results are shown in Table 2.

TABLE 2

| Compound No. | $ED_{50}$ value (mg/kg) |
|---|---|
| 1 | 1.35 |
| 2 | 1.52 |
| 3 | 1.05 |
| 4 | 4.05 |
| 5 | 1.95 |
| 7 | 1.34 |
| 8 | 1.02 |
| 9 | 0.12 |
| 10 | 6.02 |
| 11 | 1.60 |
| 12 | 0.056 |
| 13 | 4.16 |
| 14 | 3.23 |
| 15 | 0.39 |
| 16 | 0.24 |
| 18 | 0.34 |
| 19 | 0.79 |
| 25 | 9.56 |
| 26 | 10.32 |
| 27 | 1.25 |
| 28 | 8.89 |
| 29 | 2.01 |
| 30 | 0.56 |
| 31 | 0.14 |
| 32 | 4.86 |
| Chlorpromazine | 7.60 |

(C) Activity for antagonizing epinephrine in mouse

Individual male mice of ddy strain having 17 to 20 g of body weight were used. The mice were abstained from eating for 24 hours. One test group consist of 10 mice. A compound to be tested was administered orally. One hour after the administration, 40 mg/kg of epinephrine was intraperitonerally administered. The number of mice survived 24 hours after the administration of epinephrine and the deaths were recorded and the dose of the test compound which would allow half the animals to survive was calculated ($ED_{50}$ value: mg/kg). All of 10 mice administered physiological saline solution as the reference group were dead within a few minutes after the administration of epinephrine. [Cf. Loew, E. R. and Micetich, A., J. Pharmacol. Exp. Ther., 93, 434–443 (1948)]

The results are shown in Table 3.

| Compound No. | $ED_{50}$ value (mg/kg) |
|---|---|
| 1 | 3.03 |
| 2 | 4.02 |
| 3 | 6.12 |
| 9 | 0.005 |

-continued

| Compound No. | ED₅₀ value (mg/kg) |
| --- | --- |
| 11 | 4 to 8 |
| 12 | 0.005 |
| 15 | 0.71 |
| 16 | 0.02 |
| 17 | 0.29 |
| 18 | 0.21 |
| 19 | 0.1 |
| Chlorpromazine | 10.6 |

(D) Activity of palpebral ptosis test in mouse

Individual male mice of ddy-strain having 18 to 20 g of body weight were used. The mice were abstained from eating for 24 hours. One test group consist of 10 mice. Compound to be tested was administered orally in the dosage of 64 mg/kg. One hour after the administration, the state of palpebral ptosis of the mouse were observed and evaluated on the basis of the following score system. The mean value was calculated from the scores of 10 mice. [C. J. E. Niemegeers and P. A. J. Janssen: Arzheim.Forsch. (Drug Res.), 24, (1), pp-45–52 (1974)]

| Score | Degree of palpebral ptosis |
| --- | --- |
| 8 | Eyes completely closed. |
| 6 | Eyes slightly opened. |
| 4 | Half open eyes. |
| 2 | Eyes slightly closed. |
| 0 | Wide open eyes. |

The results are shown in Table 4.

TABLE 4

| Compound No. | Score obtained (Mean value) |
| --- | --- |
| 1 | 1.67 |
| 2 | 4.5 |
| 3 | 2.0 |
| 4 | 2.33 |
| 7 | 1.33 |

(E) Antihistaminic activity test

As to the test method for determining antihistaminic activity of a compound in vitro, a method of using an enucleated ileum of a guinea pig is generally accepted. Antihistaminic activity of the present compounds was conduted according to said method as follows:

A male guinea pig having 300 to 500 g body weight was killed by blood letting. An ileum having length of 15 cm being enucleated from the ileocecal region was dipped into Tyrode's solution (which was prepared from 8.0 g of NaCl, 0.2 g of KCl, 0.2 g of CaCl₂, 1.0 g of glucose, 1.0 g of NaHCO₃, 0.065 g of NaHPO₄.2H₂O and 0.2135 g of MgCl₂.6H₂O make 1000 ml in total volume by adding water). Then the tissue of ileum was cut to a length of 2.5 to 3.0 cm and suspended in an organ bath filled with 30 ml of Tyrode's solution. The organ bath was kept a temperature of 36° C. and blowing a mixed gas consisting of 5% of $CO_2$ and 95% of $O_2$ into the bath. 10 Minutes after the blowing, 10-6M of histamine was added to the bath to examine the sensitivity of the tissue and a reaction curve (control) with respect to the dosage of histamine was obtained. After the dosage of histamine-reaction curve (control) become constant $10^{-6}$ g/ml of a compound to be tested was added to the bath and further histamine was added 5 minutes later to obtain dosage-reaction curve. Retraction of the isotonic was recorded on a pen-recorder through an isotonic transducer [TD-112S manufactured by Nihon Koden]. Antihistaminic activity of the test compound was determined as $pA_2$ value by "Van Rossam" method [J. M. Van Rossam: Arch. Inst. Pharmacodyn. Ther., 143, 299 (1963)] in terms of that the maximum retraction of ileum caused by histamine shown in the control curve is 100%. The results are shown in Table 5.

TABLE 5

| Compound No. | pA₂ |
| --- | --- |
| 20 | 7.58 |
| 21 | 7.31 |
| 22 | 7.01 |
| 23 | 7.81 |
| 24 | 7.23 |

(F) Acute toxicity test

Each of the following compound of the general formula in the present invention was administered orally to male rats to determine the acute toxicity (LD₅₀ mg/kg). The results are shown in Table 6.

TABLE 6

| Compound No. | Acute toxicity (LD₅₀ mg/kg) | Compound No. | Acute toxicity (LD₅₀ mg/kg) |
| --- | --- | --- | --- |
| 1 | 500 | 17 | 500 |
| 2 | 500 | 18 | 500 |
| 3 | 500 | 19 | 500 |
| 4 | 500 | 20 | 500 |
| 5 | 500 | 21 | 500 |
| 6 | 500 | 22 | 500 |
| 7 | 500 | 23 | 500 |
| 8 | 500 | 24 | 500 |
| 9 | 500 | 25 | 500 |
| 10 | 500 | 26 | 500 |
| 11 | 500 | 27 | 500 |
| 12 | 500 | 28 | 500 |
| 13 | 500 | 29 | 500 |
| 14 | 500 | 30 | 500 |
| 15 | 500 | 31 | 500 |
| 16 | 500 | 32 | 500 |

The present invention will be illustrated more in specifically by way of the following examples, in which the preparation of the compounds to be used for the starting materials will be shown as Reference Examples and the preparation of the objective compounds will be shown as Examples.

REFERENCE EXAMPLE 1

120 Milliliters of γ-chlorobutyryl chloride and 160 g of pulverized anhydrous aluminium chloride were suspended in 300 ml of carbon disulfide. The suspension was refluxed by heating and another suspension of 29.4 g of 3,4-dihydrocarbostyril in 100 ml of carbon disulfide was added dropwise to the firt suspension in 1 hour and the reaction was continued for 4 hours under refluxing condition by heating. After the reaction was completed, the reaction mixture was poured into ice-water and the precipitates thus formed were collected by filtration, washed with water and with ether. Then the washed precipitates were recrystallized from acetone to obtain 25.5 g of 6-(4-chloro-1-oxobutyl)-3,4-dihydrocarbostyril in yellow needle-like crystals. Melting point: 158°–160° C.

REFERENCE EXAMPLE 2

By a method similar to that described in Reference Example 1, there is obtained 6-chloroacetylcarbostyril in colorless needle-like crystals. Melting point 233°–234° C. (from methanol-chloroform).

REFERENCE EXAMPLE 3

By a method similar to that described in Reference Example 1, there was obtained 1-methyl-6-(β-chloropropionyl)-3,4-dihydrocarboxtyril in colorless needle-like crystals. Melting point: 121°–123° C. (from isopropanol).

REFERENCE EXAMPLE 4

2.0 Grams of 6-(1-oxo-4-chlorobutyl)-3,4-dihydrocarbostyril was mixed with 100 ml of methanol, and the mixture was stirred at a room temperatue. Then 1.0 g of sodium borohydride was added to the mixture gradually. After the reaction mixture was stirred at a room temperature for 2 hours, methanol was removed by distillation under a reduced pressure. The residue was extracted with chloroform and the chloroform layer was washed with water, and dried. Chloroform was removed by distillation under a reduced pressure, then the residue thus obtained was recrystallized from ethanol-water to obtain 1.2 g of 6-(1-hydroxy-4-chlorobutyl)-3,4-dihydrocarbostyril in colorless needle-like crystals. Melting point: 120°–121° C.

REFERENCE EXAMPLE 5

4.0 Grams of 6-(4-chloro-1-oxobutyl)-3,4-dihydrocarbostyril was disposed in 200 ml of methanol, and the suspension was stirred at a room temperature. Then 2.0 g of sodium borohydride was added to the suspension gradually and the reaction was continued for 1 hour. Next, 3 ml of concentrated hydrochloric acid was added to the reaction mixture and the mixture was concentrated under a reduce pressure with heat-refluxing condition to obtain a residue. The residue was extracted with chloroform and the chloroform layer was washed with water and dried. Then colorform was removed by distillation under a reduced pressure to obtain a residue, and the residue was recrystallized from ethanol to obtain 2.4 g of 6-(4-chloro-1-butenyl)-3,4-dihydrocarbostyril in yellow needle-like crystals. Melting point: 153°–155° C.

REFERENCE EXAMPLE 6

14.4 Grams of 3,4-dihydrocarbostyril and 10 g of γ-butyrolacton were mixed into 120 g of polyphosphoric acid and stirred at 80°–90° C. for 10 hours. The reaction mixture was poured into 300 ml of ice-water and was allowed to stand overnight. Then the precipitates thus formed were collected by filtration and washed with water, then recrystallized from ethanol-ethyl acetate to obtain 9.5 g of 6-(4-hydroxy-1-oxobutyl)-3,4-dihydrocarbostyril, having the melting point of 175°–176° C. in colorless prism-like crystals. Next, 5 g of 6-(4-hydroxy-1-oxobutyl)-3,4-dihydrocarbostyril and 0.5 g of palladium black wre mixed in 160 ml of ethanol and the mixture was subjected to catalytic reduction under 3 kg/cm² of hydrogen gas at 60° C. for 6 hours. The reaction mixture was then cool and was added 1 ml of concentrated hydrochloric acid thereinto. Further the reaction mixture was subjected to the catalytic reduction under 3 kg/cm² of hydrogen gas for 6 hours. The reaction mixture was filtered and the mother liquor was concentrated under a reduced pressure. The residue was recrystallized from ligroin to obtain 3.2 g of 6-(4-hydroxybutyl)-3,4-dihydrocarboxtryril, having the melting point of 133°–134° C. Next, 3.2 g of 6-(4-hydroxybutyl)-3,4-dihydrocarbostyril and 5 ml of thionyl chloride were mixed into 50 ml of chloroform and the mixture was stirred at a room temperature for 24 hours. The reaction mixture was concentrated under a reduced pressure. The residue was then recrystallized from ligroin to obtain 1.8 g of 6-(4-chlorobutyl)-3,4-dihydrocarbostryl, having the melting point of 119°–121° C., in colorless prism-like crystals.

REFERENCE EXAMPLE 7

2.8 Grams of 6-(4-chloro-1-butenyl)-3,4-dihydrocarbostryil and 2.1 g of sodium iodide were mixed into 40 ml of dimethylformamide and the mixture was stirred at 50° C. for 1 hour. Then into the reaction mixture was added 2.0 g of morpholine and 2.0 ml of triethylamine and was stirred at 50° C. for 1 hours. The reaction mixture was concentrated under a reduced pressure to obtain a residue and 50 ml of 5%-sodium hydrogencarbonate aqueous solution was added therein and stirred. Next, the insoluble matters formed in the mixture were collected by filtration, and were washed with water and then recrystallized from ethanol to obtain 2.2 g of 6-(4-morpholino-1-butenyl)-3,4-dihydrocarbostyril, having the melting point of 136°–139° C. in colorless needle-like crystals. Next, 2.2 g of 6-(4-morpholino-1-butenyl)-3,4-dihydrocarbostyril and 0.2 g of platinum balck were mixed into 100 ml of ethanol and was subjected to catalytic reductin under 3 kg/cm² of hydrogen gas at a room temperature for 5 hours. The reaction mixture was filtered and the mother liquor was concentrated under a reduced pressure to obtain a residue. The residue was recrystallized from ligroinbenzene to obtain 1.8 g of 6-(4-morpholinobutyl)-3,4-dihydrocarbostyril, in colorless flake-like crystals. Melting point: 130°–132° C.

REFERENCE EXAMPLE 8

2.3 Grams of 6-(3-chloro-1-propenyl)-3,4-dihydrocarbostyril, 2.0 g of 4-benzylpiperazine and 2.0 ml of triethylamine were mixed in 50 ml of dimethylformamide and the mixture was stirred at 50° C. for 3 hours. The reaction mixture was poured into a mixture of 50 ml of a sturated sodium chloride aqueous solution with 50 ml of 5% of sodium hydrogencarbonate aqueous solution, and the organic layer was extracted with chloroform. The coloroform layer was washed with water and dried, then chloroform was removed by distillation to obtain a residue. The residue was recrystallized from ethanol-water to obtain 2.1 g of 6-[3-(4-benzylpiperazinyl)-1-propenyl]-3,4-dihydrocarbostyril, having the melting point of 151°–153° C. in colorless needle-like crystals. Then 2.1 g of 6-[3-(4-benzylpiperazinyl)-1-propenyl]-3,4-dihydrocarboxtyril, 0.2 g of platinum balck and 2 ml of concentrated hydrochloric acid were mixed with 100 ml of ethanol and the mixture was subjected to catalytic reductin under 3 kg/cm² of hydrogen gas at a room temperature for 5 hours. The reaction mixture was filtered and the mother liquor was concentrated to obtain a residue. The residue was recrystallized from methanol to obtain 1.8 g of 6-(3-piperzinopropyl)-3,4-dihydrocarbostyril dihydrochloride in colorless needle like crystals. Melting point: 275°–278° C. (decomposed).

REFERENCE EXAMPLE 9

2.5 Grams of 6-(4-chloro-1-butenyl)-3,4-dihydrocarbostyril and 2.3 g of DDQ (2,3-dichloro-5,6-dicyanobenzoquinone) were mixed in 160 ml of dioxane and the mixture was refluxed by heating for 6 hours. Further, 1.1 of DDQ was added to the reaction mixture and the mixture was refluxed by heating for 3 hours. The reaction mixture was cooled and the precipitates thus formed were removed by filtration and the mother liquor was concentrated under a reduced pressure to obtain a residue. The residue was dissolved in a mixture of 100 ml of chloroform with 5 ml of methanol and the solution was padded through a silica gel column for removing the unreacted DDQ. The residue was recrystallized from methanol to obtain 1.6 g of 6-(4-chloro-1-butenyl)carbostyril in yellow needle-like crystals. Melting point: 215°-128° C.

REFERENCE EXAMPLE 10

20 Grams of 6-($\beta$-chloropropionyloxy)-3,4-dihydrocarbostyril, 60 g of pulverized anhydrous aluminium chloride, 6 g of sodium chloride and 6 g of potassium chloride were mixed together and the mixture was melted by heating and stirred at 150°-170° C. for 1 hour. The reaction mixture was poured into ice-water and allowed stand overnight to obtain crystalline precipitates. The precipitates were collected by filtration, washed with water and dried, then recrystallized from methanol to obtain 12 g of 6-hydroxy-7-(3-chloropropionyl)-3,4-dihydrocarbostyril in white crystals. Melting point: 205°-208° C.

Elemental analysis for $C_{12}H_{12}O_3N$ Cl (253.69): Calculated C:56.82, H:4.77, N:5.52, Found C:56.98, H:4.51, N:5.44.

REFERENCE EXAMPLE 11

5.06 Grams of 6-hydroxy-7-(3-chloropropionyl)-3,4-dihydrocarbostyril and 1.8 g of anhydrous pyridine were mixed with 50 ml of dimethylformamide. Then the mixture was cooled with ice and 2.5 g of methanesulfonyl chloride was added to the mixture and stirred at a room temperature for 3 hours. The reactin mixture was poured into 100 ml of a saturated sodium chloride solution and extracted with chloroform. The chloroform layer was washed with water, dried and chloroform was removed by distillation under a reduced pressure to obtain a residue. The residue was crystallized by adding 80 ml of hexane to obtain crude crystals. The crude materials were collected by filtration and were recrystallized from ethanol to obtain 4.5 g of 6-methylsulfonyloxy-7-(3-chloropropionyl)-3,4-dihydrocarbostyril in white crystals.

Elemental analysis for $C_{13}H_{14}O_5S$ N Cl (331.78): Calculated C:47.06, H:4.25, N:4.22, Found C:47.33, H:4.02, N:4..19.

REFERENCE EXAMPLE 12

3.0 Grams of 6-methylsulfonyloxy-7-(3-chloropropionyl)-3,4-dihydrocarbostyril and 0.5 g of palladium black were suspended in 200 ml of ethanol and the suspension was subjected to catalytic reduction under 3 atmospheric pressure of hydrogen gas at a room temperature for 5 hours under stirring condition. The reaction mixture was filtered and the mother liquor was concentrated under a reduced pressure to obtain a residue. The residue was recrystallized from ethanol to obtain 1.2 g of 7-(3-chloropropionyl)-3,4-dihydrocarbostyril in colorless powdery-like crystals. Melting point: 159°-161° C.

Elemental analysis for $C_{12}H_{12}O_2N$ Cl (237.69): Calculated C:60.64, H:5.09, N:5.89, Found C:B 60.59, H:5.24, N:5.91.

REFERENCE EXAMPLE 13

3.3 Grams of 6-methylsulfornyloxy-7-(3-chloropropionyl)-3,4-dihydrocarbostyril and 1.5 g of sodium iodide were suspended in 30 ml of acetone and the mixture was stirred at 40°-50° C. for 2 hours. Then 30 ml of dimethylformamide was added to the mixture and acetone was removed by distillation under a reduced pressure. Next, 1.8 g of 4-phenylpiperidine and 1.5 ml of triethylamine were added to the mixture and stirred at 60°-70° C. for 7 hours. The reaction mixture was poured into 150 ml of a saturated sodium chloride aqueous solution and extracted with chloroform and the chloroform layer was ashed with water and dried and chloroform was removed by distillation under a reduced pressure to obtain a residue. The residue was crystallized with hexane and recrystallized from ethanol-ligroin to obtain 1.2 g of 6-methylsulfonyloxy-7-[1-oxo-3-(4-phenyl-1-piperidyl)propyl]-3,4-dihydrocarbostyril in white crystals.

Elemental analysis for $C_{24}H_{28}O_5N_2S$ (M.W. 456.56): Calculated C:63.14, H:6.18, N:6.14, Found C:63.07, H:6.19, N:6.12.

REFERENCE EXAMPLE 14

(a) 2.5 Grams of 6-hydroxy-7-(3-chloropropionyl)-3,4-dihydrocarbostyril and 1.8 g of sodium iodide were mixed with 30 ml of acetone and the mixture was stirred at 50° C. for 1 hour. Then 30 ml of dimethylformamide was added to the mixture and acetone was removed by distillation under a reduced pressure. Next, 3.0 ml of triethylamine and 2.0 g of 4-phenylpiperidine were added to the mixture and stirred at 60°-70° C. for 5 hours. The reaction mixture was concentrated under a reduced pressure to obtain a residue. The residue was crystallized with a 5% sodium hydrogencarbonate aqueous solution to obtain crude crystgals. The crude crystals were recrysgtallized from methanol to obtain 1.6 g of 6-hydroxy-7-[1-oxo-3-(4-phenylpiperidyl)propyl]-3,4-dihydrocarbostyril in amorphous-like crystals. Melting point: 240°-245° C.

Elemental analysis for $C_{23}H_{26}O_3N_2$ (M.W. 462.52): Calculated C:77.90, H:5.67, N:6.06, Found C:77.51, H:5.81, N:6.12.

(b) 2.3 Grams of 6-hydroxy-7-[3-(4-phenylpiridyl)-1-oxopropyl]-3,4-dihydrocarbostyril, 0.4 g of potassium hydroxide were suspended in 80 ml of methanol and the suspension was stirred at a room temperature for 2 hours. The reaction mixture was concentrated under a reduced pressure to obtain residue. Then the residue was dispersed in 40 ml of dimethylformamide and 0.7 g of methanesulfonyl chloride was added into the dispersion and stirred at a room temperature for 3 hours. The reaction mixture was treated by a procedure similar to that used in Reference Example 13 mentioned above to obtain 1.2 g of 6-methanesulfonyloxy-7-[1-oxo-3-(4-phenylpiperidyl)propyl]3,4-dihydrocarbostyril in crystals.

| Elemental analysis for $C_{24}H_{28}N_2O_5F$ (M.W. 460.40) | | | |
|---|---|---|---|
| | C | H | N |
| Calculated (%): | 67.91 | 6.65 | 6.60 |

| Elemental analysis for C₂₄H₂₈N₂O₅F (M.W. 460.40) | | | |
|---|---|---|---|
| | C | H | N |
| Found (%): | 67.88 | 6.69 | 6.55 |

REFERENCE EXAMPLE 15

(a) 26.8 Grams of 8-methoxy-5-(3-chloropropionyl)-3,4-dihydrocarbostyril and 16.5 g of sodium iodide were dissolved in 200 ml of dimethylformamide and the mixture was stirred at 40° C. for 1 hour. Then 11.1 g triethyl amine and 17.1 g of 4-phenylpiperazine were added to the mixture and stirred at 40° C. for 2 hours additionally. The reaction mixture was concentrted under a reduced pressure to obtain a residue. Then a 5%-sodium hydrogencarbonate aquous solution and ether were added to the residue to obtain crystalline presipitates. The precipitates were collected by filtration and were recrystallized from ethanol to obtain 8-methoxy-5-[1-oxo-3-(4-phenyl-1-piperazinyl)propyl]-3,4-dihydrocarbostyril.

Yield: 27.5 g.

ElementaL analysis for C₂₃H₂₇O₃N₃ (M.W. 393.48): Calculated C:70.21, H:6.92, N:10.68, Found C:70.00, H:6.99, N:10.48.

(b) To 19.7 g of methoxy-5-[1-oxo-3-(4-phenyl-1-piperazinyl)propyl]-3,4-dihydrocarbostyril was added 300 ml of 47%-hydrobromic acid and the mixture was refluxed for 18 hours. The reaction mixture was concentrated under a reduced pressure to dryness. Then to the residue thus obtained was added water and again concentrated under a reduced pressure to dryness. Acetone was added to the crystalline residue and collected by filtration and were recrystallize from methanol. The crystals were suspended in 500 ml of water and the suspension was neutralized with 5%-sodium hydroxide aqueous solution and crystalline precipitates thus formed were collected by filtration and were washed with water. 17.1 Grams of 8-hydroxy-5-[1-oxo-3-(4-phenyl-1-piperazinyl)propyl]-3,4-dihydrocarbostyril was obtained in amorphous-like crystals. Melting point: 287°-291° C.

Elemental analysis for C₂₂H₂₅O₃N₃ (M.W. 379.46): Calculated C:69.64, H:6.64, N:11.07, Found C:69.54, H:6.45, N:11.01.

REFERENCE EXAMPLE 16

37.9 Grams of 8-hydroxy-5-[1-oxo-3-(4-phenyl-piperazinyl)propyl]-3,4-dihydrocarbostyril and 5.9 g of potassium hydroxide were dissolved in 400 ml of water and the solution was concentrated under a reduced pressure to obtain a residue. The residue was dissolved in 400 ml of dimethylformamide and then 12.0 g of methane-sulfonyl chloride was added dropwise to the solution under cooling condition. One hour after the addition either was added to the reaction mixture to obtain crystals. The crystals were collected by filtration and washed with acetone, then recrystallized from isopropanol to obtain 35.9 g of 8-methanesulfonyl-5-[1-oxo-3-(4-phenyl-1-piperazinyl)propyl]-3,4-dihydrocarbostyril in light brown needle-like crystal. Melting point: 165°-167° C.

Elemental analysis for C₂₃H₂₇O₅N₃S (M.W. 457.55): Calculated C:60.38, H:5.95, N:9.18, Found C:60.19, H:6.01, N:9.15.

REFERENCE EXAMPLE 17

By a method similar to that described in Example 10, by using 6-acetyloxy-3,4-dihydroccarbostyril as the starting material, there was prepared 6-hydroxy-7-acetyl-3,4-dihydrocarbostyril.

REFERENCE EXAMPLE 18

By a method similar to that described in Example 11, by using 6-hydroxy-7-acetyl-3,4-dihydrocarbostyril as the starting material, there was prepared 6-methylsulfonyloxy-7-acetyl-3,4-dihydrocarbostyril.

REFERENCE EXAMPLE 19

By a method similar to that described in Example 12, by using 6-methylsulfonyloxy-7-acetyl-3,4-dihydrocarbostyril, there was prepared 7-acetyl-3,4-dihydrocarbostyril.

REFERENCE EXAMPLE 20

9.45 Grams of 7-acetyl-3,4-dihydrocarbostyril was dissolved in 30 ml of glacial acetic acid with stirring at 20° C., then a mixture of 2.6 ml of bromine with 10 ml of glacial acetic acid was added dropwise at a room temperature for 30 minutes with stirring. The reaction mixture was ice-cooled to precipitate crystals, and recrystalized from 50%-ethanol aqueous solution to obtain 7-α-bromoacetyl-3,4-dihydrocarbostyril.

Yield: 9.4 g. Melting point: 202°-203° C. Colorless needle-like crystals

| Elemental analysis for C₁₁H₁₀NO₂Br (M.W. 268.11) | | | |
|---|---|---|---|
| | C | H | N |
| Calculated (%): | 49.28 | 3.76 | 5.22 |
| Found (%): | 49.24 | 3.79 | 5.18 |

EXAMPLE 1

5.0 Grams of 6-(1-oxo-4-chlorobutyl)-3,4-dihydrocarbostyril and 3.5 g of sodium iodine were mixed in 100 ml of acetone and the mixture was stirred at 40°-50° C. for 5 hours. Then 80 ml of dimethylformamide was added to the mixture and acetone was removed from the mixture by distillation under reduced pressure. To this reaction mixture, 5.0 g of 4-phenylpiperazine and 5 g of triethylamine were added and stirred at 70°-80° C. for 6 hours. The reaction mixture was concentrated under a reduced pressure and 50 ml of 5%-sodium hydrogencarbonate solution was stirred to effect crystallization. Crude crystals thus formed were collected by filtration and washed with water and dried. Then the dried crude crystals were dispersed in 80 ml of chloroform and stirred at a room temperature for 1 hour. Insoluble matters in the chloroform solution were removed from the solution and chloroform was removed by distillation to obtain the residue. To the residue thus obtained was added 50 ml of methanol and 10 ml of concentrated hydrochloric acid and mixture was concentrated under a reduced pressure to dryness. To the residue thus obtained was added 50 ml of acetone and stirred to obtain crude crystals. The crude crystals were collected by filtration and washed with acetone and recrystallized from ethanol-water to obtain 5.7 g of 6-[1-oxo-4-(4-phenyl-1-piperazinyl)butyl]-3,4-dihydrocarbostyril monohydrochloride in yellowish powdery crystals.

Melting point: 195°-196° C.

| Elemental analysis for $C_{23}H_{28}O_2N_3Cl$ | | | |
|---|---|---|---|
| | C | H | N |
| Calculated (%): | 66.74 | 6.82 | 10.15 |
| Found (%): | 66.83 | 6.60 | 10.23 |

By a method similar to that used in Example 1 and by using a suitable starting material, there were obtained compounds of Examples 2–5 as follows:

EXAMPLE 2

6-{1-Oxo-3-[4-(3-chlorophenyl)-1-piperazinyl]-propyl}-3,4-dihydrocarbostyril monohydrochloride Colorless needle-like crystals (from ethanol-water)
Melting point: 233°–234° C. (decomposed)

EXAMPLE 3

6-{1-Oxo-4-[4-(2-chlorophenyl)-1-piperazinyl]-butyl}-3,4-dihydrocarbostyril monohydrochloride. monohydrate Colorless needle-like crystals (from water)
Melting point: 266°–268° C. (decomposed)

EXAMPLE 4

6-{1-Oxo-4-[4-(2-ethoxyphenyl)-1-piperazinyl]-butyl}-3,4-dihydrocarbostyril monohydrochloride Colorless needle-like crystals (from ethanol-water)
Melting point: 240°–241° C. (decomposed)

EXAMPLE 5

6-{1-Oxo-3-[4-(4-methylphenyl)-1-piperazinyl]-propyl}-3,4-dihydrocarbostyril monohydrochloride Light yellowish needle-like crystals (from ethanol-water)
Melting point: 224°–226° C.

EXAMPLE 6

2.4 Grams of 6-(1-oxo-3-chloropropyl)-3,4-dihydrocarbostyril and 1.6 g of sodium iodide were mixed with 60 ml of isopropanol and the mixture was stirred at 40°–50° C. for 2 hours. Then to this reaction mixture were added 2.0 g of 4-phenylpiperazine and 3.0 g of DBU (1,5-diazabicyclko[5,4,0]undecane-5) and refluxed by heating for 6 hours. Then the reaction mixture was poured into 100 ml of 5%-sodium hydrogen-carbonate solution and stirred at a room temperature foir 1 hour. The insoluble matters were collected by filtration, washed with water and dried, then recrystallized from ethanol-chloroform to obtain 1.9 g of 6-[1-oxo-3-(4-phenylpiperazinyl)-propyl]-3,4-dihydrocarbostyril in colorless flake-like crystals.
Melting point: 196°–197° C.

| Elemental analysis for $C_{22}H_{25}O_2N_3$ | | | |
|---|---|---|---|
| | C | H | N |
| Calculated (%): | 72.70 | 6.93 | 11.56 |
| Found (%): | 72.52 | 7.08 | 11.81 |

By a method similar to that described in Example 6 by using a suitable starting material, there were obtained compounds of Examples 7–10 as follows:

EXAMPLE 7

6-{1-Oxo-3-[4-(2-fluorophenyl)-1-piperazinyl]-propyl}-3,4-dihydrocarbostyril

Colorless powdery crystals (from dimethylformamide-water)
Melting point: 200°–201° C.

EXAMPLE 8

6-{1-Oxo-4-[4-(4-bromophenyl)-1-piperazinyl]-butyl}-3,4-dihydrocarbostyril

Colorless needle-like crystals (from ethanol-water)
Melting point: 184°–185° C.

EXAMPLE 9

6-{1-Oxo-4-[4-(4-nitrophenyl)-1-piperazinyl]-butyl}-3,4-dihydrocarbostyril

Yellowish needle-like crystals (from dimethylformamide-water)
Melting point: 255°–256° C. (decomposed).

EXAMPLE 10

6-{1-Oxo-4-[4-(ethoxycarbonylphenyl)-1-piperazinyl]-butyl}-3,4-dihydrocarbostyril Colorless needle-like crystals (from ethanol)
Melting point: 191°–192° C.

EXAMPLE 11

2.4 Grams of 6-(1-oxo-3-chloropropyl)-3,4-dihydrocarbostyril and 4.5 g of 4-(2,3-dimethylphenyl)-piperazine were mixed with 80 ml of xylene and the mixture was refluxed by heating for 24 hours. Then the reaction mixture was concentrated under a reduced pressure to dryness. Thus obtained solid matter was dissolved in 100 ml of chloroform, the chloroform layer was washed with 5%-sodium hydrogencarbonate aqueous solution twice and washed with water twice then dried with anhydrous sodium sulfate, and chloroform was removed by distillation to obtain the residue. To the residue thus obtained was added ether-hexane and the insoluble matters were collected by filtration and recrystallized from concentrated hydrochloric acid-ethanol-water to obtain 2.6 g of 6-{1-oxo-3-[4-(2,3-dimethylphenyl)-1-piperazinyl]-propyl}-3,4-dihydrocarbostyril monohydrochloride in cololress needle-like crystals.
Melting point: 273°–274° C. (decomposed)

| Elemental analysis for $C_{24}H_{30}O_2N_3Cl$ | | | |
|---|---|---|---|
| | C | H | N |
| Calculated (%): | 67.35 | 7.07 | 9.82 |
| Found (%): | 67.36 | 6.95 | 9.80 |

EXAMPLE 12

By a method similar to that described in Example 11, there is obtained 6-{1-Oxo-4-[4-(3,5-dichlorophenyl)-1-piperazinyl]butyl}-3,4-dihydrocarbostyril.
Colorless needle-like crystals (from isopropanol)
Melting point: 194°–195° C.

EXAMPLE 13

3.0 of 6-(1-oxo-2-bromoethyl)-3,4-dihydrocarbostyril and 5.5 g of 4-(3-chlorophenyl)piperazine were dispersed in 50 ml of dioxane and the dispersion was stirred at 50° C. for 5 hours. Then the reaction mixture was cooled and the insoluble matters formed in the reaction mixture were removed and the dioxane mother liquor was concentrated under a reduced pressure to dryness. 80 Milliliter of ether was added to the dried matter to effect the crystallization. Crude crystals thus obtained were recrystallized from dioxane-water to obtain 3.1 g of 6-{1-oxo-2-[4-(3-chlorophenyl)-1-piperazinyl]ethyl}-3,4-dihydrocarbostyril in light yellow needle-like crystals.

Melting point: 214°-215° C.

| Elemental analysis for $C_{21}H_{22}O_2N_3Cl$ | | | |
|---|---|---|---|
| | C | H | N |
| Calculated (%): | 65.71 | 5.78 | 10.95 |
| Found (%): | 65.96 | 5.61 | 10.81 |

By a method similar to that described in Example 13, by using a suitable starting material, there were obtained compounds of Examples 14–16 as follows:

EXAMPLE 14

6-{1-Oxo-2-[4-(2,3-dimethylphenyl)-1-piperazinyl]-ethyl}carbostyril

Colorless needle-like crystals (from methanol-chloroform)
Melting point: 199°-200° C. (decomposed).

EXAMPLE 15

6-{1-Oxo-2-[4-(3-chlorophenyl)-1-piperazinyl]butyl}carbostyril monohydrochloride Colorless needle-like crystals (from isopropanol)
Melting point: 209°-210° C. (decomposed).

EXAMPLE 16

6-{1-Oxo-2-[4-(3-chlorophenyl)-1-piperazinyl]butyl}-3,4-dihydrocarbostyril monooxalate Colorless needle-like crystals (from isopropanol)
Melting point: 135°-136° C.

EXAMPLE 17

5.0 Grams of 6-(1-oxo-4-chlorobutyl)-3,4-dihydrocarbostyril and 7.5 g of sodium iodide were dispersed in 120 ml of anhydrous dimethylformamide and the mixture was stirred at 50°-60° C. for 2 hours. To this reaction mixture were added 10 g of 4-(3-chlorophenyl)piperazine and 5 ml of triethylamine and was stirred at 50°-60° C. for 6 hours, then stirred at a room temperature for 24 hours. The reaction mixture was concentrated under a reduced pressure to obtain a residue. To the residue thus obtained was added 80 ml of 5%-sodium hydrogencarbonate solution and the organic layer was extracted with chloroform. The chloroform layer was washed with water, dried and chloroform was removed by distillation. The residue thus obtained was crystallized with ehter to obtain crude crystals and the crude crystals were recrystallized from ethanol to obtain 6.5 g of 6-{1-oxo-4-[4-(3-chlorophenyl)-1-piperazinyl]butyl}-3,4-dihydrocarbostyril in colorless needle-like crystals.

Melting point: 158°-159° C.

| Elemental analysis for $C_{23}H_{25}O_2N_3Cl$ | | | |
|---|---|---|---|
| | C | H | N |
| Calculated (%): | 67.06 | 6.36 | 10.20 |
| Found (%): | 66.98 | 6.40 | 10.20 |

By a method similar to that described in Example 17, by using a suitale starting material, there were obtained compounds of Examples 18–26 as follows:

EXAMPLE 18

6-{1-Oxo-4-[4-(4-methylphenyl)-1-piperazinyl]butyl}-3,4-dihydrocarbostyril

Light yellow needle-like crystals (from ethanol)
Melting point: 200°-201° C.

EXAMPLE 19

6-{1-Oxo-4-[4-(3,4,5-trimethoxyphenyl)-1-piperazinyl]-butyl}-3,4-dihydrocarbostyril dihydrochloride Colorless powdery crystals (from methanol-water)
Melting point: 261°-263° C. (decomposed)

EXAMPLE 20

6-{1-Oxo-3-[4-(4-cyanophenyl)-1-piperazinyl]-propyl}-3,4-dihydrocarbostiryl

Colorless plate-like crystals (from ethanol)
Melting point: 206°-207° C.

EXAMPLE 21

6-{1-Oxo-4-[4-acetylphenyl)-1-piperazinyl]butyl}-3,4-dihydrocarbostyril

Yellow needle-like crystals (from dimethyl-formamide-water)
Melting point: 218°-219° C.

EXAMPLE 22

6-{1-Oxo-4-[4-methylthiophenyl)-1-piperazinyl]butyl}-3,4-dihydrocarbostyril

Light yellowish needle-like crystals (from ethanol)
Melting point: 187°-188° C.

EXAMPLE 23

6-{1-Oxo-3-[4-(2-methoxyphenyl)-1-piperazinyl]-propyl}-3,4-dihydrocarbostyril monohydrochloride Light yellow needle-like crystals (from dioxane-water)
Melting point: 212°-212.5° C.

EXAMPLE 24

6-{1-Oxo-4-[4-(4-carboxyphenyl)-1-piperazinyl]butyl}-3,4-dihydrocarbostyril monohydrochloride Colorless powdery crystals (from ethanol)
Melting point: 264°-265° C.

EXAMPLE 25

6-{1-Oxo-4-[4-hydroxyphenyl)-1-piperazinyl]butyl}-3,4-dihydrocarbostyril

Colorless powdery crystals (from ethanol)
Melting point: 192°-194° C.

EXAMPLE 26

6-{1-Oxo-2-[4-(4-nitrophenyl)-1-piperazinyl]butyl}-3,4-dihydrocarbostyril

Yellow powdery crystals (from ethanol)
Melting point: 239°–242° C.

By a method similar to that described in Example 17, there were obtained the following compounds:

5-[1-Oxo-3-(4-phenyl-1-piperazinyl)propyl]-3,4-dihydrocarbostyril

Colorless needle-like crystals (from ethanol-methanol)
Melting point: 180°–182° C.

5-{1-Oxo-3-[4-(2-ethoxyphenyl)-1-piperazinyl]propyl}-3,4-dihydrocarbostyril

White crystals (from methanol-water)
Melting point: 223°–235° C. (decomposed)

5-{1-Oxo-3-[4-(2-hydroxyphenyl)-1-piperazinyl]propyl}-3,4-dihydrocarbostyril

5-{1-Oxo-3-[4-(4-n-butylphenyl)-1-piperazinyl]propyl}-3,4-dihydrocarbostyril monohydrochloride Colorless needle-like crystals (from ethanol-water)
Melting point: 218°–222° C.

5-{1-Oxo-3-[4-(2-chlorophenyl)-1-piperazinyl]-propyl}-3,4-dihyrocarbostyril

5-{1-Oxo-3-[4-(2,3-dimethyl)-1-piperazinyl]propyl}-3,4-dihydrocarbostyril monohydrochloride White crystals (from methanol-water)
Melting point: 231°–234° C.

6-[1-Oxo-3-(4-benzyl-1-piperazinyl)propyl]-3,4-dihydrocarbostyril

Colorless needle-like crystals (from ethanol-water)
Melting point: 177°–178° C.

6-{1-Oxo-3-[4-(1-tetralinyl)-1-piperazinyl]propyl}-3,4-dihydrocarbostyril

Colorless prism-like crystals (friom ethanol-water)
Melting point: 187°–188° C.

5-[1-Oxo-2-(4-phenyl-1-piperazinyl)ethyl]-3,4-dihydrocarbostyril

Colorless needle-like crystals (from methanol)
Melting point: 195°–198° C. (decomposed).

EXAMPLE 27

2.6 Grams of 1-methyl-6-(1-oxo-3-chloropropyl)-3,4-dihydrocarbostyril, 1.2 g of pyridine and 2.0 g of 4-phenylpiperazine were mixed into 30 ml of dimethylformamide and the mixture was stirred at 70°–80° C. for 7 hours. The reaction mixture was poured into 100 ml of 5%-sodium hydrogencarbonate solution and was extracted with chloroform. The chloroform layer was washed with water, dried and chloroform was removed by distillation. The residue thus obtained was dissolved with acetone and the pH of the solution was adjusted to pH 4 by adding 5%-oxalic acid acetone solution to form crystalline precipitates. The precipitates were collected by filtration and recrystallized from ethanol-water to obtain 2.8 g of 1-methyl-6-[1-oxo-3-(4-phenyl-1-piperazinyl)propyl]-3,4-dihydrocarbostyril monooxalate in colorless flake-like crystals.

Melting point: 164°–165° C.

| Elemental analysis for $C_{23}H_{27}O_2N_3(COOH)_2$ | | | |
|---|---|---|---|
| | C | H | N |
| Calculated (%): | 64.33 | 6.25 | 8.99 |
| Found (%): | 64.48 | 6.12 | 9.03 |

By a method similar to that described in Example 27, by using a suitable starting materials, there were obtained compounds of Examples 28–30 as follows:

EXAMPLE 28

1-Hexyl-6-[1-oxo-3-(4-phenyl-1-piperazinyl)propyl]-3,4-dihydrocarbostyril monooxalate Colorless flake-like crystals (from ethanol-water)
Melting point: 142°–144° C.

EXAMPLE 29

1-Benzyl-6-[1-oxo-3-(4-phenyl-1-piperazinyl)propyl]-3,4-dihydrocarbostyril monooxalate Colorless needle-like crystals (from ethanol-water)
Melting point: 171°–172° C.

EXAMPLE 30

1-Allyl-6-[1-oxo-3-(4-phenyl-1-piperazinyl)propyl]-3,4-dihydrocarbostyril monooxalate Colorless flake-like crystals (from ethanol-water)
Melting point: 169°–170° C.

EXAMPLE 31

2.7 Grams of 6-(1-oxo-4-chlorobutyl)-3,4-dihydrocarbostyril and 1.5 g of sodium iodide were mixed in 30 ml of dimethyl sulfoxide and the mixture was stirred at 50° C. for 2 hours. Then to the reaction mixture were added 2.0 g of 4-(3,4-methylenedioxyphenyl)piperazine and 3 g of DBU and the reaction mixture was stirred at 70°–80° C. for 5 hours. After the reaction was completed, the reaction mixture was poured into 10 ml of 2%-sodium hydrogencarbonate and the organic layer was extracted with chloroform. The chloroform layer was washed with water, dried and chloroform was removed by distillation. To the residue thus obtained were added 50 ml of methanol and 5 ml of concentrated hydrochloric acid and the mixture was concentrated under a reduced pressure to dryness. The residue thus obtained was crystallized by adding ethanol-acetone to obtain crude crystals, and the crude crystals were recrystallized from ethanol-water. 2.1 Grams of 6-{1-oxo-4-[4-(3,4-methylenedioxy-phenyl)-1-piperazinyl]butyl}-3,4-dihydrocarbostyril monohydrochloride in colorless powdery crystals were obtained.

Melting point: 246°–248° C. (decomposed)

| Elemental analysis for $C_{24}H_{27}O_4N_3 \cdot HCl$ | | | |
|---|---|---|---|
| | C | H | N |
| Calculated (%): | 62.95 | 6.16 | 9.18 |
| Found (%): | 63.12 | 6.01 | 9.25 |

EXAMPLE 32

1.8 Grams of 6-[1-oxo-3-(4-phenyl-1-piperazinyl)propyl]-3,4-dihydrocarbostyril and 0.24 g of of sodium hydride (50% in mineral oil) were mixed in 50 ml of dimethylformamide and stirred at a room temperature for 3 hours. Then 0.9 g of p-toluenesulfonic acid was added and stirred at a room temperature for 3 hours. The reaction mixture was poured into 150 ml of a saturated sodium chloride solution and was extracted with chloroform. The chloroform layer was washed with water, dried and chloroform was removed by distillation under a reduce pressure. The residue thus obtained was injected into preparative thin-layer chromatography to purify and separate the desired compound. The compound obtained was dissolved in acetone and converted into the oxalate by a method similar to that described in Example 27 and recrystallized from ethanol-water to obtain 1.5 g of 1-methyl-6-[1-oxo-3-(4-phenyl-1-piperazinyl)propyl]-3,4-dihydrocarbostyril.monooxalate in colorless flake-like crystals.

Melting point: 164°–165° C.

| Elemental analysis for $C_{23}H_{27}O_2N_3(COOH)_2$ | | | |
|---|---|---|---|
| | C | H | N |
| Calculated (%): | 64.22 | 6.25 | 8.99 |
| Found (%): | 64.02 | 6.41 | 9.08 |

By a method similar to that described in Exmaple 32, by using a suitable starting material, there were obtained compounds of Examples 33–36 as follows:

EXAMPLE 33

1-Benzyl-6-[1-oxo-3-(4-phenyl-1-piperazinyl)propyl]-3,4-dihydrocrabostyril monooxalate Colorless needle-like crystals (from ethanol-water)
Melting point: 171°–172° C.

EXAMPLE 34

1-Allyl-6-[1-ox-3-(4-phenyl-1-piperazinyl)propyl]-3,4-dihydrocarbostyril monoxalate Colorless flake-like crystals (from ethanol-water)
Melting point: 169°–170° C.

EXAMPLE 35

1-Methyl-6-[1-hydroxy-3-(4-phenyl-1-piperazinyl)propyl]-3,4-dihydrocarbostyril monooxalate Colorless flake-like crystals (from ethanol-water)
Melting point: 155°–156° C.

EXAMPLE 36

1-Benzyl-6-[1-hydroxy-3-(4-phenyl-1-piperazinyl)propyl]-3,4-dihydrocarbostyril monoxalate Colorless needle-like crystals (from ethanol-water)
Melting point: 161°–162° C.

EXAMPLE 37

2.8 Grams of 6-(1-hydroxy-4-chlorobutyl)-3,4-dihydrocarbostyril and 1.8 g of sodium iodide were mixed in 60 ml of dimethylformamide and the mixture was stirred at a room temperture for 7 hours. To the reaction mixture were added 2 g of triethylamine and 2.5 g of 4-phenylpiperazine and stirred at a room temperature for 24 hours. The reaction mixture was poured into 200 ml of 1%-sodium hydrogencarbonate aqueous solution and was extracted with chloroform. The chloroform layer was washed with water, dried and chloroform was removed by distillation under a reduced pressure. The obtained residue was recrystallized from isopropanol to obtain 2.5 g of 6-[1-hydroxy-4-(4-phenyl-1-piperazinyl)butyl]-3,4-dihydrocarbostyril.

Colorless needle-like crystals
Melting point: 167°–168° C.

| Elemental analysis for $C_{23}H_{29}O_2N_3$ | | | |
|---|---|---|---|
| | C | H | N |
| Calculated (%): | 72.79 | 7.70 | 11.07 |
| Found (%): | 73.01 | 7.59 | 11.21 |

By a method similar to that described in Example 37, by using a suitable starting material, there were obtained compounds of Examples 38–48 as follows:

EXAMPLE 38

.6-[1-Hydroxy-b 3-(4-phenyl-1-piperazinyl)propyl]-3,4-dihydrocarbostyril

Colorless needle-like crystals (from isopropanol)
Melting point: 147°–148° C.

EXAMPLE 39

6-{1-Hydroxy-4-[4-(2-chlorophenyl)-1-piperazinyl]-butyl}-3,4-dihydrocarbostyril

Colorless needle-like crystals (from isopropanol)
Melting point: 163°–164° C.

EXAMPLE 40

6-{1-Hydroxy-3-[4-(2-methoxyphenyl)-1-piperazinyl]-propyl}-3,4-dihydrocarbostyril Colorless needle-like crystals (from isopropanol)
Melting point: 145°–147° C.

EXAMPLE 41

6-{1-Hydroxy-3-[4-(2,3-dimethylphenyl)-1-piperazinyl]-propyl}-3,4-dihydrocarbostyril Colorless needle-like crystals (from ethanol)
Melting point: 173°–175° C. (decomposed)

EXAMPLE 42

6-{1-Hydroxy-3-[4-(4-methylphenyl)-1-piperazinyl]-propyl}-3,4-dihydrocarbostyril Colorless needle-like crystals (from isopropanol)
Melting point: 171°–172° C.

EXAMPLE 43

6-{1-Hydroxy-4-[4-(3-chlorophenyl)-1-piperazinyl]-butyl}-3,4-dihydrocarbostyril

Colorless needle-like crystals (from chloroform-ether)
Melting point: 156.5°–157° C.

EXAMPLE 44

6-{1-Hydroxy-2-[4-(3-chlorophenyl)-1-piperazinyl]-butyl}-3,4-dihydrocarbostyril

Colorless flake-like crystals (from ethanol-chloroform)
Melting point: 215°–216° C.

EXAMPLE 45

6-{1-Hydroxy-2-[4-(3-chlorophenyl)-1-piperazinyl]-butyl}carbostyril

Colorless needle-like crystals (from isopropanol-chloroform)
Melting point: 243°–244° C. (decomposed)

EXAMPLE 46

6-{1-Hydroxy-2-[4-(2,3-dimethylphenyl)-1-piperazinyl]ethyl}carbostyril

Colorless needle-like crystals (from isopropanol-chloroform)
Melting point: 245°–246° C. (decomposed)

EXAMPLE 47

1-Methyl-6-[1-hydroxy-3-(4-phenyl-1-piperazinyl)-propyl]-3,4-dihydrocarbostyril monooxalate Colorless flake-like crystals (from ethanol-water)
Melting point: 155°–156° C.

EXAMPLE 48

1-Benzyl-6-[1-hydroxy-3-(4-phenyl-1-piperazinyl)-propyl]-3,4-dihydrocarbostyril monooxalate Colorless needle-like crystals (from ethanol-water)
Melting point: 161°–162° C.

5-[1-Hydroxy-3-(4-phenyl-1-piperazinyl)propyl]-3,4-dihydrocarbostyril

Colorless needle-like crystals (from ethanol)
Melting point: 158°–160° C.

EXAMPLE 49

2.0 Grams of 6-[1-oxo-4-(4-phenylpiperazinyl)-butyl]-3,4-dihydrocarbostyril and 0.5 g of palladium black were dispersed in 80 ml of water and stirred at a room temperature under 2 atmospheric pressure of hydrogen gas for 5 hours. The reaction mixture was filtered for removing the palladium black and the mother liquor was concentrated under a reduced pressure and the residue thus obtained was crystallized from acetone and a small amount of ethanol. The crude crystals thus obtained were collected by filtration and recrystallized from isopropanol to obtain 1.5 g of 6-[1-hydroxy-4-(4-phenyl-1-piperazinyl)butyl]-3,4-dihydrocarbostyril in colorless needle like crystals.
Melting point: 167°–168° C.

| Elemental analysis for $C_{23}H_{29}O_2N_3$ | | | |
|---|---|---|---|
| | C | H | N |
| Calculated (%): | 72.79 | 7.70 | 11.07 |
| Found (%): | 72.94 | 7.48 | 11.31 |

By a method similar to that described in Example 49, by using a suitable starting materials, there were obtained compounds of Examples 50–51 as follows:

EXAMPLE 50

6-{1-Hydroxy-3-[4-(2-methoxyphenyl)-1-piperazinyl]-propyl}-3,4-dihydrocarbostyril Colorless needle-like crystals (from isopropanol)
Melting point: 145°–147° C.

EXAMPLE 51

6-{1-Hydroxy-3-[4-(2,3-dimethylphenyl)-1-piperazinyl]-propyl}-3,4-dihydrocarbostyril Colorless needle-like crystals (from ethanol)
Melting point: 173°–175° C. (decomposed)

EXAMPLE 52

2.0 Grams of 6-[1-oxo-3-(4-phenylpiperazinyl)-propyl]-3,4-dihydrocarbostyril and 0.6 g of 5%-palladium carbon were dispersed in 80 ml of ethanol and stirred at a room temperature under 2 atmospheric pressure of hydrogen gas for 5 hours. The reaction mixture was filtered for removing the palladium carbon and the mother liquor was concentrated under a reduced pressure and the residue thus obtained was recrystallized from isopropanol to obtain 1.4 g of 6-[1-hydroxy-3-(4-phenyl-1-piperazinyl)propyl]-3,4-dihydrocarbostyril in colorless needle-like crystals.
Melting point: 147°–148° C.

| Elemental analysis for $C_{22}H_{29}O_2N_3$ | | | |
|---|---|---|---|
| | C | H | N |
| Calculated (%): | 72.30 | 7.45 | 11.50 |
| Found (%): | 72.62 | 7.18 | 11.29 |

By a method similar to that described in Example 52, by using a suitable starting material, there were obtained compounds of Examples 53–55 as follows:

EXAMPLE 53

6-55
1-Hydroxy-3-[4-(2-methoxyphenyl)-1-piperazinyl]-propyl}-3,4-dihydrocarbostyril Colorless needle-like crystals (from isopropanol)
Melting point: 145°–147° C.

EXAMPLE 54

6-{1-Hydroxy-3-[4-(4-methylphenyl)-1-piperaainyl]-propyl}-3,4-dihydrocarbostyril Colorless needle-like crystals (from isopropanol)
Melting point: 171°–172° C.

EXAMPLE 55

6-{1-Hydroxy-2-[4-(2,3-dimethylphenyl)-1-piperazinyl]-ethyl}carbostyril

Colorless needle-like crystals (from isopropanol-chloroform)
Melting point: 245°–246° C. (decomposed)

EXAMPLE 56

2.0 Grams of 6-{1-Oxo-3-[4-methylpheny)-1-piperazinyl]-propyl}-3,4-dihydrocarbostyril and 1.0 g of lithium aluminium hydride were dispersed in 80 ml of anhydrous tetrahydrofuran and stirred at a room temperature for 8 hours, then 10 ml of actone was added gradually to the reaction mixture and stirred for 1 hour. Under stirring condition, a saturated sodium sulfate aqueous solution was added gradually to the reaction mixture. Aluminium hydroxide and lithium hydroxide were precipitated and the tetrahydrofuran solution was obtained by dacantation. The tetrahydrofuran was removed by distillation and the residue thus obtained was recrystallized from isopropanol to obtain 0.9 g of 6-{1-hydroxy-3-[4-(4-methyl-phenyl)-1-piperazinyl]propyl}-3,4-dihydrocarbostyril in colorless needle-like crystals.
Melting point: 171°–172° C.

| Elemental analysis for $C_{23}H_{29}O_2N_3$ | | | |
|---|---|---|---|
| | C | H | N |
| Calculated (%): | 72.79 | 7.70 | 11.07 |
| Found (%): | 73.01 | 7.58 | 11.31 |

EXAMPLE 57

3.0 Grams of 6-{1-oxo-4-[4-(3-chlorophenyl)-1-piperazinyl]butyl}-3,4-dihydrocarbostyril was added to 100 ml of methanol, under stirring condition 1.2 g of sodium borohydride was added gradually to the solution and stirred at a room temperature for 5 hours. Then 5 ml of concentrated hydrochloric acid was added to the reaction mixture and the mixture was concentrated under a reduced pressure to dryness. Then to this dried matter was added 50 ml of 2%-sodium hydroxide aqueous solution and the organic layer was extracted with dichloromethane. The dichloromethane layer was washed with water, dried and the dichloromethane was removed by distillation. The residue thus obtained was purified by a silica gel column chromatography, and recrystallized from isopropanol to obtain 2.2 g of 6-{1-hydroxy-4-[4-(3-chlorophenyl)-1-piperazinyl]butyl}-3,4-dihydrocarbostyril in colorless needle-like crystals.
Melting point: 156.5°–157° C.

| Elemental analysis for $C_{23}H_{28}O_2N_3Cl$ | | | |
|---|---|---|---|
| | C | N | H |
| Calculated (%): | 66.73 | 6.82 | 10.15 |
| Found (%): | 66.42 | 6.74 | 10.06 |

By a method similar to that described in Example 57, by using a suitable starting materials there were obtained compounds of Examples 58–70 as follows:

EXAMPLE 58

6-[1-Hydroxy-4-(4-phenyl-1-piperazinyl)butyl]-3,4-dihydrocarbostyril

Colorless needle-like crystals (from isopropanol)
Melting point: 167°–168° C.

EXAMPLE 59

6-{1-Hydroxy-2-[4-(3-chlorophenyl)-1-piperazinyl]-butyl}-3,4-dihydrocarbostyril

Colorless flake-like crystals (from ethanol-chloroform)
Melting point: 215°–216° C.

EXAMPLE 60

6-{1-Hydroxy-2-[4-(3-chlorophenyl)-1-piperazinyl]-butyl}carbostyril

Colorless needle-like crystals (from isopropanol-chloroform)
Melting point: 243°–244° C. (decomposed)

EXAMPLE 61

6-{1-Hydroxy-2-[4-(2,3-dimethylphenyl)-1-piperazinyl]ethyl}carbstyril

Colorless needle-like crystals (from isopropanol-chloroform)
Melting point: 245°–246° C. (decomposed)

EXAMPLE 62

6-{1-Hydroxy-2-[4-(4-nitrophenyl)-1-piperazinyl]-butyl}-3,4-dihydrocarbostyril

Yellow powdery crystals
Melting point: 249°–251° C.

EXAMPLE 63

6-[1-Hydroxy-3-(4-phenyl-1-piperazinyl)propyl]-3,4-dihydrocarbostyril

Colorless needle-like crystals (from isopropanol)
Melting point: 147°–148° C.

EXAMPLE 64

6-{1-Hydroxy-4-[4-(2-chlorophenyl)-1-piperazinyl]-butyl}-3,4-dihydrocarbostyril

Colorless needle-like crystals (from isopropanol)
Melting point: 163°–164° C.

EXAMPLE 65

6-{1-Hydroxy-3-[4-(2-methoxyphenyl)-1-piperazinyl]-propyl}-3,4-dihydrocarbostyril Colorless needle-like crystals (from isopropanol)
Melting point: 145°–147° C.

EXAMPLE 66

6-{1-Hydroxy-3-[4-(2,3-dimethylphenyl)-1-piperazinyl]propyl}-3,4-dihydrocarbostyril Colorless needle-like crystals (from ethanol)
Melting point: 173°–175° C. (decomposed)

EXAMPLE 67

6-{1-Hydroxy-3-[4-(4-methylphenyl)-1-piperazinyl]-propyl}-3,4-dihydrocarbostyril Colorless needle-like crystals (from isopropanol)
Melting point: 171°–172° C.

EXAMPLE 68

1-Methyl-6-[1-hydroxy-3-(4-phenyl-1-piperazinyl)-propyl]-3,4-dihydrocarbostyril monooxalate Colorless flake-like crystals (from ethanol-water)
Melting point: 155°–156° C.

EXAMPLE 69

1-Benzyl-6-[1-hydroxy-3-(4-phenyl-1-piperazinyl)-propyl]-3,4-dihydrocarbostyril monooxalate Colorless needle-like crystals (from ethanol-water)
Melting point: 161°–162° C.

EXAMPLE 70

6-{1-Hydroxy-4-[4-(4-aminophenyl)-1-piperazinyl]-butyl}-3,4-dihydrocarbostyril

Brownish powdery crystals (from methanol)
Melting point: 243°–245° C.

5-[1-Hydroxy-3-(4-phenyl-1-piperazinyl)propyl]-3,4-dihydrocarbostyril

Colorless needle-like crystals (from ethanol)
Melting point: 158°–160° C.

EXAMPLE 71

(a) 2.0 Grams of 6-(1-oxo-2-bromobutyl)-3,4-dihydrocarbostyril and 3 g of piperazine were mixed in 80 ml of dioxane and stirred at a room temperature for 5 hours. The reaction mixture was concentrated under a reduced pressure and to the residue thus obtained was added 60 ml of 5%-sodium hydrogencarbonate aqueous solution and extracted with chloroform. The chloroform layer was washed with water and dried then the chloroform was removed by distillation to obtain 1.8 g of crude product of 6-(1-oxo-2-piperazinylbutyl)-3,4-dihydrocarbostyril.

(b) 1.8 Grams of 6-(1-oxo-2-piperazinylbutyl)-3,4-dihydrocarbostyril, 2.0 g of p-bromonitrobenzene, 1.2 g of potassium carbonate and 0.1 g of copper powder were dispersed in 80 ml of ethyl cellosolve and stirred at 120°–150° C. by heating for 5 hours. The reaction mixture was concentrated under a reduced pressure and the residue thus obtained was added water and extracted with chloroform. The chloroform layer was washed with water, dried and the chloroform was removed by distillation. The residue thus obtained was separated and purified by a separative thin layer chromatography and recrystallized from ethanol to obtain 0.2 g of 6-{1-oxo-2-[4-(4-nitrophenyl)-1-piperazinyl]-butyl}-3,4-dihydrocarbostyril in yellow powdery crystals.

Melting point: 239°–242° C.

| Elemental analysis for $C_{23}H_{26}O_4N_4$ | | | |
|---|---|---|---|
|  | C | H | N |
| Calculated (%): | 65.38 | 6.20 | 13.26 |
| Found (%): | 65.02 | 6.51 | 13.59 |

By a method similar to that described in Example 71, by using a suitable starting material, there were obtained compounds of Examples 72–74 as follows:

EXAMPLE 72

6-{1-Oxo-4-[4-(4-nitrophenyl)-1-piperazinyl]butyl}-3,4-dihydrocarbostyril

Yellow needle-like crystals (from dimethylformamide-water)
Melting point: 255°–256° C. (decomposed)

EXAMPLE 73

6-{1-Oxo-3-[4-(4-cyanophenyl)-1-piperazinyl]propyl}-3,4-dihydrocarbostyril

Colorless plate-like crystals (from ethanol)
Melting point: 206°–207° C.

EXAMPLE 74

6-{1-Oxo-4-[4-(4-acetylphenyl)-1-piperazinyl]butyl}-3,4-dihydrocarbostyril

Yellow needle-like crystals (from dimethylformamide-water)
Melting point: 218°–219° C.

6-[1-Oxo-3-(4-benzyl-1-piperazinyl)propyl]-3,4-dihydrocarbostyril

Colorless prism-like crystals (from ethanol-water)
Melting point: 177°–178° C.

6-{1-Oxo-3-[4-(1-tetralinyl)-1-piperazinyl]propyl}-3,4-dihydrocarbostyril

Colorless prism-like crystals (from ethanol-water)
Melting point: 187°–188° C.

EXAMPLE 75

(a) 2.5 Grams of 6-(1-oxo-2-piperazinylbutyl)-3,4-dihydrocarbostyril was mixed in 80 ml of methanol and 1.6 g of sodium borohydride was added gradually under stirring at a room temperature in 15 minutes and further stirred at a room temperature for 2 hours. To the reaction mixture was added 5 ml of concentrated hydrochloric acid and the reaction mixture was concentrated under a reduced pressure to dryness. The residue thus obtained was dissolved by adding 10 ml of water and the pH of the solution was adjusted to 6–7 by adding 2N-sodium hydroxide aqueous solution at a room temperature and stirred to precipitate crystals. The crystals were collected by filtration washed with water and dried to obtain 1.2 g of 6-(1-hydroxy-2-piperazinylbutyl)-3,4-dihydrocarbostyril in colorless powder.

(b) 5.0 Grams of 6-(1-hydroxy-2-piperazinylbutyl)-3,4-dihydrocarbostyril, 3.5 g of p-bromonitroaniline, 1.8 g of potassium carbonate and 0.2 g of copper powder were mixed in 60 ml of 3-methoxybutanol and refluxed by heating for 5 hours. The reaction mixture was filtered and the mother liquor was concentrated by distillation under a reduced pressure to dryness. The residue thus obtained was extracted with methanol-chloroform and the solvent was removed by distillation to obtain a residue. The residue was purified and separated by a preparative silica-gel thin layer chromatograph to obtain 0.21 g of 6-{1-hydroxy-2-[4-nitrophenyl)-1-piperazinyl]butyl}-3,4-dihydrocarbostyril in yellow powdery crystals.

Melting point: 249°–251° C.

EXAMPLE 76

(a) 2.8 Grams of 6-(1-oxo-4-chlorobutyl)-3,4-dihydrocarbostyril and 2.0 g of sodium iodide were mixed in 50 ml of dimethylformamide and stirred at 50° C. for 2 hours. Next, 5.0 g of diethanolamine was added to the reaction mixture and stirred at 70°–80° C. for 5 hours. The reaction mixture was concentrated under a reduced pressure and to the residue thus obtained was added 50 ml of 5%-sodium hydrogencarbonate aqueous solution and stirred. The organic layer was extracted with chloroform and the chloroform layer was washed with water, dried and the chloroform was removed by distillation to obtain 2.5 g of crude 6-(1-oxo-4-diethanolaminobutyl)-3,4-dihydrocarbostyril in a paste form.

(b) To 2.5 g of 6-(1-oxo-4-diethanolaminobutyl)-3,4-dihydrocarbostyril was added 30 ml of thionyl chloride and stirred at a room temperature for 5 hours. Then the reaction mixture was concentrated under a reduced pressure and 50 ml of benzene was added to the residue. The procedures of concentration under a reduced pressure were repeated three times to obtain 6-{1-oxo-4-[di-(2-chloroethyl)amino]-butyl}-3,4-dihydrocarbostyril. To this compound, 1.5 g of aniline, 2.2 g of potassium carbonate and 150 ml of ethanol and the mixture was refluxed by heating for 24 hours. The reaction mixture was concentrated under a reduced pressure and the residue thus obtained was extracted with chloroform. The chloroform layer was washed with water, dried and the chloroform was removed by distillation. The residue thus obtained was separated and purified by a preparative thin layer chromatography, then concentrated hydrochloric acid was added and concentrated to dryness. The residue was recrystallized from ethanol-water to obtain 2.0 g of 6-[1-oxo-4-(4-phenyl-1-piperazinyl)butyl]-3,4-dihydrocarbostyril monohydrochloride in yellow powdery crystals.

Melting point: 195°-196° C.

By a method similar to that described in Example 76, by using a suitable starting material, there were obtained compounds of Examples 77-104 as follows:

EXAMPLE 77

6-{1-Oxo-3-[4-(3-chlorophenyl)-1-piperazinyl]-propyl}-3,4-dihydrocarbostyril monohydrochloride Colorless needle-like crystals (from ethanol-water)
Melting point: 233°-234° C. (decomposed)

EXAMPLE 78

6-{1-Oxo-4-[4-(2-chlorophenyl)-1-piperazinyl]butyl}-3,4-dihydrocarbostyril monohydrochloride monohydrate Colorless needle-like crystals (from water)
Melting point: 266°-268° C. (decomposed)

EXAMPLE 79

6-{1-Oxo-4-[4-(2-ethoxyphenyl)-1-piperazinyl]butyl}-3,4-dihydrocarbostyril monohydrochloride Colorless needle-like crystals (from ethanol-water)
Melting point: 240°-241° C. (decomposed)

EXAMPLE 80

6-{1-Oxo-3-[4-(4-methylphenyl)-1-piperazinyl]-propyl}3,4-dihydrocarbostyril monohydrochloride Light yellow needle-like crystals (from ethanol-water)
Melting point: 224°-226° C. (decomposed)

EXAMPLE 81

6-[1-Oxo-3-(4-phenyl-1-piperazinyl)propyl]-3,4-dihydrocarbostyril

Colorless flake-like crystals (from ethanol-chloroform)
Melting point: 196°-197° C.

EXAMPLE 82

6-{1-Oxo-3-[4-(2-fluorophenyl)-1-piperazinyl]propyl}-3,4-dihydrocarbostyril

Colorless powdery crystals (from dimethylformamide-water)
Melting point: 200°-201° C.

EXAMPLE 83

6-{1-Oxo-4-[4-(4-bromophenyl)-1-piperazinyl]butyl}-3,4-dihydrocarbostyril

Colorless needle-like crystals (from ethanol-water)
Melting point: 184°-185° C.

EXAMPLE 84

6-{1-Oxo-4-[4-(4-nitrophenyl)-1-piperazinyl]butyl}-3,4-dihydrocarbostyril

Yellow needle-like crystals (from dimethyl-formamide-water)
Melting point: 255°-256° C. (decomposed)

EXAMPLE 85

6-{1-Oxo-4-[4-(4-ethoxycarbonylphenyl)-1-piperazinyl]butyl}-3,4-dihydrocarbostyril Colorless needle-like crystals (from ethanol)
Melting point: 191°-192° C.

EXAMPLE 86

6-{1-Oxo-3-[4-(2,3-dimethylphenyl)-1-piperazinyl]-propyl}-3,4-dihydrocarbostyril monohydrochloride Colorless needle-like crystals (from concentrated hydrochloric acid-ethanol-water)
Melting point: 273°-274° C. (decomposed)

EXAMPLE 87

6-{1-Oxo-4-[4-(3,5-dichlorophenyl)-1-piperazinyl]-butyl}-3,4-dihydrocarbostyril

Colorless needle-like crystals (from isopropanol)
Melting point: 194°-195° C.

EXAMPLE 88

6-{1-Oxo-2-[4-(3-chlorophenyl)-1-piperazinyl]ethyl}-3,4-dihydrocarbostyril

Light yellow needle-like crystals (from dioxane-water)
Melting point: 214°-215° C.

EXAMPLE 89

6-{1-Oxo-2-[4-(2,3-dimethylphenyl)-1-piperazinyl]-ethyl}carbostyril

Colorless needle-like crystals (from methanol-chloroform)
Melting point: 199°-200° C. (decomposed)

EXAMPLE 90

6-{1-Oxo-2-[4-(3-chlorophenyl)-1-piperazinyl]butyl} carbostyril monohydrochloride Colorless needle-like crystals (from isopropanol)
Melting point: 209°-210° C. (decomposed)

EXAMPLE 91

6-{1-Oxo-2-[4-(3-chlorophenyl)-1-piperainyl]butyl}-3,4-dihydrocarbostyril monooxalate Colorless needle-like crystals (from isopropanol)
Melting point: 135°-136° C.

EXAMPLE 92

6-{1-Oxo-4-[4-(3-chlorophenyl)-1-piperazinyl]-butyl}3,4-dihydrocarbostyril

Colorless needle-like crystals (from ethanol)
Melting point: 158°-159° C.

EXAMPLE 93

6-{1-Oxo-4-[4-(4-methylphenyl)-1-piperazinyl]butyl}-3,4-dihydrocarbostyril

Light yellow needle-like crystals (from ethanol)
Melting point: 200°–201° C.

EXAMPLE 94

6-{1-Oxo-4-[4-(3,4,5-trimethoxyphenyl)-1-piperazinyl]butyl}-3,4-dihydrocarbostyril dihydrochloride Colorless powdery crystals (from methanol-water)
Melting point: 261°–263° C. (decomposed)

EXAMPLE 95

6-{1-Oxo-3-[4-(4-cyanophenyl)-1-piperazinyl]propyl}-3,4-dihydrocarbostyril

Colorless plate-like crystals (from ethanol)
Melting point: 206°–207° C.

EXAMPLE 96

6-{1-Oxo-4-[4-(4-acetylphenyl)-1-piperazinyl]butyl}3,4-dihydrocarbostyril

Yellow needle-like crystals (from dimethylformamide-water)
Melting point: 218°–219° C.

EXAMPLE 97

6-{1-Oxo-4-[4-(4-methylthiophenyl)-1-piperazinyl]butyl}-3,4-dihydrocarbostyril

Light yellow needle-like crystals (from ethanol)
Melting point: 187°–188° C.

EXAMPLE 98

6-{1-Oxo-3-[4-(2-methoxyphenyl)-1-piperazinyl]propyl}-3,4-dihydrocarbostyril monohydrochloride Light yellow needle-like crystals (from dioxane-water)
Melting point: 212.5°–213° C.

EXAMPLE 99

6-{1-Oxo-4-[4-(4-carbosyphenyl)-1-piperazinyl]butyl}-3,4-dihydrocarbostyril monohydrochloride Colorless powdery crystals (from ethanol)
melting point: 264°–265° C.

EXAMPLE 100

6-{1-Oxo-4-[4-(4-hydroxyphenyl)-1-piperazinyl]butyl}-3,4-dihydrocarbostyril

Colorless powdery crystals (from ethanol)
Melting point: 192°–194° C.

EXAMPLE 101

1-Methyl-6-[1-oxo-3-(4-phenyl-1-piperazinyl)propyl]-3,4-dihydrocarbostyril monooxalate Colorless flake-like crystals (from ethanol-water)
Melting point: 164°–165° C.

EXAMPLE 102

6-{1-Oxo-4-[4-(3,4-methylenedioxyphenyl)-1-piperazinyl]butyl}-3,4-dihydrocarbostyril monohydrochloride Colorless powdery crystals (from ethanol-water)
Melting point: 246°–248°. (decomposed)

EXAMPLE 103

1-Ally-6-[1-oxo-3-(4-phenyl-1-piperazinyl)propyl]-3,4-dihydrocarbostyril monooxalate Colorless flake-like crystals (from ethanol-water)
Melting point: 169°–170° C.

EXAMPLE 104

1-Benzyl-6-[1-oxo-3-(4-phenyl-1-piperazinyl)propyl]-3,4-dihydrocarbostyril monoxalte Colorless needle-like crystals (from ethanol-water)
Melting point: 171°–172° C.

6-[1-Oxo-3-(4-benzyl-1-piperazinyl)propyl]-3,4-dihydrocarbostyril

Colorless needle-like crystals (from ethanol-water)
Melting point: 177°–178° C.

6-{1-Oxo-3-[4-(1-tetralinyl)-1-piperazinyl]propyl}-3,4-dihydrocarbostyril

Colorless prism-like crystals (from ethanol-methanol)
Melting point: 187°–188° C.

5-[1-Oxo-2-(4-phenyl-1-piperazinyl)ethyl]-3,4-dihydrocarbostyril

Colorless needle-like crystals (from methanol)
Melting point: 195°–198° C. (decomposed)

5-[1-Oxo-3-(4-phenyl-1-piperazinyl)propyl]-3,4-dihydrocarbostyril

Colorless needle-like crystals (from ethanol-methanol)
Melting point: 180°–182° C.

5-{1-Oxo-3-[4-(2-ethoxyphenyl)-1-piperazinyl]propyl}-3,4-dihydrocarbostyril mononydrochloride White crystals (from methanol-water)
Melting point: 223°–235° C. (decomposed)

5-{1-Oxo-3-[4-(2-hydroxyphenyl)-1-piperazinyl]propyl}-3,4-dihydrocarbostyril

5-{1-Oxo-3-[4-(4-n-butylphenyl)-1-piperazinyl]propyl}-3,4-dihydrocarbostyril monohydroxide Melting needle-like crystals (from ethanol-water)
Melting point: 218°–222° C. (decomposed).

5-{1-Oxo-3-[4-(2-chlorophenyl)-1-piperazinyl]-propyl}-3,4-dihydrocarbostyril

5-{1-Oxo-3-[4-(2,3-dimethyl)-1-piperazinyl]propyl}-3,4-dihydrocarbostyril monohydrochloride White crystals (from methanol-water)
Melting point: 231°–234° C.

EXAMPLE 105

(a) 2.5 Grams of 6-{1-oxo-4-[di-(2-chloroethyl)-amino]butyl}-3,4-dihydrocarbostyril was dissolved in 80 ml of methanol, with stirring at a room temperature condition 1.6 g of sodium borohydride was added gradually to the mixture in 15 minutes and further stirred at a room temperature for 2 hours. To the reaction mixture was added 5 ml of concentrated hydrochloric acid was added and the reaction mixture was concentrated under a reduced pressure to dryness. The residue thus obtained was dissolved in 10 ml of water, the pH of the solution was adjusted to 6–7 by adding 2N-sodium hydroxide aqueous solution and stirred to precipitate crystals. The crystals were collected by filtration washed with water and dried to obtain 1.4 g of 6-{1-hydroxy-4-[bis(2-chloroethyl)amino]-butyl}-3,4-dihydrocarbostyril in colorless powdery product.

(b) 2.5 Grams of 6-{1-hydroxy-4-[bis-chloroethylamino]butyl}-3,4-dihydrocarbostyril, 1.5 g of aniline and 2.2 g of potassium carbonate were mixed in 150 ml of ethanol and the mixture was refluxed by heating for 24 hours. The reaction mixture was concentrated under a reduced pressure and the residue thus obtained was extracted with chloroform. The chloroform layer was washed with water, dried and chloroform was removed by distillation. The residue thus obtained was separated and purified by a preparative thin layer chromatography and recrystallized from isopropanol to obtain 0.2 g of 6-[1-hydroxy-4-(4-phenyl-1-piperazinyl)butyl]-3,4-dihydrcarbostyril in colorless needle-like crystals.

Melting point: 167°–168° C.

By a method similar to that described in Example 105, by using a suitable starting material, there were obtained compounds of Examples 106–116 as follows:

EXAMPLE 106

6-{1-Hydroxy-4-[4-(3-chlorophehyl)-1-piperazinyl]-butyl}-3,4-dihydrocarbostyril

Colorless needle-like crystals (from chloroform-ether)
Melting point: 156.5°–157° C.

EXAMPLE 107

6-{1-Hydroxy-2-[4-(3-chlorophenyl)-1-piperazinyl]-butyl}-3,4-dihydrocarbostyril

Colorless flake-like crystals (from ethanol-chloroform)
Melting point: 215°–216° C.

EXAMPLE 108

6-{1-Hydroxy-2-[4-(3-chlorophenyl)-1-piperazinyl]-butyl}carbostyril

Colorless needle-like crystals (from isopropanol-chloroform)
Melting point: 243°–244° C. (decomposed)

EXAMPLE 109

6-{1-Hydroxy-2-[4-(2,3-dimethylphenyl)-1-piperazinyl]-ethyl}carbostyril

Colorless needle-like crystals (from isopropanol-chloroform)
Melting point: 245°–246° C. (decomposed)

EXAMPLE 110

6-[1-Hydroxy-3-(4-phenyl-1-piperazinyl)propyl]-3,4-dihydrocarbostyril

Colorless needle-like crystals (from isopropanol)
Melting point: 147°–148° C.

EXAMPLE 111

6-{1-Hydroxy-4-[4-(2-chlorophenyl)-1-piperazinyl]-butyl}-3,4-dihydrocarbostyril

Colorless needle-like crystals (from isopropanol)
Melting point: 163°–164° C.

EXAMPLE 112

6-{1-Hydroxy-3-[4-(2-methoxyphenyl)-1-piperazinyl]-propyl}-3,4-dihydrocarbostyril Colorless needle-like crystals (from isopropanol)
Melting point: 145°–147° C.

EXAMPLE 113

6-{1-Hydroxy-3-[4-(2,3-dimethylphenyl)-1-piperazinyl]-propyl}-3,4-dihydrocarbostyril Colorless needle-like crystals (from ethanol)
Melting point: 173°–175° C. (decomposed)

EXAMPLE 114

6-{1-Hydroxy-3-[4-(4-methylphenyl)-1-piperazinyl]-propyl}-3,4-dihydrocarbostyril Colorless needle-like crystals (from isopropanol)
Melting point: 171°–172° C.

EXAMPLE 115

1-Methyl-6-[1-hydroxy-3-(4-phenyl-1-piperazinyl)-propyl]-3,4-dihydrocarbostyril monooxalate Colorless flake-like crystals (from ethanol-water)
Melting point: 155°–156° C.

EXAMPLE 116

1-Benzyl-6-[1-hydroxy-3-(4-phenyl-1-piperazinyl)-propyl]-3,4-dihydrocarbostyril monooxalate Colorless needle-like crystals (from ethanol-water)
Melting point: 161°–162° C.

5-[1-Hydroxy-3-(4-phenyl-1-piperazinyl)-propyl]-3,4-dihydrocarbostyril

Colorless needle-like crystals (from ethanol-water)
Melting point: 158°–160° C.

EXAMPLE 117

(a) 5.0 Grams of 6-(1-oxo-2-chloroethyl)-3,4-dihydrocarbostyril and 6.0 g of morpholine were dispersed in 120 ml of dioxane and stirred at 60°–70° C. for 12 hours. The reaction mixture was concentrated under a reduced pressure. The residue thus obtained was stirred with ether and the insoluble matter was collected by filtration and washed with water. Then the insoluble matter was dissolved in 80 ml of methanol and 10 ml of concentrated hydrochloric acid by heating and the solution was concentrated under a reduced pressure to dryness. The residue thus obtained was recrystallized from methanol-ether twice and obtained 5.9 g of 6-(1-oxo-2-morpholinoethyl)-3,4-dihydrocarbostyril monohydrochloride in colorless powdery product.

Melting point: 290° C. (decomposed).

(b) 5.0 Grams of 6-(1-oxo-2-morpholinoethyl)-3,4-dihydrocarbostyril monohydrochloride and 5.0 g of m-chloroaniline were mixed in 30 ml of concentrated hydrochloric acid and the mixture was heated at 200°–220° C. by removing water for 6 hours. After cooled the reaction mixture 100 ml of 5N-hydrochloric acid was added thereto and dissolved by heating and refluxed for 2 hours. Then the reaction mixture was cooled and poured into 100 ml of 8N-sodium hydroxide aqueous solution and the organic layer was extracted with chloroform. Chloroform was removed by distillation and the residue thus obtained was separated and purified by a preparative silica-gel thin layer chromatography, then recrystallized from dioxane-water to obtain 0.16 g of 6-{1-oxo-2-[4-(3-chlorophenyl)-1-piperazinyl]-ethyl}-3,4-dihydrocarbostyril in light yellow needle-like crystals.

Melting point: 214°–215° C.

| Elemental analysis for C$_{21}$H$_{22}$O$_2$N$_3$Cl | | | |
|---|---|---|---|
| | C | H | N |
| Calculated (%): | 65.71 | 5.78 | 10.95 |
| Found (%): | 65.98 | 5.62 | 10.78 |

By a method similar to that described in Example 117, by using a suitable starting material, there were obtained compounds of Examples 118–140 as folows:

EXAMPLE 118

6-{1-Oxo-3-[4-(3-chlorophenyl)-1-piperazinyl]propyl}-3,4-dihydrocarbostyril monohydrochloride Colorless needle-like crystals (from ethanol-water)
Melting point: 233°–234° C. (decomposed)

EXAMPLE 119

6-{1-Oxo-4-[4-(2-chlorophenyl)-1-piperazinyl]butyl}-3,4-dihydrocarbostyril monohydrochloride monohydrate Colorless needle-like crystals (from water)
Melting point: 266°–268° C. (decomposed)

EXAMPLE 120

6-[1-Oxo-4-(4-phenyl-1-piperazinyl)butyl]-3,4-dihydrocarbostyril monohydrochloride Yellow powdery crystals (from ethanol-water)
Melting point: 195°–196° C. (decomposed)

EXAMPLE 121

6-{1-Oxo-3-[4-(4-methylphenyl)-1-piperazinyl]propyl}-3,4-dihydrocarbostyril monohydrochloride Light yellowish needle-like crystals (from ethanol-water)
Melting point: 224°–226° C. (decomposed)

EXAMPLE 122

6-[1-Oxo-3-(4-phenyl-1-piperazinyl)propyl]-3,4-dihydrocarbostyril

Colorless flake-like crystals (ethanol-chloroform)
Melting point: 196°–197° C.

EXAMPLE 123

6-{1-Oxo-3-[4-(2-fluorophenyl)-1-piperazinyl]butyl}-3,4-dihydrocarbostyril

Colorless powdery crystals (from dimethylformamide-water)
Melting point: 200°–201° C.

EXAMPLE 124

6-{1-Oxo-4-[4-(4-bromophenyl)-1-piperazinyl]butyl}-3,4-dihydrocarbostyril

Colorless needle-like crystals (from ethanol-water)
Melting point: 184°–185° C.

EXAMPLE 125

6-{1-Oxo-4-[4-nitrophenyl)-1-piperazinyl]butyl}-3,4-dihydrocarbostyril

Yellow needle-like crystals (from dimethylformamide-water)
Melting point: 255°–256° C. (decomposed).

EXAMPLE 126

6-{1-Oxo-3-[4-(2,3-dimethylphenyl)-1-piperazinyl]propyl}-3,4-dihydrocarbostyril monohydrochloride Colorless needle-like crystals (from concentrated hydrochloric acid-ethanol-water)
Melting point: 273°–274° C. (decomposed)

EXAMPLE 127

6-{1-Oxo-4-[4-(3,5-dichlorophenyl)-1-piperazinyl]butyl}-3,4-dihydrocarbostyril

Colorless needle-like crystals (from isopropanol)
Melting point: 194°–195° C.

EXAMPLE 128

6-[1-Oxo-4-(4-phenyl-1-piperazinyl)butyl]-3,4-dihydrocarbostyril monohydrochloride Yellowish powdery crystals (from ethanol-water)
Melting point: 195°–196° C. (decomposed)

EXAMPLE 129

6-{1-Oxo-2-[4-(2,3-dimethylphenyl)-1-piperazinyl]-ethyl}carbostyril

Colorless needle-like crystals (from methanol-chloroform)
Melting point: 199°–200° C. (decomposed)

EXAMPLE 130

6-{1-Oxo-2-[4-(3-chlorophenyl)-1-piperazinyl]butyl} carbostyril monohydrochloride Colorless needle-like crystals (from isopropanol)
Melting point: 209°–210° C. (decomposed)

EXAMPLE 131

6-{1-Oxo-2-[4-(3-chlorophenyl)-1-piperazinyl]butyl}-3,4-dihydrocarbostyril monooxalate Colorless needle-like crystals (from isopropanol)
Melting point: 135°–136° C.

EXAMPLE 132

6-{1-Oxo-4-[4-(3-chlorophenyl)-1-piperazinyl]butyl}-3,4-dihydrocarbostyril

Colorless needle-like crystals (from ethanol)
Melting point: 158°–159° C.

EXAMPLE 133

6-{1-Oxo-4-[4-(4-methylphenyl)-1-piperazinyl]butyl}-3,4-dihydrocarbostyril

Light yellow needle-like crystals (from ethanol)
Melting point: 200°–201° C.

EXAMPLE 134

6-{1-Oxo-4-[4-(4-acetylphenyl)-1-piperazinyl]butyl}-3,4-dihydrocarbostyril

Yellow needle-like crystals (from dimethylformamide-water)
Melting point: 218°–219° C.

EXAMPLE 135

6-{1-Oxo-4-[4-(4-carboxyphenyl)-1-piperazinyl]butyl}-3,4-dihydrocarbostyril monohydrochloride Colorless powdery crystals (from ethanol)
Melting point: 264°–265° C.

EXAMPLE 136

6-{1-Oxo-4-[4-(4-hydroxyphenyl)-1-piperazinyl]butyl}-3,4-dihydrocarbostyril

Colorless powdery crystals (from ethanol)
Melting point: 192°–194° C.

EXAMPLE 137

1-Methyl-6-[1-oxo-3-(4-phenyl-1-piperazinyl)propyl]-3,4-dihydrocarbostyril monooxalate Colorless flake-like crystals (from ethanol-water)
Melting point: 164°–165° C.

EXAMPLE 138

1-Hexyl-6-[1-oxo-3-(4-phenyl-1-piperazinyl)propyl]-3,4-dihydrocarbostyril monooxalte Colorless flake-like crystals (from ethanol-water)
Melting point: 142°–144° C.

EXAMPLE 139

1-Benzyl-6-[1-oxo-3-(4-phenyl-1-piperazinyl)propyl]-3,4-dihydrocarbostyril monooxalte Colorless needle-like crystals (ethanol-water)
Melting point: 171°–172° C.

EXAMPLE 140

1-Allyl-6-[1-oxo-3-(4-phenyl-1-piperazinyl)propyl]-3,4-dihydrocarbostyril monooxalte Colorless flake-like crystals (from ethanol-water)
Melting point: 169°–170° C.

5-[1-Oxo-3-(4-phenyl-1-piperazinyl)propyl]-3,4-dihydrocarbostyril

Colorless needle-like crystals (from ethanol-methanol)
Melting point: 180°–182° C.

5-{1-Oxo-3-[4-(2-ethoxyphenyl)-1-piperazinyl]propyl}-3,4-dihydrocarbostyril monohydrochloride White crystals (from methanol-water)
Melting point: 223°–235° C. (decomposed)

5-{1-Oxo-3-[4-(2-hydroxyphenyl)-1-piperazinyl]propyl}-3,4-dihydrocarbostyril

5-{1-Oxo-3-[4-(4-n-butylphenyl)-1-piperazinyl]propyl}-3,4-dihydrocarbostyril monohydrochloride Colorless needle-like crystals (from ethanol-water)
Melting point: 218°–222° C.

5-{1-Oxo-3-[4-(2-chlorophenyl)-1-piperazinyl]-propyl}-3,4-dihydrocarbostyril

5-{1-Oxo-3-[4-(2,3-dimethylphenyl)-1-piperazinyl]propyl}-3,4-dihydrocarbostyril monohydrochloride White crystals (from methanol-water)
Melting point: 231°–234° C.

6-[1-Oxo-3-(4-benzyl-1-piperazinyl)propyl]-3,4-dihydrocarbostyril

Colorless needle-like crystals (from ethanol-water)
Melting point: 177°–178° C.

6-{1-Oxo-3-[4-(1-teralinyl)-1-piperazinyl]-propyl}-3,4-dihydrocarbostyril

Colorless prism-like crystals (from ethanol)
Melting point: 187°–188° C.

5-[1-Oxo-2-(4-phenyl-1-piperazinyl)ethyl]-3,4-dihydrocarbostyril

Colorless needle-like crystals (from methanol)
Melting point: 195°–198° C. (decomposed).

EXAMPLE 141

1.5 Gram of 6-{1-oxo-4-[4-(4-nitrophenyl)-piperazinyl]-butyl}-3,4-dihydrocarbostyril and 0.3 g of 5% palladium-carbon were dispersed in 150 ml of ethanol and catalytically reduced under 2 kg/cm$^2$ of hydrogen gas for 5 hours. The reaction mixture was filtered and the mother liquor was concentrated under a reduced pressure. The residue thus obtained was recrystallized from methanol to obtain 0.7 g of 6-{1-hydroxy-4-[4-(4-aminophenyl)-1-piperazinyl]butyl}-3,4-dihydrocarbostyril in brown powdery crystals.
Melting point: 243°–245° C.

| Elemental analysis for $C_{23}H_{30}O_2N_4$ | | | |
|---|---|---|---|
| | C | H | N |
| Calculated (%): | 70.02 | 7.67 | 14.20 |
| Found (%): | 70.38 | 7.41 | 14.02 |

EXAMPLE 142

2.0 Grams of 6-{1-oxo-4-[4-(4-ethoxy-carbonylphenyl)-1-piperazinyl]butyl}-3,4-dihydrocarbostyril and 0.6 g of sodium hydroxide were mixed in 70 ml of methanol and refluxed by heating for 2 hours. To the reaction mixture was added 5 ml of concentrated hydrochloric acid and the mixture was concentrated under a reduced pressure to dryness. The residue was recrystallized from ethanol-water to obtain 0.6 g of 6-{1-oxo-4-[4-(4-carboxyphenyl)-1-piperazinyl]butyl}-3,4-dihydrocarbostyril monohydrochloride in colorless needle-like crystals.
Melting point: 267°–268° C. (decomposed)

| Elemental analysis for $C_{24}H_{27}O_4N_3.HCl$ | | | |
|---|---|---|---|
| | C | H | N |
| Calculated (%): | 62.95 | 6.16 | 9.18 |
| Found (%): | 62.58 | 6.32 | 9.41 |

EXAMPLE 143

2.8 Grams of 6-{1-hydroxy-3-[4-(2-methoxyphenyl)-1-piperazinyl]propyl}-3,4-dihydrocarbostyril was dissolved in 100 ml of dioxane and 5 ml of concentrated hydrochloric acid was added thereto, then the mixture was refluxed for 15 minutes. The reaction mixture was concentrated under a reduced pressure to dryness to obtain a residue. To the residue were added 10N-NaOH and further and stirred at a room temperature for 30 minutes to precipitates crystals. The crystals were colected by filtration, washed with ether then recrystallized from ethanol-chloroform-acetone to obtain 6-{3-[4-(2-methoxyphenyl)-1-piperazinyl]-1-propenyl}-3,4-dihydrocarbostyril in colorless needle-like crystals. Yield: 2.3 g.

Melting point: 174°-175° C.

EXAMPLE 144

2.8 Grams of 6-{1-hydroxy-4-[4-(2,3-dimethylphenyl)-1-piperazinyl]butyl}-3,4-dihydrocarbostyril and 0.5 g of p-toluenesulfonic acid were dissolved in 100 ml of dichloroethane then the mixture was refluxed for 20 minutes. The reaction mixture was concentrated under a reduced pressure to dryness then to the residue thus obtained were added 10N-NaOH and diethyl ether and stirred at a room temperature for 30 minutes. The crystals thus precipitated were collected by filtration and separated by a silica-gel chromatography. Recrystallized from ethanol-acetone-chloroform to obtain 6-{4-[4-(2,3-dimethylphenyl)piperazinyl]-1-butenyl}-3,4-dihydrocarbostyril in colorless needle-like crystals. Yield: 1.9 g.

Melting point: 175°-176° C.

EXAMPLE 145

1.9 Grams of 6-{1-hydroxy-4-[4-(3-chlorophenyl)-1-piperazinyl]butyl}-3,4-dihydrocarbostyril was dissolved in 50 ml of acetic acid and further 2 ml of concentrated hydrochloric acid was added to this solution. The solution was stirred at 80° C. for 30 minutes and the reaction mixture was concentrated under a reduced pressure to dryness to obtain a residue. To the residue were added 10N-NaOH and ether and stirred at a room temperature for 30 minutes. The crystals thus precipitated were collected by filtration and separated by a silica-gel chromatography. Recrystallized from ethanol-chloroform to obtain 6-{4-[4-(3-chlorophenyl)-1-piperazinyl]-1-butenyl}-3,4-dihydrocarbostyril in colorless prism-like crystals. Yield: 1.6 g. Melting point: 175°-176° C.

By a method similar to that described in Example 145, there were obtained compounds of Examples 146–171 as follows:

EXAMPLE 146

6-[3-(4-Phenyl-1-piperazinyl)-1-propenyl]-3,4-dihydrocarbostyril

Colorless prism-like crystals (from ethanol)
Melting point: 186°-187° C.

EXAMPLE 147

6-[4-(4-Phenyl-1-piperazinyl)-1-butenyl]-3,4-dihydrocarbostyril

Colorless prism-like crystals (from ethanol-chloroform)
Melting point: 187°-188° C.

EXAMPLE 148

6-{3-[4-(2-Chlorophenyl)-1-piperazinyl]-1-prpenyl}-3,4-dihydrocarbostyril

Colorless prism-like crystals (from ethanol-chlkoroform)

EXAMPLE 149

6-{3-[4-(3-Chlorophenyl)-1-piperazinyl]-1-propenyl}-3,4-dihydrocarbostyril

Colorless prism-like crystals (from ethanol-chloroform)
Melting point: 163°-164° C.

EXAMPLE 150

6-{3-[4-(4-Chlorophenyl)-1-piperazinyl]-1-propenyl}-3,4-dihydrocarbostyril

Colorless prism-like crystals (from ethanol-chloroform)
Melting point: 224.5°-225.5° C.

EXAMPLE 151

6-{3-[4-(2-Fluorophenyl)-1-piperazinyl]-1-propenyl}-3,4-dihydrocarbostyril

Colorless prism-like crystals (from ethanol-chloroform)
Melting point: 188.5°-190° C.

EXAMPLE 152

6-{3-[4-(2-Ethoxyphenyl)-1-piperazinyl]-1-propenyl}-3,4-dihydrocarbostyril

Colorless needle-like crystals (from methanol-chloroform)
Melting point: 203°-204° C.

EXAMPLE 153

6-{4-[4-(2-Ethoxyphenyl)-1-piperazinyl]-1-butenyl}-3,4-dihydrocarbostyril

Colorless needle-like crystals (from ethanol-chloroform)
Melting point: 205°-206° C.

EXAMPLE 154

6-{3-[4-(3-Methylphenyl)-1-piperazinyl]-1-propenyl}-3,4-dihydrocarbostyril

Colorless prism-like crystals (from ethanol)
Melting point: 167°-168° C.

EXAMPLE 155

6-{-[4-(3-Methylphenyl)-1-piperazinyl]-1-butenyl}-3,4-dihydrocarbostyril

Colorless prism-like crystals (from ethanol)
Melting point: 171.5°-172.5° C.

EXAMPLE 156

6-{4-[4-(4-Methylphenyl)-1-piperazinyl]-1-butenyl}-3,4-dihydrocarbostyril

Colorless prism-like crystals (from ethanol-chloroform)
Melting point: 202°-203° C.

EXAMPLE 157

6-{3-[4-(2-Methoxyphenyl)-1-piperazinyl]-1-propenyl}-3,4-dihydrocarbostyril

Colorless needle-like crystals (from ethanol-acetone-chloroform)
Melting point: 174°-175° C.

EXAMPLE 158

6-{4-[4-(2,3-Dimethylphenyl)-1-piperaziny]-1-butenyl}-3,4-dihydrocarbostyril

Colorless prism-like crystals (from ethanol-acetone-chloroform)
Melting point: 175°–176° C.

EXAMPLE 159

6-{4-[4-(2-Chloro-6-methylphenyl)-1-piperazinyl]-1-butenyl}-3,4-dihydrocarbostyril Colorless prism-like crystals (from ethanol-acetone-chloroform)
Melting point: 179°–180° C.

EXAMPLE 160

6-{3-[4-(4-Ethoxycarbonylphenyl)-1-piperazinyl]-1-propenyl}-3,4-dihydrocarbostyril Colorless needle-like crystals (from ethanol-chloroform)
Melting point: 190°–192° C.

EXAMPLE 161

6-{4-[4-(4-Methylthiophenyl)-1-piperazinyl]-1-butenyl}-3,4-dihydrocarbostyril

Colorless needle-like crystals (from ethanol-chloroform)
Melting point: 175.5°–177° C.

EXAMPLE 162

6-{4-[4-(4-Actylphenyl)-1-piperazinyl]-1-butenyl}3,4-dihydrocarbostyril

Colorless prism-like crystals (from ethanol-chloroform)
Melting pont: 213°–215° C.

EXAMPLE 163

6-{3-[4-(4-Cyanophenyl)-1-piperazinyl]-1-propenyl}-3,4-dihydrocarbostyril

Colorless prism-like crystals (from ethanol-chloroform)
Melting point: 196°–198° C.

EXAMPLE 164

6-{3-[4-(2-Hydroxyphenyl)-1-piperazinyl]-1-propenyl}-3,4-dihydrocarbostyril

Colorless prism-like crystals (from ethanol-chloroform)
Melting point: 192°–194° C.

EXAMPLE 165

1-Methyl-6-{3-[4-(3-methylphenyl)-1-piperazinyl]-1-propenyl}-3,4-dihydrocarbostyril monooxalate Light yellow needle-like crystals (from ethanol)
Melting point: 178°–179° C.

EXAMPLE 166

1-Benzyl-6-{3-[4-(3-methylphenyl)-1-piperazinyl]-1-propenyl}-3,4-dihydrocarbostyril monooxalate Colorless needle-like crystals (from ethanol)
Melting point: 176°–179° C.

EXAMPLE 167

1-Allyl-6-{3-[4-(3-methylphenyl)-1-piperazinyl]-1-propenyl}-3,4-dihydrocarbostyril monooxalate Colorless needle-like crystals (from ethanol)
Melting point: 167°–168° C.

EXAMPLE 168

1-(2-Propynyl)-6-{3-[4-(3-methylphenyl)-1-piperazinyl]-1-propenyl}-3,4-dihydrocarbostyril monooxalate Colorless powdery crystals (from ethanol)
Melting point: 158°–160° C.

EXAMPLE 169

6-{3-[4-(3-Carboxyphenyl)-1-piperazinyl]-1-propenyl}-3,4-dihydrocarbostyril monohydrochloride Colorless needle-like crystals (from ethanol-water)
Melting point: 264°–266° C.

EXAMPLE 170

6-{4-[4-(3,4-Methylenedioxyphenyl)-1-piperazinyl)]-1-butenyl}-3,4-dihydrocarbostyril monohydrochloride Colorless needle-like crystals (from methanol)
Melting point: 226°–228° C.

EXAMPLE 171

6-[3-Methyl-3-(4-phenyl-1-piperazinyl)-1-propenyl]-3,4-dihydrocarbostyril

Colorless prism-like crystals (from ethanol-chloroform)
Melting point: 172°–173° C.

5-[3-(4-Phenyl-1-piperazinyl)-1-propenyl]-3,4-dihydrocarbostyril

Colorless prism-like crystals (from methanol)
Melting point: 177°–180° C.

EXAMPLE 172

2.8 Grams of 6-(4-chloro-1-butenyl)-3,4-dihydrocarbostyril and 2.1 g of sodium iodide were dissolved in 40 ml of dimethylformamide and stirred at 50° C. for 1 hour. To this solution were added 2.7 g of 4-(2-chloro-6-methylphenyl)piperazine and 1.5 g of triethylamine and the mixture was further stirred at 50° C. for 5 hours. The reaction mixture was concentrated under a reduced pressure to dryness to obtain a residue. To the residue were added 10N-NaOH and ether and stirred at a room temperature for 30 minutes to precipitate crystals. The crystals were separated by a silica-gel chromatography and recrystallized from ethanol-acetone-chloroform to obtain 6-{4-[4-(2-chloro-6-methylphenyl)-1-piperazinyl]-1-butenyl}-3,4-dihydrocarbostyril in colorless prism-like crystals. Yield: 2.7 g. Melting point: 179°–180° C.

By a method similar to that described in Example 172, there were obtained compounds of Examples 173–195 as follows:

EXAMPLE 173

6-[3-(4-Phenyl-1-piperazinyl)-1-propenyl]-3,4-dihydrocarbostryil

Colorless prism-like crystals (from ethanol)
Melting point: 186°–187° C.

EXAMPLE 174

6-[4-(4-Phenyl-1-piperazinyl)-1-butenyl]-3,4-dihydrocarbostyril

Colorless prism-like crystals (from ethanol-chloroform)
Melting point: 187°–188° C.

EXAMPLE 175

6-{4-[4-(3-Chlorophenyl)-1-piperazinyl]-1-butenyl}-3,4-dihydrocarbostyril

Colorless prism-like crystals
Melting point: 175°–176° C.

EXAMPLE 176

6-{3-[4-(2-Chlorophenyl)-1-piperazinyl]-1-propenyl}-3,4-dihydrocarbostyril

Colorless prism-layer crystals (from ethanol-chloroform)
Melting point: 151.5°–152.5° C.

EXAMPLE 177

6-{3-[4-(3-Chlorophenyl)-1-piperazinyl]-1-propenyl}-3,4-dihydrocarbostyril

Colorless prism-like crystals (from ethanol-chloroform)
Melting point: 163°–164° C.

EXAMPLE 178

6-{3-[4-(4-Chlorophenyl)-1-piperazinyl]-1-propenyl}-3,4-dihydrocarbostyril

Colorless prism-like crystals (from ethanol-chloroform)
Melting point: 224.5°–225.5° C.

EXAMPLE 179

6-{3-[4-(2-Fluorophenyl)-1-piperazinyl]-1-propenyl}-3,4-dihydrocarbostyril

Colorless prism-like crystals (from ethanol-chloroform)
Melting point: 188.5°–190° C.

EXAMPLE 180

6-{3-[4-(2-Ethoxyphenyl)-1-piperazinyl]-1-propenyl}-3,4-hydrocarbostyril

Colorless needle-like crystals (from methanol-chloroform)
Melting point: 203°–204° C.

EXAMPLE 181

6-{4-[4-(2-Ethoxyphenyl)-1-piperazinyl]-1-butenyl}-3,4-dihydrocarbostyril

Colorless needle-like crystals (from ethanol-chloroform)
Melting point: 205°–206° C.

EXAMPLE 182

6-{3-[4-(3-Methylphenyl)-1-piperazinyl]-1-propenyl}-3,4-dihydrocarbostyril

Colorless prism-like crystals (from ethanol)
Melting point: 167°–168° C.

EXAMPLE 183

6-{4-[4-(3-Methylphenyl)-1-piperazinyl]-1-butenyl}-3,4-dihydrocarbostyril

Colorless prism-like crystals (from ethanol)
Melting point: 171.5°–172.5° C.

EXAMPLE 184

6-{4-[4-(4-Methylphenyl)-1-piperazinyl]-1-butenyl}-3,4-dihydrocarbostyril

Colorless prism-like crystals (from ethanol-chloroform)
Melting point: 202°–203° C.

EXAMPLE 185

6-{3-[4-(2-Methoxyphenyl)-1-piperazinyl]-1-propenyl}-3,4-dihydrocarbostyril

Colorless needle-like crystals (from ethanol-acetone-chloroform)
Melting point: 174°–175° C.

EXAMPLE 186

6-{4-[4-(2,3-Dimethylphenyl)-1-piperazinyl]-1-butenyl}-3,4-dihydrocarbostyril

Colorless prism-like crystals (from ethanol-acetone-chloroform)
Melting point: 175°–176° C.

EXAMPLE 187

6-{3-[4-(4-Ethoxycarbonylphenyl)-1-piperazinyl]-1-propenyl}-3,4-dihydrocarbostyril Colorless needle-like crystals (from ethanol-chloroform)
Melting point: 190°–192° C.

EXAMPLE 188

6-{4-[4-(4-Methylthiophenyl)-1-piperazinyl]-1-butenyl}-3,4-dihydrocarbostyril

Colorless needle-like crystals (from ethanol-chloroform)
Melting point: 175.5°–177° C.

EXAMPLE 189

6-{4-[4-(4-Acetylphenyl)-1-piperazinyl]-1-butenyl}-3,4-dihydrocarbostyril

Colorless prism-like crystals (from ethanol-chloroform)
Melting point: 213°–215° C.

EXAMPLE 189

6-{4-[4-(4-Acetylphenyl)-1-piperazinyl]-1-butenyl}-3,4-dihydrocarbostyril

Colorless prism-like crystals (from ethanol-chloroform)
Melting point: 213°–215° C.

EXAMPLE 190

6-{3-[4-(4-Cyanophenyl)-1-piperazinyl]-1-propenyl}-3,4-dihydrocarbostyril

Colorless prism-like crystals (from ethanol-chloroform)
Melting point: 196°–198° C.

EXAMPLE 191

6-{3-[4-(2-Hydroxyphenyl)-1-piperazinyl]-1-propenyl}-3,4-dihydrocarbostyril

Colorless prism-like crystals (from ethanol-chloroform)
Melting point: 192°–194° C.

EXAMPLE 192

1-Methyl-6-{3-[4-(3-methylphenyl)-1-piperazinyl]-1-propenyl}-3,4-dihydrocarbostyril monooxalate Light yellowish needle-like crystals (from ethanol)
Melting point: 178°–179° C.

EXAMPLE 193

1-Benzyl-6-{3-[4-(3-methylphenyl)-1-piperazinyl]-1-propenyl}-3,4-dihydrocarbostyril monooxalate Colorless needle-like crystals (from ethanol)
Melting point: 176°–179° C.

EXAMPLE 194

1-Allyl-6-{3-[4-(3-methylphenyl)-1-piperazinyl]-1-propenyl}-3,4-dihydrocarbostyril monooxalate Colorless needle-like crystals (from ethanol)
Melting point: 167°–168° C.

EXAMPLE 195

1-(2-Propinyl)-6-{3-[4-(3-methylphenyl)-1-piperazinyl]-1-propenyl}-3,4-dihydrocarbostyril monooxalate Colorless needle-like crystals (from ethanol)
Melting point: 158°–160° C.

5-[3-(4-Phenyl-1-piperazinyl)-1-propenyl]-3,4-dihydrocarbostyril

Colorless prism-like crystals (from methanol)
Melting point: 177°–180° C.

EXAMPLE 196

5.0 Grams of 6-{1-oxo-3-[4-(3-tolyl)-1-piperazinyl]-propyl}-3,4-dihydrocarbostyril was suspended in 250 ml of methanol, and 2.5 g of sodium borohydride was added gradually to this solution under ice-cooling condition and the mixture was stirred for 30 minutes. Then 10 ml of acetone was added to the mixture and the reaction mixture was concentrated under a reduced pressure to dryness. To the residue thus obtained were added 10N-NaOH and ether and stirred at a room temperature for 30 minutes. The crystals thus formed were collected by filtration and were suspended in 250 ml of dioxane then added 10 ml of concentrated hydrochloric acid. The mixture was refluxed for 15 minutes then concentrated under a reduced pressure to dryness. The residue thus obtained was separated by a silica-gel chromatography and recrystallized from ethanol to obtain 6-{3-[4-(3-tolyl)-1-piperazinyl]-1-propenyl}-3,4-dihydrocarbostyril in colorless prism-like crystals. Yield: 2.9 g Melting point: 167°–168° C.

By a method similar to that described in Example 196, there were obtained compounds of Examples 197–221 as follows:

EXAMPLE 197

6-[3-(4-Phenyl-1-piperazinyl)-1-propenyl]-3,4-dihydrocarbostyril

Colorless prism-like crystals (from ethanol)
Melting point: 186°–187° C.

EXAMPLE 198

6-[4-(4-Phenyl-1-piperazinyl)-1-butenyl]-3,4-dihydrocarbostyril

Colorless prism-like crystals (from ethanol-chloroform)
Melting point: 187°–188° C.

EXAMPLE 199

6-{4-[4-(3-Chlorophenyl)-1-piperazinyl]-1-butenyl}-3,4-dihydrocarbostyril

Colorless prism-like crystals (from
Melting point: 175°–176° C.

EXAMPLE 200

6-{4-[4-(3-Methylphenyl)-1-piperazinyl]-1-butenyl}carbostyril monohydrochloride

Colorless needle-like crystals (from methanol)
Melting point: 233°–235° C.

EXAMPLE 201

6-{4-[4-(2-Chloro-6-methylpohenyl)-1-piperazinyl]-1-butenyl}-3,4-dihydrocarbostyril Colorless prism-like crystals
Melting point: 179°–180° C.

EXAMPLE 202

6-{4-[4-(4-Acetylphenyl)-1-piperazinyl]-1-butenyl}-3,4-dihydrocarbostyril

Colorless prism-like crystals (from ethanol-chloroform)
Melting point: 213°–215° C.

EXAMPLE 203

6-{3-[4-(4-Cyanophenyl)-1-piperazinyl]-1-propenyl}-3,4-dihydrocarbostyril

Colorless prism-like crystals (from ethanol-chloroform)
Melting point: 196°–198° C.

EXAMPLE 204

6-{3-[4-(2-Hydroxyphenyl)-1-piperazinyl]-1-propenyl}-3,4-dihydrocarbostyril

Colorless prism-like crystals (from ethanol-chloroform)
Melting point: 192°–194° C.

EXAMPLE 205

1-Methyl-6-{3-[4-(3-methylphenyl)-1-piperazinyl]-1-propenyl}-3,4-dihydrocarbostyril monooxalate Light yellow needle-like crystals (from ethanol)
Melting point: 178°–179° C.

EXAMPLE 206

1-Benzyl-6-{3-[4-(3-methylphenyl)-1-piperazinyl]-1-propenyl}-3,4-dihydrocarbostyril monooxalate Colorless needle-like crystals (from ethanol)
Melting point: 176°–179° C.

EXAMPLE 207

1-Allyl-6-{3-[4-(3-methylphenyl)-1-piperazinyl]-1-propenyl}-3,4-dihdrocarbostyril monooxalate Colorless needle-like crystals (from ethanol)
Melting point: 167°–168° C.

EXAMPLE 208

1-(2-Propinyl)-6-{3-[4-(3-methylphenyl)-1-piperazinyl]-propenyl}-3,4-dihydrocarbostyril monooxalate Colorless powdery crystals (from ethanol)
Melting point: 158°–160° C.

EXAMPLE 209

6-{4-[4-(3-Methylphenyl)-1-piperazinyl]-1-butenyl}-3,4-dihydrocarbostyril

Colorless prism-like crystals (from ethanol)
Melting point: 171.5°–172.5° C.

EXAMPLE 210

6-{4-[4-(4-Methylphenyl)-1-piperazinyl]-1-butenyl}-3,4-dihydrocarbostyril

Colorless prism-like crystals (from ethanol chloroform)
Melting point: 202°–203° C.

EXAMPLE 211

6-{3-[4-(2-Methoxyphenyl)-1-piperazinyl]-1-propenyl}-3,4-dihydrocarbostyril

Colorless needle-like crystals (from ethanol-acetone-chloroform)
Melting point: 174°–175° C.

EXAMPLE 212

6-{4-[4-(2,3-Dimethylphenyl)-1-piperazinyl]-1-butenyl}-3,4-dihydrocarbostyril

Colorless prism-like crystals (from ethanol-acetone-chloroform)
Melting point: 175°–176° C.

EXAMPLE 213

6-{4-[4-(2-Chloro-6-methylphenyl)-1-piperazinyl]-1-butenyl}-3,4-dihydrocarbostyril Colorless prism-like crystals (from ethanol-acetone-chloroform)
Melting point: 179°–180° C.

EXAMPLE 214

6-{3-[4-(4-Ethoxycarbonylphenyl)-1-piperazinyl]-1-propenyl}-3,4 -dihydrocarbostyril Colorless needle-like crystals (from ethanol-chloroform)
Melting point: 190°–192° C.

EXAMPLE 215

6-{4-[4-(4-Methylthiophenyl)-1-piperazinyl]-1-butenyl}-3,4-dihydrocarbostyril

Colorless needle-like crystals (from ethanol-chloroform)
Melting point: 175.5°–177° C.

EXAMPLE 216

6-{3-[4-(2-Chlorophenyl)-1-piperazinyl]-1-propenyl}-3,4-dihydrocarbostyril

Colorless prism-like crystals (from ethanol-chloroform)
Melting point: 151.5°–152.5° C.

EXAMPLE 217

6-{3-[4-(3-Chlorophenyl)-1-piperazinyl]-1-propenyl}-3,4-dihydrocarbostyril

Colorless prism-like crystals (from ethanol-chloroform)
Melting point: 163°–164° C.

EXAMPLE 218

6-{3-[4-(4-Chlorophenyl)-1-piperazinyl]-1-propenyl}-3,4-dihydrocarbostyril

Colorless prism-like crystals (from ethanol-chloroform)
Melting point: 224.5°–225.5° C.

EXAMPLE 219

6-{3-[4-(2-Fluorophenyl)-1-piperazinyl]-1-propenyl}-3,4-dihydrocarbostyril

Colorless prism-like crystals (from ethanol-chloroform)
Melting point: 188.5°–190° C.

EXAMPLE 220

6-{3-[4-(2-Ethoxyphenyl)-1-piperazinyl]-1-propenyl}-3,4-dihydrocarbostyril

Colorless needle-like crystals (from methanol-chloroform)
Melting point: 203°–204° C.

EXAMPLE 221

6-{4-[4-(2-Ethoxyphenyl)-1-piperazinyl]-1-butenyl}-3,4-dihydrocarbostyril

Colorless needle-like crystals (from ethanol-chloroform)
Melting point: 205°–206° C.

5[3-(4-Phenyl-1-piperazinyl)-1-propenyl]-3,4-dihydrocarbostyril

Colorless prism-like crystals (from methanol)
Melting point: 177°–180° C.

EXAMPLE 222

1.57 Grams of 6-[1-hydroxy-4-(4-phenyl-1-piperazinyl-butyl]-3,4-dihydrocarbostyril and 0.2 g of palladium black were suspended in 100 ml of dioxane, then 10 ml of concentrated hydrochloric acid was added thereto and the mixture was catalytically hydrogenated under 1.5–3.0 kg/cm$^2$ of hydrogen gas at 80°–90° C. The catalyst was removed by filtration and the filtrate was dried under a reduced pressure. To the residue thus obtained were added 10N-NaOH and ether and the mixture was stirred at a room temperature for 30 minutes. The crystals formed were collected by filtration and separated by a silica-gel chromatography, then recrystallized from isopropanol-diisopropyl ether to obtain 6-[4-(4-phenyl-1-piperazinyl)butyl]-3,4-dihydro-carbostyril.

Yield: 0.60 g (40%). Colorless prism-like crystals.
Melting point: 151°–152° C.

By a method similar to that described in Example 222, there were obtained compounds of Examples 223–239 as follows:

EXAMPLE 223

6-{4-[4-(3-Methylphenyl)-1-piperazinyl]butyl)-3,4-dihydrocarsbostyril

Colorless flake-like crystals (isopropyl alcohol-diisopropyl ether)
Melting point: 138.5°–139.5° C.

EXAMPLE 224

6-{4-[4-(2,3-Dimethylphenyl)-1-piperazinyl]butyl}-3,4-dihydrocarbostyril monohydrochloride Colorless plate-like crystals (from methanol)
Melting point: 234°–235° C.

EXAMPLE 225

6-[4-(4-Phenyl-1-piperazinyl)butyl]-3,4-dihydrocarbostyril

Colorless prism-like crystals (from isopropyl alcohol-diisopropyl ether)
Melting point: 150.5°–151.5° C.

EXAMPLE 226

6-{4-[4-(2-Chlorophenyl)-1-piperazinyl]butyl}-3,4-dihydrocarbostyril

Colorless prism-like crystals (from isopropyl alcohol-diisopropyl ether)
Melting point: 128.5°–129.5° C.

EXAMPLE 227

6-{4-[4-(3-Chlorophenyl)-1-piperazinyl]butyl}-3,4-dihydrocarbostyril

Colorless plate-like crystals (from isopropyl alcohol-diisopropyl ether)
Melting point: 149°–150° C.

EXAMPLE 228

6-{3-[4-(3-Chlorophenyl)-1-piperazinyl]propyl}-3,4-dihydrocarbostyril

Colorless plate-like crystals (from isopropyl alcohol-diisopropyl ether)
Melting point: 141.5°–142.5° C.

EXAMPLE 229

6-{3-[4-(2-Ethoxyphenyl)-1-piperazinyl]propyl}-3,4-dihydrocarbostyril

Colorless prism-like crystals (from diethyl ether)
Melting point: 122°–123° C.

EXAMPLE 230

6-{4-[4-(2-Ethoxyphenyl)-1-piperazinyl]butyl}-3,4-dihydrocarbostyril

Colorless prism-like crystals (from isopropyl alcohol-diisopropyl ether)
Melting point: 131.5°–132.5° C.

EXAMPLE 231

6-{3-[4-(3-Methylphenyl)-1-piperazinyl]propyl}-3,4-dihydrocarbostyril

Colorless needle-like crystals
Melting point: 116°–117° C.

EXAMPLE 232

6-{4-[4-(4-Methylphenyl)-1-piperazinyl]butyl}-3,4-dihydrocarbostyril

Colorless prism-like crystals (from isopropyl alcohol-diisopropyl ether)
Melting point: 160°–161° C.

EXAMPLE 233

6-{3-[4-(2-Methoxyphenyl)-1-piperazinyl]propyl}-3,4-dihydrocarbostyril

Colorless prism-like crystals (from isopropyl alcohol-diisopropyl ether)
Melting point: 145°–146° C.

EXAMPLE 234

1-(3-Phenylpropyl)-6{3-[4-(2-ethoxyphenyl)-1-piperazinyl]-propyl}-3,4-dihydrocarbostyril monooxalate Colorless plate-like crystals (from acetone-water)
Melting point: 117°–118° C.

EXAMPLE 235

1-Isopentyl-6-{3-[4-(2-ethoxyphenyl)-1-piperazinyl]-propyl}-3,4-dihydrocarbostyril monooxalate Colorless plate-like crystals (acetone-water)
Melting point: 150°–151° C.

EXAMPLE 236

6-{4-[4-(2-Hydroxyphenyl)-1-piperazinyl]butyl}-3,4-dihydrocarbostyril

Colorless needle-like crystals (from ethanol)
Melting point: 167°–169° C.

EXAMPLE 237

6-[3-(4-Phenyl-1-piperazinyl)propyl]-3,4-dihydrocarbostyril

Colorless plate-like crystals (from isopropyl alcohol-diisopropyl ether)
Melting point: 136.5°–137.5° C.

EXAMPLE 238

6-{3-[4-(4-Nitrophenyl)-1-piperazinyl]propyl}-3,4-dihydrocarbostyril

Yellowish needle-like crystals (from isopropyl alcohol)
Melting point: 189°–192° C.

EXAMPLE 239

6-[4-(4-Phenyl-1-piperazinyl)butyl]carbostyril monohydrochloride

Colorless needle-like crystals (from methanol)
Melting point: 233°–235° C.

5-[3-(4-Phenyl-1-piperazinyl)propyl]-3,4-dihydrocarbostyril monohydrochloride

Colorless needle-like crystals (from ethanol-water)
Melting point: 230°–233° C.

EXAMPLE 240

2.5 Grams of 6-(4-chlorobutyl)-3,4-dihydrocarbostyril and 1.8 g of sodium iodide were mixed in 80 ml of acetone and stirred at 50° C. for 2 hours. Then to the reaction mixture was added 80 ml of dimethylformamide and the acetone was removed by distillation, and 2.0 g of 4-(4-tolyl)piperazine and 2.0 g of triethylamine were added to the reaction mixture, and stirred at 70°–80° C. for 5 hours. The reaction mixture was concentrated under a reduced pressure to obtain a residue. To the residue was added 50 ml of 5%-sodium hydrogencarbonate aqueous solution and stirred. The precipitates thus formed were collected by filtration, washed with water and dried. Recrystallization from isopropanol-diisopropyl ether, there were obtained 3.1 g of 6-{4-[4-(4-tolyl)-1-piperazinyl]butyl}-3,4-dihydrocarbostyril in colorless prism-like crystals, having the melting point of 160°–161° C.

By a method similar to that described in Example 240, there were obtained compounds of Examples 241–256 as follows:

EXAMPLE 241

6-[4-(4-Phenyl-1-piperazinyl)butyl]-3,4-dihydro-carbostyril

Colorless prism-like crystals (from isopropyl alcohol-diisopropyl ether)
Melting point: 151°–152° C.

EXAMPLE 242

6-{4-[4-(3-Methylphenyl)-1-piperzinyl]butyl}-3,4-dihydrocarbostyril

Colorless flake-like crystals (from isopropyl alcohol-diisopropyl ether)
Melting point: 138.5°–139.5° C.

EXAMPLE 243

6-{-4-[4-(2,3-Dimethylphenyl)-1-piperazinyl]-butyl}-3,4dihydrocarbostyril monohydrochloride Colorless plate-like crystals (from methanol)
Melting point: 243°–235° C.

EXAMPLE 244

6-[4-(4-Phenyl-1-piperazinyl)butyl]-3,4-dihydrocarbostyril

Colorless prism-like crystals (from isopropyl alcohol-diisopropyl ehter)
Melting point: 150.5°–151.5° C.

EXAMPLE 245

6-{4-[4-(2-Chlorophenyl)-1-piperazinyl]butyl}-3,4-dihydrocarbostyrl

Colorless prism-like crystals (from isopropyl alcohol-diisopropyl ether)
Melting point: 128.5°–129.5° C.

EXAMPLE 246

6-{4-[4-(3-Chlorophenyl)-1-piperazinyl]butyl}-dihydrocarbostyril

Colorless plate-like crystals (from isopropyl alcohol-diisopropyl ether)
Melting point: 149°–150° C.

EXAMPLE 247

6-{3-[4-(3-Chlorophenyl)-1-piperazinyl]propyl}-3,4-dihydrocarbostyril

Colorless plate-like crystals (from isopropyl alcohol-diisopropyl ether)
Melting point: 141.5°–142.5° C.

EXAMPLE 248

6-{3-[4-(2-Ethoxyphenyl)-1-piperazinyl]propyl}-3,4-dihydrocarbostyril

Colorless prism-like crystals (from diethyl ether)
Melting point: 122°–123° C.

EXAMPLE 249

6-{4-[4-(2-Ethoxyphenyl)-1-piperazinyl]butyl}-3,4-dihydrocarbostyril

Colorless prism-like crystals (from iropropyl alcohol-diisopropyl ether)
Melting point: 131.5°–132.5° C.

EXAMPLE 250

6-{3-[4-(3-Methylphenyl)-1-piperazinyl]propyl}-3,4-dihydrocarbostyril

Colorless needle-like crystals
Melting point: 116°–117° C.

EXAMPLE 251

6-{3-[4-(2-Methoxyphenyl)-1-piperazinyl]propyl}-3,4-dihydrocarbostyril

Colorless prism-like crystals (from isopropanol-diisopropyl ether)
Melting point: 145°–146° C.

EXAMPLE 252

1-(3-Phenylpropyl)-6-{3-[4-(2-ethoxyphenyl)-piperazinyl]propyl}-3,4-dihydrocarbostyril monooxalate Colorless plate-like crystals (from acetone-water)
Melting point: 117°–118° C.

EXAMPLE 253

1-Isopentyl-6-{3-[4-(2-ethoxyphenyl)-1-piperazinyl]propyl}-3,4-dihydrocarbostyril monooxalate Colorless plate-like crystals (from acetone-water)
Melting point: 150°–151° C.

EXAMPLE 254

6-{4-[4-(2-Hydroxyphenyl)-1-piperazinyl]butyl}-3,4-dihydrocarbostyril

Colorless needle-like crystals (from ethanol)
Melting point: 167°–169° C.

EXAMPLE 255

6-[3-(4-Phenyl-1-piperazinyl)propyl]-3,4-dihydro-carbostyril

Colorless plate-like crystals (isopropyl alcohol-diisorpopyl ether)

EXAMPLE 256

6-{3-[4-(4-Nitrophenyl)-1-piperazinyl]propyl}-3,4-dihydrocarbostyril

Yellowish needle-like crystals (from isopropanol)
Melting point: 189°–192° C.

EXAMPLE 257

6-[4-(4-Phenyl-1-piperazinyl)butyl]carbostyril monohydrochloride

Colorless needle-like crystals (from methanol)
Melting point: 233°–235° C.

5-[3-(4-Phenyl-1-piperazinyl)propyl]-3,4-dihydrocarbostyril monohydrochloride

Colorless needle-like crystals (from ethanol-water)
Melting point: 230°–233° C.

EXAMPLE 258

1.0 Gram of 6-{4-[4-(4-Methylphenyl)-1-piperazinyl]-1-butenyl}-3,4-dihydrocarbostyril and 0.2 g of palladium black were suspended in 100 ml of dioxane and the mixture was catalytically hydrogenated under an ordinary pressure at an ordinary temperature. The catalyst was removed by filtration and the filtrate was dried under a reduced pressure. The residue was recrsytallized from isopropanol-diisopropyl ether to obtain 6-{4-[4-(4-methylphenyl)piperazinyl]-butyl}-3,4-dihydrocarbostyril in colorless prism-like crystals. Yield: 0.7 g. Melting point: 160°–161° C.

EXAMPLE 259

2.3 Grams of 6-{3-[4-(2-methoxyphenyl)-1-piperazinyl]-1-propenyl}-3,4-dihydrocarbostyril and 0.2 g of platinum black were suspended in 100 ml of methanol and the suspension was catalytically hydrogenated under 2 to 4 atmospheric pressure of hydrogen gas at a normal temperature. After the catalyst was removed by filtration, the filtrate was dried under a reduced pressure. The residue was recrystallized from isopropanol-diisopropyl ether to obtain 6-{3-[4-(2-methoxyphenyl)-1-piperazinyl]propyl}-3,4-dihydrocarbostyril in colorless prism-like crystals. Yield: 1.3 g. Melting point: 145°–146° C.

EXAMPLE 260

0.37 Gram of 6-{4-[4-(2-chlorophenyl)-1-piperazinyl]-1-butenyl}-3,4-dihydrocarbostyril and 0.1 g of 10%-palladium carbon were suspended in 40 ml of water, then 0.2 ml of concentrated hydrochloric acid was added to the suspension and the mixture was catalytically hydrogenated under 5 atmospheric pressure of hydrogen gas at an ordinary temperature. The catalyst was removed by filtration and to the filtrate were added 10N-NaOH and ether and stirred at a room temperature for 30 minutes. The crystals thus precipitated were collected by filtration and recrystallized from isopropanol to obtain 6-{4-[4-(2-chlorophenyl)-1-piperazinyl]-butyl}-3,4-dihydrocarbostyril in colorless prism-like crystals.

Yield: 0.27 g. Melting point: 129°–130° C.

By a method similar to that described in Example 260, there were obtained compounds of Examples 261–277 as follows:

EXAMPLE 261

6-[4-(4-Phenyl-1-piperazinyl)butyl]-3,4-dihydrocarbostyril

Colorless prism-like crystals (from isopropanol-diisopropyl ether)
Melting point: 151°–152° C.

EXAMPLE 262

6-{4-[4-(3-Methylphenyl)-1-piperazinyl]butyl}-3,4-dihydrocarbostyril

Colorless flake-like crystals (from isopropanol-diisopropyl ether)
Melting point: 138.5°–139.5° C.

EXAMPLE 263

6-{3-[4-(2,3-Dimethylphenyl)-1-piperazinyl]propyl}-3,4-dihydrocarbostyril monohydrochloride Colorless plate-like crystals (from methanol)
Melting point: 234°–235° C.

EXAMPLE 264

6-[4-(4-Phenyl-1-piperazinyl)butyl]-3,4-dihydro-carbostyril

Colorless prism-like crystals (from isopropanol-diisopropyl ether)
Melting point: 150.5°–151.5° C.

EXAMPLE 265

6-{4-[4-(3-Chlorophenyl)-1-piperazinyl]butyl}-3,4-dihydrocarbostyril

Colorless plate-like crystals (from isopropanol-diisopropyl ether)
Melting point: 149°–150° C.

EXAMPLE 266

6-{3-[4-(3-Chlorophenyl)-1-piperazinyl]propyl}-3,4-dihydrocarbostyril

Colorless plate-like crystals (from isopropanol-diisopropyl ether)
Melting point: 141.5°–142.5° C.

EXAMPLE 267

6-{3-[4-(2-Ethoxyphenyl)-1-piperazinyl]propyl}-3,4-dihydrocarbostyril

Colorless prism-like crystals (from diethyl ether)
Melting point: 122°–123° C.

EXAMPLE 268

6-{4-[4-(2-Ethoxyphenyl)-1-piperazinyl]butyl}-3,4-hydrocarbostyril

Colorless prism-like crystals (from isopropanol-diisopropyl ether)
Melting point: 131.5°–132.5° C.

EXAMPLE 269

6-{3-[4-(3-Methylphenyl)-1-piperazinyl]propyl}-3,4-dihydrocarbostyril

Colorless needle-like crystals
Melting point: 116°–117° C.

EXAMPLE 270

6-{4-[4-(4-Methylphenyl)-1-piperazinyl]butyl}-3,4-dihydrocarbostyril

Colorless prism-like crystals (from isopropanol-diisopropyl ether)
Melting point: 160°–161° C.

EXAMPLE 271

6-{3-[4-(2-Methoxyphenyl)-1-piperazinyl]propyl}-3,4-dihydrocarbostyril

Colorless prism-like crystals (from isoprpanol-diisopropyl ether)
Melting poing: 145°–146° C.

EXAMPLE 272

1-(3-Phenylpropyl)-6-{3-[4-(2-ethoxyphenyl)-1-piperazinyl]-propyl}-3,4-dihydrocarbostyril monooxalate Colorless plate-like crystals (from acetone-water)
Melting point: 117°–118° C.

EXAMPLE 273

1-Isopentyl-6-{3-[4-(2-ethoxyphenyl)-1-piperazinyl]-propyl}-3,4-dihydrocarbostyril monooxalate Colorless plate-like crystals (from acetone-water)
Melting point: 150°–151° C.

EXAMPLE 274

6-{4-[4-(2-Hydroxyphenyl)-1-piperazinyl]butyl}-3,4-dihydrocarbostyril

Colorless needle-like crystals (from ethanol)
Melting point: 167°–169° C.

EXAMPLE 275

6-[3-(4-Phenyl-1-piperazinyl)propyl]-3,4-dihydrocarbostyril

Colorless plate-like crystals (from isopropanol-diisopropyl ether)
Melting point: 136.5°–137.5° C.

EXAMPLE 276

6-{3-[4-(4-Nitrophenyl)-1-piperazinyl]propyl}-3,4-dihydrocarbostyril

Yellow needle-like crystals (from isopropanol)
Melting point: 189°–192° C.

EXAMPLE 277

6-[4-(4-Phenyl-1-piperazinyl)butyl]carbostyril monohydrochloride

Colorless needle-like crystals (from methanol)
Melting piont: 233°–235° C.

5-[3-(4-Phenyl-1-piperazinyl)propyl]-3,4-dihydrocarbostyril monohydrochloride

Colorless needle-ike crystals (from ethanol-water)
Melting point: 230°–233° C.

EXAMPLE 278

2.0 Grams of 6-{1-oxo-3-[4-(2-ethoxyphenyl)-1-piperazinyl]propyl}-3,4-dihydrocarbostyril monohydrochloride and 0.4 g of palladium black were suspended in 100 ml of water and the suspension was catalytically hydrogenated under 3 atmospheric pressure of hydrogen gas at 80° C. Then 5 ml of concentrated hydrochloric acid was added to the reaction mixture and further catalytically hydrogenated. The catalyst was removed by filtration and to the filtrate thus obtained was neutralized by adding 10N-NaOH aqueous solution, then extracted with chloroform. The chloroform was removed by distillation and the residue thus obtained was purified by column chromatography. Recrystallized from ether to obtain 6-{3-[4-(2-ethoxyphenyl)-1-piperazinyl]propyl}-3,4-dihydrocarbostyril in colorless prism-like crystals. Yield: 0.8 g.
Melting point: 122°–123° C.

By a method similar to that described in Example 278, there were obtained compounds of Examples 279–294 as follows:

EXAMPLE 279

6-[4-(4-Phenyl-1-piperazinyl)butyl]-3,4-dihydrocarbostyril

Colorless prism-like crystals (from isopropanol-diisopropyl ether)
Melting point: 151°–152° C.

EXAMPLE 280

6-{4-[4-(3-Methylphenyl)-1-piperazinyl]butyl}-3,4-dihydrocarbostyril

Colorless flake-like crystals (from isopropanol-diisopropyl ether)
Melting point: 138.5°–139.5° C.

EXAMPLE 281

6-{4-[4-(2,3-Dimethylphenyl)-1-piperazinyl]butyl}-3,4-dihydrocarbostyril monohydrochloride Colorless plate-like crystals (from methanol)
Melting point: 234°–235° C.

EXAMPLE 282

6-[4-(4-Phenyl-1-piperazinyl)butyl]-3,4-dihydro-carbostyril

Colorless prism-like crystals (from isopropanol-diisopropyl ether)
Melting point: 150.5°–151.5° C.

EXAMPLE 283

6-{4-[4-(2-Chlorophenyl)-1-piperazinyl]butyl}-3,4-dihydrocarbostyril

Colorless prism-like crystals (from isopropanol-diisopropyl ether)
Melting point: 128.5°–129.5° C.

EXAMPLE 284

6-{4-[4-(3-Chlorophenyl)-1-piperazinyl]butyl}-3,4-dihydrocarbostyril

Colorless plate-like crystals (from isopropanol-diisopropyl ether)
Melting point: 149°–150° C.

EXAMPLE 285

6-{3-[4-(3-Chlorophenyl)-1-piperazinyl]propyl}-3,4-dihydrocarbostyril

Colorless plate-like crystals (from isopropanol-diisopropyl ether)
Melting point: 141.5°–142.5° C.

EXAMPLE 286

6-{4-[4-(2-Ethoxyphenyl)-1-piperazinyl]butyl}-3,4-dihydrocarbostyril

Colorless prism-like crystals (from isopropanol-diisopropyl ether)
Melting point: 131.5°–132.5° C.

EXAMPLE 287

6-{3-[4-(3-Methylphenyl)-1-piperazinyl]propyl}-3,4-dihydrocarbostyril

Colorless needle-like crystals
Melting point: 116°–117° C.

EXAMPLE 288

6-{4-[4-(4-Methylphenyl)-1-piperazinyl]butyl}-3,4-dihydrocarbostyril

Colorless prism-like crystals (from isopropanol-diisopropyl ether)
Melting point: 160°–161° C.

EXAMPLE 289

6-{3-[4-(2-Methoxyphenyl)-1-piperazinyl]propyl}-3,4-dihydrocarbostyril

Colorless prism-like crystals (from isopropanol-diisopropyl ether)
Melting point: 145°–146° C.

EXAMPLE 290

1-(3-Phenylpropyl)-6-{3-[4-(2-ethoxyphenyl)-1-piperazinyl]-propyl}-3,4-dihydrocarbostyril monooxalate Colorless plate-like crystals (from acetone-water)
Melting point: 117°–118° C.

EXAMPLE 291

1-Isopentyl-6-{3-[4-(2-ethoxyphenyl)-1-piperazinyl]-propyl}-3,4-dihydrocarbostyril monooxalate Colorless plate-like crystals
Melting point: 150°–151° C.

EXAMPLE 292

6-{4-[4-(2-Hydroxyphenyl)-1-piperazinyl]butyl}-3,4-dihydrocarbostyril

Colorless needle-like crystals (from ethanol)
Melting point: 167°–169° C.

EXAMPLE 293

6-[3-(4-Phenyl-1-piperazinyl)propyl]-3,4-dihydrocarbostyril

Colorless plate-like crystals (from isopropanol-diisopropyl ether)
Melting point: 136.5°–137.5° C.

EXAMPLE 294

6-{3-[4-(4-Nitrophenyl)-1-piperazinyl]propyl}-3,4-dihydrocarbostyril

Yellowish needle-like crystals (from isopropanol)
Melting point: 189°–192° C.

5-[3-(4-Phenyl-1-piperazinyl)propyl]-3,4-dihydrocarbostyril

Colorless needle-like crystals (from ethanol-water)
Melting point: 230°–233° C.

EXAMPLE 295

2.88 Grams of 6-(4-morpholinobutyl)-3,4-dihydrocarbostyril and 10 ml of aniline were enclosed in a sealed tube and heated at 170°–200° C. for 5 hours. The reaction mixture was concentrated under a reduced pressure by removing aniline and the residue thus obtained was separated and purified by a silica-gel chromatography. Recrystallized from iropropanoldiisopropyl ether to obtain ether to obtain 0.36 g of 6-[4-(4-phenyl-1-piperazinyl)butyl-]3,4-dihydrocarbostyril in colorless prism-like crystals having the melting point of 151°–152° C.

By a method similar to that described in Example 295, there were obtained compounds of Examples 296–342 as follows:

EXAMPLE 296

6-{3-[4-(2-Methoxyphenyl)-1-piperazinyl]-1-propenyl}-3,4-dihydrocarbostyril

Colorless needle-like crystals
Melting point: 174°–175° C.

EXAMPLE 297

6-{4-[4-(2,3-Dimethylphenyl)-1-piperazinyl]-1-butenyl}-3,4-dihydrocarbostyril

Colorless prism-like crystals
Melting point: 175°–176° C.

EXAMPLE 298

6-[3-(4-Phenyl-1-piperazinyl)-1-propenyl]-3,4-dihydrocarbostyril

Colorless prism-like crystals (from ethanol)
Melting point: 186°–187° C.

EXAMPLE 299

6-[4-(4-Phenyl-1-piperazinyl)-1-butenyl]-3,4-dihydrocarbostyril

Colorless prism-like crystals (from ethanol-chloroform)
Melting point: 187°–188° C.

EXAMPLE 300

6-{3-[4-(2-Chlorophenyl)-1-piperazinyl]-1-propenyl}-3,4-dihydrocarbostyril

Colorless prism-like crystals (from ethanol-chloroform)
Melting point: 151.5°–152.5° C.

EXAMPLE 301

6-{3-[4-(3-Chlorohenyl)-1-piperazinyl)-1-propenyl}-3,4-dihydrocarbostyril

Colorless prism-like crystals (from ethanol-chloroform)
Melting point: 163°–164° C.

EXAMPLE 302

6-{3-[4-(4-Chlorophenyl)-1-piperazinyl]-1-propenyl}-3,4-dihydrocarbostyril

Colorless prism-like crystals (from ethanol-chloroform)
Melting point: 224.5°–225.5° C.

EXAMPLE 303

6-{3-[4-(2-Fluorophenyl)-1-piperazinyl]-1-propenyl}-3,4-dihydrocarbostyril

Colorless prism-like crystals (from ethanol-chloroform)
Melting point: 188.5°–190° C.

EXAMPLE 304

6-{3-[4-(2-Ethoxyphenyl)-1-piperazinyl]-1-propenyl}-3,4-dihydrocarbostyril

Colorless needle-like crystals (from methanol-chloroform)
Melting point: 203°–204° C.

EXAMPLE 305

6-{4-[4-(2-Ethoxyphenyl)-1-piperazinyl]-1-butenyl}-3,4-dihydrocarbostyril

Colorless needle-like crystals (from ethanol-chloroform)
Melting point: 205°–206° C.

EXAMPLE 306

6-{3-[4-(3-Methylphenyl)-1-piperazinyl]-1-propenyl}-3,4-dihydrocarbostyril

Colorless prism-like crystals (from ethanol)(
Melting point: 167°–168° C.

EXAMPLE 307

6-[4-(4-Phenyl-1-piperazinyl)butyl]carbostyril monohydrochloride

Colorless needle-like crystals (from methanol)
Melting point: 233°–235° C.

EXAMPLE 308

6-{4-[4-(3-Methylphenyl)-1-piperazinyl]-1-butenyl}-3,4-dihydrocarbostyril

Colorless prism-like crystals (from ethanol)
Melting point: 171.5°–172.5° C.

EXAMPLE 309

6-{4-[4-(4-Methylphenyl)-1-piperazinyl]-1-butenyl}-3,4-dihydrocarbostyril

Colorless prism-like crystals (from ethanol-chloroform)
Melting point: 202°–203° C.

EXAMPLE 310

6-{3-[4-(2-Methoxyphenyl)-1-piperazinyl]-1-propenyl}-3,4-dihydrocarbostyril

Colorless needle-like crystals (from ethanol-acetone-chloroform)
Melting point: 174°–175° C.

EXAMPLE 311

6-{4-[4-(2,3-Dimethylphenyl)-1-piperazinyl]-1-butenyl}-3,4-dihydrocarbostyril

Colorless prism-like crystals (from ethanol-acetone-chloroform)
Melting point: 175°–176° C.

EXAMPLE 312

6-{4-[4-(2-Chloro-6-methylphenyl)-1-piperazinyl]-1-butenyl}-3,4-dihydrocarbostyril Colorless prism-like crystals (from ethanol-acetone-chloroform)
Melting point: 179°–180° C.

EXAMPLE 313

6-{3-[4-(4-Ethoxycarbonylphenyl)-1-piperazinyl]-1-propenyl}-3,4-dihydrocarbostyril Colorless needle-like crystals (from ethanol-chloroform)
Melting point: 190°–192° C.

EXAMPLE 314

6-{4-[4-(4-Methylthiophenyl)-piperazinyl]-1-butenyl}-3,4-dihydrocarbostyril

Colorless needle-like crystals (from ethanol-chloroform)
Melting pint: 175.5°–177° C.

EXAMPLE 315

6-{4-[4-(4-Acetylphenyl)-1-piperazinyl]-1-butenyl}-3,4-dihydrocarbostyril

Colorless prism-like crystals (from ethanol-chloroform)
Melting point: 213°–215° C.

EXAMPLE 316

6-{3-[4-(4-Cyanophenyl)-1-piperazinyl]-1-propenyl}-3,4-dihydrocarbostyril

Colorless prism-like crystals (from ethanol-chloroform)
Melting point: 196°–198° C.

EXAMPLE 317

6-{3-[4-(2-Hydroxyphenyl)-1-piperazinyl]-1-propenyl}-3,4-dihydrocarbostyril

Colorless prism-like crystals (ethanol-chloroform)
Melting point: 192°–194° C.

EXAMPLE 318

1-Methyl-6-{3-[4-(3-methylphenyl)-1-piperazinyl]-1-propenyl}-3,4-dihydrocarbostyril monooxalate Light yellow needle-like crystals (from ethanol)
Melting point: 178°–179° C.

EXAMPLE 319

1-Benzyl-6-{3-[4-(3-methylphenyl)-1-piperazinyl]-propenyl}-3,4-dihydrocarbostyril monooxalate Colorless needle-like crystals (from ethanol)
Melting point: 176°–179° C.

EXAMPLE 320

1-Allyl-6-{3-[4-(3-methylphenyl)-1-piperazinyl]-1-propenyl}-3,4-dihydrocarbostyril monooxalate Colorless needle-like crystals (from ethanol)
Melting point: 167°–168° C.

EXAMPLE 321

1-(2-Propynyl)-6-}3-[4-(3-methylphenyl)-1-piperazinyl]propenyl}-3,4-dihydrocarbostyril monooxalate Colorless powdery crystals (from ethanol)
Melting point: 158°–160° C.

EXAMPLE 322

6-{3-[4-(3-Carboxyphenyl)-1-piperazinyl]-1-propenyl}-3,4-dihydrocarbostyril monohydrochloride Colorless needle-like crystals (from ethanol-water)
Melting point: 264°–266° C.

EXAMPLE 323

6-{4-[4-(3,4-Methylenedioxyphenyl)-1-piperazinyl]-1-butenyl}-3,4-dihydrocarbostryil monohydrochloride.

Colorless needle-like crystals (from methanol)
Melting point: 226°–228° C.

EXAMPLE 324

6-[3-Methyl-3(4-phenyl-1-piperazinyl)-1-propenyl]-3,4-dihydrocarbostyril

Colorless prism-like crystals (from ethanol-chloroform)
Melting point: 172°–173° C.

EXAMPLE 325

6{4-[4-(3-Methylphenyl)-1-piperazinyl]butyl}-3,4-dihydrocarbostyril

Colorless flake-like crystals (from isopropanol-diisopropyl ether)
Melting point: 138.5°–139.5° C.

EXAMPLE 326

6-{4-[4-(2,3-Dimethylphenyl)-1-piperazinyl]butyl}-3,4-dihydrocarbostyril monohydrochloride Colorless plate-like crystals (from methanol)
Melting point: 234°–235° C.

EXAMPLE 327

6-[4-(4-Phenyl-1-piperazinyl)butyl]-3,4-dihydro-carbostyril

Colorless prism-like crystals (from isopropanol-diisopropyl ether)
Melting point: 150.5°–151.5° C.

EXAMPLE 328

6-{4-[4-(2-Chlorophenyl)-1-piperazinyl]butyl}-3,4-dihydrocarbostyril

Colorless prism-like crystals (from isopropanol-diisopropyl ether)
Melting point: 128.5°–129.5° C.

EXAMPLE 329

6-{4-[4-(3-Chlorophenyl)-1-piperazinyl]butyl}-3,4-dihydrocarbostyril

Colorless plate-like crystals (from isopropanol-diisopropyl ether)
Melting point: 149°–150° C.

EXAMPLE 330

6-{3-[4-(3-Chorophenyl)-1-piperazinyl]propyl}-3,4-dihydrocarbostyril

Colorless plate-like crystals (from isopropanol-diisopropyl ether)
Melting point: 141.5°–142.5° C.

EXAMPLE 331

6-{3-[4-(2-Ethoxyphenyl)-1-piperazinyl]propyl)-3,4-dihydrocarbostyril

Colorless prism-like crystals (from diethyl ether)
Melting point: 122°–123° C.

EXAMPLE 332

6-{4-[4-(2-Ethoxyphenyl)-1-piperazinyl]butyl)-3,4-dihydrocarbostyril

Colorless prism-like crystals (from isopropanol-diisoproyl ether)
Melting point: 131.5°–132.5° C.

EXAMPLE 333

6-{3-[4-(3-Methylphenyl)-1-piperazinyl]propyl}-3,4-dihydrocarbostyril

Colorless needle-like crystals
Melting point: 116°–117° C.

EXAMPLE 334

6-{4-[4-(4-Methylphenyl)-1-piperazinyl]butyl}-3,4-dihydrocarbostyril

Colorless prism-like crystals (from isopropanol-diisopropyl ether)
Melting point: 160°–161° C.

EXAMPLE 335

6-{3-[4-(2-Methoxyphenyl)-1-piperazinyl]propyl}-3,4-dihydrocarbostyril

Colorless prism-like crystals (from isopropanol-diisopropyl ether)
Melting point: 145°–146° C.

EXAMPLE 336

1-(3-Phenylpropyl)-6-{3-[4-(2-ethoxyphenyl)-1-piperazinyl]-propyl}-3,4-dihydrocarbostyril monooxalate.

Colorless plate-like crystals (from acetone-water)
Melting point: 117°–118° C.

EXAMPLE 337

1-Isopentyl-6-{3-[4-(2-ethoxyphenyl)-1-piperazinyl]-propyl}-3,4-dihydrocarbostyril monooxalate Colorless plate-like crystals (from acetone-water)
Melting point: 150°–151° C.

EXAMPLE 338

6-{4-[4-(2-Hydroxyphenyl)-1-piperazinyl]butyl}-3,4-dihydrocarbostyril

Colorless needle-like crystals (from ethanol)
Melting point: 167°–169° C.

EXAMPLE 339

6-[3-(4-Phenyl-1-piperazinyl)propyl]-3,4-dihydrocarbostyril

Colorless plate-like crystals (from isopropanol-diisopropyl ether)
Melting point: 136.5°–137.5° C.

EXAMPLE 340

6-{3-[4-(4-Nitrophenyl)-1-piperazinyl]propyl}-3,4-dihydrocarbostyril
Yellowish needle-like crystals (from isopropanol)
Melting point: 189°–192° C.

EXAMPLE 341

6-}4-[4-(2-Ethoxyphenyl)-1-piperazinyl]1-butenyl}-carbostyril

Colorless needle-like crystals (from methanol)
Melting point: 225°–228° C.

EXAMPLE 342

6-[4-(4-Phenyl-1-piperazinyl)-1-butenyl]carbostyril monohydrochloride

Colorless needle-like crystals (from methanol)
Melting point: 233°–235° C.

5-[3-(4-Phenyl-1-piperazinyl)-1-propenyl]-3,4-dihydrocarbostyril

Colorless prism-like crystals (from methanol)
Melting point: 177°–180° C.

5-[3-(4-Phenyl-1-piperazinyl)propyl]-3,4-dihydrocarbostyril monohydrochloride

Colorless needle-like crystals (from ethanol-water)
Melting point: 220°–233° C.

EXAMPLE 343

2.87 Grams of 6-(3-piperazinylpropyl)-3,4-dihydrocarobostyril, 2.0 g of p-nitroaniline, 0.8 g of potassium carbonate and 0.2 g of copper power were mixed in 80 ml of 3-methoxybutanol and refluxed by heating for 5 hours. Then 3 g of activated carbon was added to the reaction mixture and filtered with Celite, then the mother liquor was concentrated under a reduced pressure to obtain a residue. The residue was purified by a silica-gel chromatography and recrystallized from isopropanol to obtain 0.55 g of 6-{3-[4-(4-nitrophenyl)-1-piperazinyl]propyl}-3,4-dihydrocarbostyril in yellow needle-like crystals, having the melting point of 189°–192° C.

By a method similar to that described in Example 343, there were obtained compounds of Examples 344–389 as follows:

EXAMPLE 344

6-[4-(4-Phenyl-1-piperazinyl)butyl]-3,4-dihydrocarbosytril

Colorless prism-like crystals (from isopropanol-diisopropyl ether)
Melting point: 151°–152° C.

EXAMPLE 345

6-{4-[4-(3-Methylphenyl)-1-piperazinyl]butyl}-3,4-dihydrocarbostyril

Colorless flake-like crystals (from isopropanol-diisopropyl ether)
Melting point: 138.5°–139.5° C.

EXAMPLE 346

6-{4-[4-(2,3-Dimethylphenyl)-1-piperazinyl]butyl}-3,4-dihydrocarbostyril monohydrochloride Colorless plate-like crystals (from methanol)
Melting point: 234°–235° C.

EXAMPLE 347

6-[4-(4-Phenyl-1-piperazinyl(butyl]-3,4-dihydrocarbostyril

Colorless prism-like crystals (from isopropanol-diisopropyl ether)
Melting point: 150.5°–151.5° C.

EXAMPLE 348

6-{4-[4-(2-Chlorophenyl)-1-piperazinyl]butyl}-3,4-dihydrocarbostyril

Colorless prism-like crystals (from isopropanol-diisopropyl ether)
Melting point: 128.5°–129.5° C.

EXAMPLE 349

6-{4-[4-(3-Chlorophenyl)-1-piperazinyl]butyl}-3,4-dihydrocarbostyril

Colorless plate-like crystals (from isopropanol-diisopropyl ether)
Melting point: 149°–150° C.

EXAMPLE 350

6-{3-[4-(3-Chlorophenyl)-1-piperazinyl]propyl}-3,4-dihydrocarbostyril

Colorless plate-like crystals (from isopropanol-diisopropyl ether)
Melting point: 141.5°–142.5° C.

EXAMPLE 351

6-{3-[4-(2-Ethoxyphenyl)-1-piperazinyl]propyl}-3,4-dihydrocarbostyril

Colorless prism-like crystals (from diethyl ether)
Melting point: 122°–123° C.

EXAMPLE 352

6-{4-[4-(2-Ethoxyphenyl)-1-piperazinyl]butyl}-3,4-dihydrocarbostyril

Colorless prism-like crystals (from isopropanol-diisopropyl ether)
Melting point: 131.5°–132.5° C.

EXAMPLE 353

6-{3-[4-(3-Methylphenyl)-1-piperazinyl]propyl-}-3,4-dihydrocarbostyril

Colorless needle-like crystals
Melting point: 116°–117° C.

EXAMPLE 354

6-{4-[4-Methylphenyl)-1-piperazinyl]butyl}-3,4-dihydrocarbostyril

Colorless prism-like crystals (from isopropanol-diisopropyl ether)
Melting point: 160°–161° C.

EXAMPLE 355

6-{3-[4-(2-Methoxyphenyl)-1-piperazinyl]propyl}-3,4-dihydrocarbostyril

Colorless prism-like crystals (from isopropanol-diisopropyl ether)
Melting point: 145°–146° C.

EXAMPLE 356

1-(3-Phenylpropyl)-6-{3-[4-(2-ethoxyphenyl)-1-piperazinyl]propyl}-3,4-dihydrocarbostryil monooxalate Colorless plate-like crystals (from acetone-water)
Melting point: 117°–118° C.

EXAMPLE 357

1-Isopentyl-6-{3-[4-(2-ethoxyphenyl)-1-piperazinyl]propyl}-3,4-dihydrocarbostyril monooxalate Colorless plate-like crystals (from acetone-water)
Melting point: 150°–151° C.

EXAMPLE 358

6-{4-[4-(2-Hydroxyphenyl)-1-piperazinyl]butyl}-3,4-dihydrocarbostyril

Colorless needle-like crystals (from ethanol)
Melting point: 167°–169° C.

EXAMPLE 359

6-[3-(4-Phenyl-1-piperazinyl)propyl]-3,4-dihydrocarbostyril

Colorless plate-like crystals (from isopropanol-diisopropyl ether)
Melting point: 136.5°–137.5° C.

EXAMPLE 360

6-{4-[4-(2-Ethoxyphenyl)-1-piperazinyl]-1-butenyl}-carbostyril

Colorless needle-like crystals (from methanol)
Melting point: 225°–228° C.

EXAMPLE 361

6-[4-(4-Phenyl-1-piperazinyl)-1-butenyl]carbostyril monohydrochloride

Colorless needle-like crystals (from methanol)
Melting point: 233°–235° C.

EXAMPLE 362

6-{3-[4-(2-Methoxyphenyl)-1-piperazinyl]-1-propenyl}-3,4-dihydrocarbostyril

Colorless needle-like crystals
Melting point: 174°–175° C.

EXAMPLE 363

6-{4-[4-(2,3-Dimethylphenyl)-1-piperazinyl]-1-butenyl}-3,4-dihydrocarbostyril

Colorless prism-like crystals
Melting point: 175°–176° C.

EXAMPLE 364

6-[3-(4-Phenyl-1-piperazinyl)-1-propenyl]-3,4-dihydrocarbostyril

Colorless prism-like crystals (from ethanol)
Melting point: 186°–187° C.

EXAMPLE 365

6-[4-(4-Phenyl-1-piperazinyl)-1-butenyl]-3,4-dihydrocarbostyril

Colorless prism-like crystals (from ethanol-chloroform)
Melting point: 187°–188° C.

EXAMPLE 366

6-{3-[4-(2-Chlorophenyl)-1-piperazinyl]-1-propenyl}-3,4-dihydrocarbostyril

Colorless prism-like crystals (from ethanol-chloroform)
Melting point: 151.5°–152.5° C.

EXAMPLE 367

6-{3-[4-(3-Chlorophenyl)-1-piperazinyl]-1-propenyl}-3,4-dihydrocarbostyril

Colorless prism-like crystals (ethanol-chloroform)
Melting point: 163°–164° C.

EXAMPLE 368

6-{3-[4-(4-Chlorophenyl)-1-piperazinyl]-1-propenyl}-3,4-dihydrocarobstyril

Colorless prism-like crystals (from ethanol-chloroform)
Melting point: 224.5°–225.5° C.

EXAMPLE 369

6-{3-[4-(2-Fluorophenyl)-1-piperazinyl]-1-propenyl}-3,4-dihydrocarbostyril

Colorless prism-like crystals (from ethanol-chloroform)
Melting point: 188.5°–190° C.

EXAMPLE 370

6-{3-[4-(2-Ethoxyphenyl)-1-piperazinyl]-1-propenyl}-3,4-dihydrocarbostyril

Colorless needle-like crystals (from methanol-chloroform)

EXAMPLE 371

6-{4-[4-(2-Ethoxyphenyl)-1-piperazinyl]-1-butenyl}-3,4-dihydrocarbostyril

Colorless needle-like crystals (from ethanol-chloroform)

EXAMPLE 372

6-{3-[4-(3-Methylphenyl)-1-piperazinyl]-1-propenyl}-3,4-dihydrocarbostyril

Colorless prism-like crystals (from ethanol)
Melting point: 167°–168° C.

EXAMPLE 373

6-{4-[4-(3-Methylphenyl)-1-piperazinyl]-1-butenyl}-3,4-dihydrocarbostyril

Colorless prism-like crystals (from ethanol)
Melting point: 171.5°–172.5° C.

EXAMPLE 374

6-{4-[4-(4-Methylphenyl)-1-piperazinyl]-1-butenyl}-3,4-dihydrocarbostyril

Colorless prism-like crystals (from ethanol-chloroform)
Melting point: 202°–203° C.

EXAMPLE 375

6-{3-[4-(2-Methoxyphenyl)-1-piperazinyl]-1-propenyl}-3,4-dihydrocarbostyril

Colorless needle-like crystals (from ethanol-acetone-chloroform
Melting point: 174°–175° C.

EXAMPLE 376

6-{4-[4-(2,3-Dimethylphenyl)-1-piperazinyl]-1-butenyl}-3,4-dihydrocarbostyril

Colorless prism-like crystals (from ethanol-acetone-chloroform)
Melting point: 175°–176° C.

EXAMPLE 377

6-{4-[4-(2-Chloro-6-methylphenyl)-1-piperazinyl]-1-butenyl}-3,4-dihydrocarbostyril Colorless prism-like crystals (from ethanol-acetone-chloroform)
Melting point: 179°–180° C.

EXAMPLE 378

6-{3-[4-(4-Ethoxycarbonylphenyl)-1-piperazinyl]-1-propenyl}-3,4-dihydrocarbostyril Colorless needle-like crystals (from ethanol-chloroform)
Melting point: 190°–192° C.

EXAMPLE 379

6-{4-[4-(4-Methylthiophenyl)-1-piperazinyl]-1-butenyl}-3,4-dihydrocarbostyril

Colorless needle-like crystals (from ethanol-chloroform)
Melting point: 175.5°–177° C.

EXAMPLE 380

6-{4-[4-(4-Acetylphenyl)-1-piperazinyl]-1-butenyl}-3,4-dihydrocarbostyril

Colorless prism-like crystals (from ethanol-chloroform)
Melting point: 213°–215° C.

EXAMPLE 381

6-{3-[4-(4-Cyanophenyl)-1-piperazinyl]-1-propenyl}-3,4-dihydrocarbostyril

Colorless prism-like crystals (from ethanol-chloroform)
Melting point: 196°–198° C.

EXAMPLE 382

6-{3-[4-(2-Hydroxyphenyl)-1-piperazinyl]-1-propenyl}-3,4-dihydrocarbostyril

Colorless prism-like crystals (from ethanol-chloroform)
Melting point: 192°–194° C.

EXAMPLE 383

1-Methyl-6-{3-[4-(3-methylphenyl)-1-piperazinyl]-1-prpenyl}-3,4-dihydrocarbostyril monooxalate Yellow needle-like crystals (from ethanol)
Melting point: 178°–179° C.

EXAMPLE 384

1-Benzyl-6-{3-[4-(3-methylphenyl)-1-piperazinyl]-1-propenyl}-3,4-dihydrocarbostyril monooxalate Colorless needle-like crystals (from ethanol)
Melting point: 176°–179° C.

EXAMPLE 385

1-Allyl-6-{3-[4-(3-methylphenyl)-1-piperazinyl]-1-propenyl}-3,4-dihydrocarbostyril monooxalate Coloress needle-like crystals (from ethanol)
Melting point: 167°–168° C.

EXAMPLE 386

1-(2-Propynyl)-6-{3-[4-(3-methylphenyl)-1-piperazinyl]-1-propenyl}-3,4-dihydrocarbostyril monooxalate Colorless powdery crystals (from ethanol)
Melting point: 158°–160° C.

EXAMPLE 387

6-{3-[4-(3-Carboxyphenyl)-1-piperazinyl]-1-propenyl}-3,4-dihydrocarbostyril monohydrochloride Colorless needle-like crystals (from ethanol-water)
Melting point: 264°–266° C.

EXAMPLE 388

6-{4-[4-(3,4-Methylenedioxyphenyl)-1-piperazinyl]-1-butenyl}-3,4-dihydrocarbostyril monohydrochloride Colorless needle-like crystals (from methanol)
Melting point: 226°–228° C.

EXAMPLE 389

6-[3-Methyl-3-(4-phenyl-1-piperazinyl)-1-propenyl]-3,4-dihydrocarbostyril

Colorless prism-like crystals (from ethanol-chloroform)
Melting point: 172°–173° C.

EXAMPLE 390

1.8 Grams of 6-{3-[4-(3-methylphenyl)-1-piperazinyl]-2-propenyl}-3,4-dihydrocarbostyril and 0.25 g of sodium hydride (50% in mineral oil) were mixed into 60 ml of dimethylformamide and the mixture was stirred at a room temperature for 2 hours then 0.7 g of benzyl chloride was added to the reaction mixture and stirred at a room temperature for 8 hours. The reaction mixture was poured into 150 ml of saturated sodium chloride aqueous solution and was extracted with chloroform, the chloroform layer was washed with water, dried and chloroform was removed by distillation. The residue thus obtained was purified by a silica-gel column chromatography and an oily substance thus obtained was dissolved in 20 ml of acetone, then under stirring condition, the pH of the solution was adjusted to pH 3 to 4 by adding 5%-oxalic acid acetone solution to obtain precipitates. The precipitates were collected by filtration and washed with acetone then recrystallized from ethanol to obtain 2.2 g of 1-benzyl-6-{3-[4-(3-methylphenyl)-1-piperazinyl]-2-propenyl}-3,4-dihydrocarbostyril monooxalate in colorless needle-like crystals, having the metling point of 176°–178° C.

By a method similar to that described in Example 390, there were obtained compounds of Examples 391–393 as follows:

EXAMPLE 391

1-Methyl-6-{3-[4-(3-methylphenyl)-1-piperazinyl]-2-propenyl}-3,4-dihydrocarbostyril monooxalate Light pink needle-like crystals (from ethanol)
Melting point: 178°–179° C.

EXAMPLE 392

1-Allyl-6-{3-[4-(3-methylphenyl)-1-piperazinyl]-2-propenyl}-3,4-dihydrocarbostyril monooxalate Colorless needle-like crystals (from ethanol)
Melting point: 167°–168° C.

EXAMPLE 393

1-(2-Propynyl)-6-{3-[4-(3-methylphenyl)-1-piperazinyl]-2-propenyl}-3,4-dihydrocarbostyril monooxalate Colorless powdery crystals (from ethanol)
Melting point: 158°–160° C.

EXAMPLE 394

0.94 Gram of 6-{3-[4-(2-ethoxyphenyl)-1-piperazinyl]-propyl}-3,4-dihydrocarbostyril and 0.12 g of sodium hydride (50% in mineral oil) were suspended in 40 ml of dimethylformamide and stirred at a room temperature for 2 hours. Then 0.37 g of isoamyl bromide was added to the reaction mixture and stirred at a room temperature for 12 hours. The reaction mixture was poured into saturated sodium chloride aqueous solution and was extracted with chloroform. The chloroform extract was dried under a reduced pressure and the residue thus obtained was separated and purified by a silica-gel chromatography. The purified product was converted into oxalate and recrystallized from acetone-water to obtain 1-isopentyl-6-{3-[4-(2-ethoxyphenyl)-1-piperazinyl]propyl}-3,4-dihydrocarbostyril monooxalate in colorless plate-like crystals. Yield: 0.51 g.
Melting point: 150°–151° C.

By a method similar to that described in Example 394, there were obtained compound of Example 395 as follows:

EXAMPLE 395

1-(3-Phenylpropyl)-6-{3-[4-(2-ethoxyphenyl)-1-piperazinyl]propyl}-3,4-dihydrocarbostyril monooxalate Colorless plate-like crystals (from acetone-water)
Melting point: 117°–118° C.

EXAMPLE 396

2.45 Grams of 6-(4-chloro-1-butenyl)-3,4-dihydrocarbostyril and 1.6 g of sodium iodide were dispersed in 60 ml of acetone and refluxed by heating for 2 hours. Then 80 ml of dimethylformamide was added to the reaction mixture and acetone was removed under a reduced pressure. To this reaction mixture were added 2.2 g of 4-(2-ethoxyphenyl)-1-piperazine and 2 ml of triethylamine and stirred at 70°–80° C. for 6 hours. The reaction mixture was concentrated under a reduced pressure and to the residue thus obtained was added 80 ml of 5%-sodium hydrogencarbonate aqueous solution and stirred then the organic layer was extracted with chloroform and the chloroform layer was washed with water, dried and chloroform was removed by distillation. The residue thus obtained was recrystallized from methanol to obtain 3.1 g of 6-{4-[4-(2-ethoxyphenyl)-1-piperazinyl]-1-butenyl}-carbostyril in colorless needle-like crystals.
Melting point: 225°–228° C.

By a method similar to that described in Example 396 there was obtained compound of Example 397 as follows:

EXAMPLE 397

6-[4-(4-Phenyl-1-piperazinyl)-1-butenyl]-carbostyril monohydrochloride

Colorless needle-like crystals (from methanol)
Melting point: 233°–235° C.

EXAMPLE 398

1.5 Grams of 6-[4-(4-phenyl-1-piperazinyl)-1-butenyl]-carbostyril and 0.3 g of 10%-palladium were dispersed in 120 ml of ethanol and catalytically reduced for 6 hours. The reaction mixture was filtered and the mother liquor was concentrated under a reduced pressure and the residue thus obtained was recrystallized from ethanol and 0.8 g of 6-[4-(4-phenyl-1-piperazinyl)-butyl]carbostyril was obtained in colorless needle-like crystals. Melting point: 159°–162° C.

EXAMPLE 399

2.0 Grams of 6-{4-[4-(2-ethoxyphenyl)-1-piperazinyl]-1-butenyl}-3,4-dihydrocarbostyril and 3.5 g of DDQ were mixed in 20 ml of benzene and the mixture was refluxed by heating for 5 hours. The reaction mixture was then concentrated under a reduced pressure and the residue thus obtained was extracted with chloroform. The chloroform layer was washed with 5%-NaHCO$_3$ aqueous solution three times then washed with water twice and dried. Chloroform was removed by distillation and the residue obtained was purified by a silica-gel column chromatography and recrystallized from methanol to obtain 0.12 g of 6-{4-[4-(2-ethoxyphenyl)-1-piperazinyl]-1-butenyl}carbostyril in colorless needle-like crystals. Melting point: 225°–228° C.

EXAMPLE 400

2.4 Grams of 6-(1-oxo-3-chloropropyl)-3,4-dihydrocarbostyril and 1.6 g of sodium iodide were mixed in 60 ml of isopropanol and stirred at 40°–50° C. for 2 hours. Then 2.2 g of 4-benzylpiperidine and 3.0 g of DBU were added to the reaction mixture and refluxed by heating for 6 hours. The reaction mixture was poured into 100 ml of 5%-sodium hydrogen-carbonate aqueous solution and stirred at a room temperature for 1 hour. The insoluble matters fromed were collected by filtration washed with water and dried, then recrystallized from ethanol to obtain 1.8 g of 6-[1-oxo-3-(4-benzyl-1-piperidyl)propyl]-3,4-dihydrocarbostyril in light yellow plate-like crystals.
Melting point: 170°–171° C.

EXAMPLE 401

2.4 Grams of 6-(1-oxo-3-chloropropyl-3,4-dihydrocarbostyril and 3.6 g of 4-phenyl-4-hydroxypiperidine were mixed in 80 ml of xylene and refluxed by heating for 24 hours. The reaction mixture was concentrated under a reduced pressure to dryness and the residue thus obtained was dissolved in 100 ml of chloroform. The chloroform layer was washed with 5%-sodium hydrogencarbonate aqueous solution twice and with water twice then dried with anhydrous sodium sulfate and chloroform was removed by distillation. To the residue thus obtained was added ether-hexane and insoluble matter was collected by filtration then recrystallized from ethanol-chloroform to obtain 1.7 g of 6-[1-oxo-4-(4-phenyl-4-hydroxy-1-piperidyl)-butyl]-3,4-dihydrocarbostyril in colorless flake-like crystals. Melting point: 196°–197° C.

EXAMPLE 402

2.6 Grams of 6-(1-oxo-4-chlorobutyl)-3,4-dihyro-carbostyril, 1.2 g of pyridine and 2.7 g of 4-phenyl-4-acetylpiperidine were mixed in 30 ml of dimethylformamide and stirred at 70°–80° C. for 7 hours. The reaction mixture was poured into 100 ml of 5%-sodium hydrogencarbonate aqueous solution and the organic layer was extracted with chloroform then the chloroform layer was washed with water, dried and chloroform was removed by distillation. The residue thus obtained was recrystallized from ethanol to obtain 6-[1-oxo-4-(4-phenyl-4-acetyl-1-piperidyl)-butyl]-3,4-dihydrocarbostyril in light yellow plate-like crystals. Yield: 2.1 g. Melting point: 166°–167° C.

EXAMPLE 403

5.0 Grams of 6-(1-oxo-4-chloropropyl)-3,4-dihydrocarbostyril and 7.5 g of sodium iodide were dispersed in 120 ml of anhydrous dimethylformamide and the mixture was stirred at 50°–60° C. for 2 hours. Then 8.1 g of 4-phenyl-1,2,5,6-tetrahydropyridine and 5 ml of triethylamine were added to the reaction mixture and stirred at 50°–60° C. for 6 hours. The reaction mixture was then stirred at a room temperature for 24 hours. The reaction mixture was concentrated under a reduced pressure to obtain a residue. Then 80 ml of 5%-sodium hydrogencarbonate aqueous solution was added to the residue and was extracted with chloroform and chloroform was washed with water and dried then chloroform was removed by distillation. Recrystallization from ethanol to obtain 6.0 g of 6-[1-oxo-3-(4-phenyl-1,2,5,6-tetrahydro-1-pyridyl)]-3,4-dihydrocarbostyril in light yellow plate-like crystals. Melting point: 167°–168° C.

EXAMPLE 404

5.0 Grams of 6-(1-oxo-4-chlorobutyl)-3,4-dihydrocarbostyril and 3.5 g of sodium iodide were mixed in 100 ml of acetone and the mixture was stirred at 40°–50° C. for 5 hours. Then to this reaction mixture was added to 80 ml of dimethylformamide and acetone was removed by distillation under a reduced pressure. Then to the reaction mixture was added 5.0 g of 4-phenylpiperidine and 5 g of triethylamine and the mixture was stirred at 70°–80° C. for 6 hours. The reaction mixture was concentrated under a reduced pressure and 50 ml of 5%-sodium hydrogencarbonate aqueous solution was added to the residue to obtain crude crystals. The crude crystals were collected by filtration, washed with water and dried, then dispersed in 80 ml of chloroform and stirred at a room temperature for 1.0 hours. The insoluble matters in the chloroform solution were removed and chloroform was removed by distillation. The residue thus obtained was recrystallized from ethanol to obtain 5.6 g of 6-[1-oxo-4-(4-phenyl-1-piperidyl)butyl]-3,4-dihydrocarbostyril in light yellow plate-like crystals. Melting point: 167°–168° C.

By a method similar to that described in Example 404 by using a suitable starting material, there were obtained compounds of Examples 405–427 as follows:

EXAMPLE 405

6-[1-Oxo-3-(4-phenyl-1-piperidyl)propyl]-3,4-dihydrocarbostyril

Colorless needle-like crystals (from ethanol)
Melting point: 183°–184° C.

EXAMPLE 406

6-[1-Oxo-4-(4-benzyl-1-piperidyl)butyl]-3,4-dihydrocarbostyril

Light yellow plate-like crystals (from ethanol)
Melting point: 120°–121° C.

EXAMPLE 407

6-[1-Oxo-3-(4-benzyl-1-piperidyl)propyl]-3,4-dihydrocarbostyril

Light yellow plate-like crystals (from ethanol)
Melting point: 170°–171° C.

EXAMPLE 408

6-[1-Oxo-4-(4-phenyl-4-hydroxy-1-piperidyl)butyl]-3,4-dihydrocarbostyril

Colorless flake-like crystals (from ethanol-chloroform)
Melting point: 196°–197° C.

EXAMPLE 409

6-[1-Oxo-3-(4-phenyl-4-hydroxy-1-piperidyl)propyl]-3,4-dihydrocarbostyril

Colorless needle-like crystals (from ethanol-ethyl acetate)
Melting point: 205°–206° C.

EXAMPLE 410

6-{1-Oxo-4-[4-(4-chlorophenyl)-4-hydroxy-1-piperidyl]butyl}-3,4-dihydrocarbostyril Light yellow flake-like crystals (from ethanol-chloroform)
Melting point: 210°–211° C.

EXAMPLE 411

6-[1-Oxo-4-(4-phenyl-4-acetyl-1-piperidyl)butyl]3,4-dihydrocarbostyril

Light yellow plate-like crystals (from ethanol)
Melting point: 166°–167° C.

EXAMPLE 412

6-{1-Oxo-4-[4-(2-benzimidazolinon-1-yl)-1-piperidyl]butyl}-3,4-dihydrocarbostyril Colorless powdery crystals (from methanol)
Melting point: 247°–248° C.

EXAMPLE 413

6-{1-Oxo-3-[4-(2-benzimidazolinon-1-yl)-1-piperidyl]propyl}-3,4-dihydrocarbostyril monohydrochloride Colorless plate-like crystals (from methanol-chloroform)
Melting point: 242°–243° C. (decomposed)

EXAMPLE 414

6-[1-Oxo-4-(4-phenyl-1,2,5,6-tetrahydro-1-pyridyl)butyl]-3,4-dihydrocarbostyril monohydrochloride Light yellow plate-like crystals (from ethanol)
Melting point: 170°–171° C.

EXAMPLE 415

6-[1-Oxo-3-(4-phenyl-1,2,5,6-tetrahydro-1-pyridyl)propyl]-3,4-dihydrocarbostyril Light yellow plate-like crysals (from ethanol)
Melting point: 167°–168° C.

EXAMPLE 416

6-{1-Oxo-4-[4-(4-chlorophenyl)-1,2,5,6-tetrahydro-1-pyridyl]butyl}-3,4-dihydrocarbostyril monohydrochloride Colorless plate-like crystals (from ethanol)

Melting point: 188°–189° C.

EXAMPLE 417

1-Isopentyl-6-[1-oxo-3-(4-phenyl-1-piperidyl)-propyl]-3,4-dihydrocarbostyril monohydrochloride Colorless mica-like crystals (from ethanol-water)
Melting point: 205°–206° C. (decomposed)

EXAMPLE 418

1-Allyl-6-[1-oxo-3-(4-phenyl-piperidyl)propyl]-3,4-dihydrocarbostyril monohydrochloride Colorless plate-like crystals (from ethanol-water)
Melting point: 198°–199° C. (decomposed)

EXAMPLE 419

1-(2-Propynyl)-6-[1-oxo-3-(4-phenyl-1-piperidyl)-propyl]-3,4-dihydrocarbostyril monohydrochloride Colorless plate-like crystals (from ethanol-water)
Melting point: 203°–204° C. (decomposed)

EXAMPLE 420

1-(3-Phenylpropyl)-6-[1-oxo-3-(4-phenyl-1-piperidyl)-propyl]-3,4-dihydrocarbostyril monohydrochloride Colorless powdery crystals (from isopropanol)
Melting point: 164°–165° C.

EXAMPLE 421

1-Methyl-6-[1-oxo-3-(4-phenyl-1-piperidyl)propyl]-3,4-dihydrocarbostyril monohydrochloride Light yellow plate-like crystals (from ethanol-water)
Melting point: 213°–214° C. (decomposed)

EXAMPLE 422

6-{1-Oxo-3-[4-(4-chlorophenyl)-1,2,5,6-tetrahydro-1-pyridyl]propyl}-3,4-dihydrocarbostyril ¼-hydrate Light yellow flake-like crystals (from ethanol)
Melting point: 170°–171° C.

EXAMPLE 423

6-{1-Oxo-4-[4-(4-chlorophenyl-4-hydroxy-1-piperidyl]-butyl}-3,4-dihydrocarbostyril Light yellow flake-like crystals (from ethanol-chloroform)
Melting point: 210°–211° C.

EXAMPLE 424

6-{1-Oxo-4-[4-(3,5-dimethylphenyl)-1-piperidyl]-butyl}-3,4-dihydrocarbostyril

Light yellow powdery crystals (from ethanol)
Melting point: 171°–172° C.

6-{1-Oxo-3-[4-(4-methylphenyl)-1,2,5,6-tetrahydro-1-pyridyl]propyl}-3,4-dihydrocarobostyril Light yellow mica-like crystals (methanol-water)
Melting point: 189°–190° C.

6-{1-Oxo-3-[4-(4-fluorophenyl)-1,2,5,6-tetrahydro-1-pyridyl]propyl}-3,4-dihydrocarbostyril Light yellow plate-like crystals (from ethanol-water)
Melting point: 181°–182° C.

6-{1-Oxo-3-[4-(3-methylphenyl)-1,2,5,6-tetrahydro-1-pyridyl]propyl}-3,4-dihydrocarbostyril Light yellow plate-like crystals (from ethanol-water)
Melting point: 152°–153° C.

6-{1-Oxo-3-[4-(3,5-dimethoxyphenyl)-1,2,5,6-tetrahydro-1-pyridyl]propyl}-3,4-dihydrocarbostyril 6-{1-Oxo-3-[4-(3-methoxyphenyl)-1,2,5,6-tetrahydro-1-pyridyl]propyl}-3,4-dihydrocarbostyril Light yellow needle-like crystals (from ethanol-water)
Melting point: 155°–156° C.

7-[1-Oxo-3-(4-phenyl-1-piperidyl)propyl]-3,4-dihydrocarbostyril

Colorless needle-like crystals (from methanol)
Melting point: 171°–173° C.

7-{1-Oxo-3-[4-(4-methylphenyl)-1-piperidyl]propyl}-3,4-dihydrocarbostyril monohydrochloride White crystals (from ethanol-water)
Melting point: 212°–216° C. (decomposed).

7-{-Oxo-3-[4-(4-fluorophenyl)-1-piperidyl]propyl}-3,4-dihydrocarbostyril

7-{1-Oxo-3-[4-(2,4-dimethylphenyl)-1-piperidyl]-propyl}-3,4-dihydrocarostyril monohydrochloride White crystals (from methanol-water)
Melting point: 226°–229° C.

EXAMPLE 425

6-[1-Oxo-2-(4-phenyl-1-piperidyl)butyl]carbostyril monohydrochloride

Colorless plate-like crystals (from methanol)
Melting point: 189°–190° C.

EXAMPLE 426

6-[1-Oxo-2-(4-benzyl-1-piperidyl)butyl]carbostyril monohydrochloride

Colorless powdery crystals (from ethanol-water)
Melting point: 178°–179° C.

EXAMPLE 427

6-[1-Oxo-2-(4-phenyl-1,2,5,6-tetrahydro-1-pyridyl)-butyl]-carbostyril monohydrochloride Light yellow plate-like crystals (from ethanol-water)
Melting point: 190°–191° C.

EXAMPLE 428

1.8 Grams of 6-[1-oxo-3-(4-phenyl-1-piperidyl)-propyl]-3,4-dihydrocarbostyril and 0.24 g of sodium hydride (50% in mineral oil) were mixed in 50 ml of dimethylformamide and the mixture was stirred at a room temperature for 3 hours. Then 0.8 g of methyl iodide was added thereto and stirred at a room temperature for 3 hours. The reaction mixture was poured into 150 ml of saturated sodium chloride aqueous solution and the organic layer was extracted with chloroform. The chloroform layer was washed with water, dried and chloroform was removed by distillation. The residue thus obtained was isolated and purified by preparative thin-layer chromatography and the desired product was converted into the hydrochloride then recrystallized from ethanol-water to obtain 1.5 g of 1-methyl-6-[1-oxo-3-(4-phenyl-1-piperidyl)-propyl]-3,4-dihydrocarbostyril monohydrochloride in light yellow plate-like crystals.

Melting point: 213°–214° C. (decomposed)

By a method similar to that described in Example 428, by using a suitable starting material, there were obtained compounds of Examples 429–432 as follows:

EXAMPLE 429

1-Isopentyl-6-[1-oxo-3-(4-phenyl-1-piperidyl)-propyl]-3,4-dihydrocarbostyril monohydrochloride Colorless mica-like crystals (from ethanol-water)
Melting point: 205°–206° C. (decomposed)

EXAMPLE 430

1-Allyl-6-[1-oxo-3-(4-phenyl-1-piperidyl)propyl]-3,4-dihydrocarbostyril monohydrochloride Colorless plate-like crystals (from ethanol-water)
Melting point: 198°–199° C. (decomposed)

EXAMPLE 431

1-(2-Propynyl)-6-[1-oxo-3-(4-phenyl-1-piperidyl)-propyl]-3,4-dihydrocarbostyril monohydrochloride Colorless plate-like crystals (from ethanol-water)
Melting point: 203°–204° C. (decomposed)

EXAMPLE 432

1-(3-Phenylpropyl)-6-[1-oxo-3-(4-phenyl-1-piperidyl)-propyl]-3,4-dihydrocarbostyril monohydrochloride Colorless powdery crystals (from isopropanol)
Melting point: 164°–165° C.

EXAMPLE 433

2.6 Grams of 6-(1-hydroxy-3-chloropropyl)-3,4-dihydrocarbostyril and 1.8 g of sodium iodide were mixed in 60 ml of dimethylformamide and the mixture was stirred at a room temperature for 7 hours. Then 2.0 g of triethylamine and 2.5 g of 4-phenylpiperidine were added to the mixture and stirred at a room temperature for 24 hours. The reaction mixture was poured into 200 ml of 1%-sodium hydrogencarbonate aqueous solution and was extracted with chloroform. The chloroform layer was washed with water and dried, chloroform was removed by distillation. The residue thus obtained was recrystallized from ethanol to obtain 2.5 g of 6-[1-hydroxy-3-(4-phenyl-1-piperidyl)propyl]-3,4-dihydrocarbostyril in colorless plate-like crystals. Melting point: 155.5°–156.5° C.

By a method similar to that described in Example 433, by using a suitable starting material, there were obtained compounds of Examples 434–437 as follows:

EXAMPLE 434

6-[1-Hydroxy-3-(4-benzyl-1-piperidyl)propyl]-3,4-dihydrocarbostyril

Colorless plate-like crystals (from methanol)
Melting point: 168°–169° C.

EXAMPLE 435

6-[1-Hydroxy-3-(4-phenyl-4-hydroxy-1-piperidyl)-propyl]-3,4-dihydrocarbostyril

Colorless needle-like crystals (from ethanol)
Melting point: 102°–103° C.

EXAMPLE 436

6-[1-Hydroxy-3-(4-phenyl-1,2,5,6-tetrahydro-1-pyridyl)propyl]-3,4-dihydrocarbostyril Colorless plate-like crystals (from ethanol)
Melting point: 144°–145° C.

EXAMPLE 437

6-{1-Hydroxy-3-[4-(4-chlorophenyl)-1,2,5,6-tetrahydro-1-pyridyl]-propyl}-3,4-dihydrocarbostyril Colorless plate-like crystals (from ethanol)
Melting point: 169°–170° C.

6-{1-Hydroxy-3-[4-(4-chlorophenyl)-1,2,5,6-tetrahydro-1-pyridyl]propyl}-3,4-dihydrocarbostyril Colorless plate-like crystals (from ethanol)
Melting point: 169°–170° C.

6-{1-Hydroxy-3-[4-(3-methylphenyl)-1,2,5,6-tetrahydro-1-pyridyl]propyl}-3,4-dihydrocarbostyril Colorless plate-like crystals (from ethanol)
Melting point: 142°–143° C.

6-{1-Hydroxy-3-[4-(4-methylphenyl)-1,2,5,6-tetrahydro-1-pyridyl]propyl}-3,4-dihydrocarbostyril Colorless mica-like crystals (from ethanol)
Melting point: 159°–160° C.

7-[1-Hydroxy-3-(4-phenyl-1-piperidyl)propyl]-3,4-dihydrocarbostyril

Colorless prism-like crystals (from ethanol)
Melting point: 146°–149° C.

EXAMPLE 438

1.9 Grams of 6-[1-oxo-3-(4-phenyl-1-piperidyl)-propyl]-3,4-dihydrocarbostyril and 0.5 g of palladium black were dispersed in 80 ml of water and the dispersion was stirred under 2 atmospheric pressure of hydrogen gas at a room temperature for 5 hours. The reaction mixture was filtered for removing the palladium black and the mother liquor was concentrated under a reduce pressure then the residue thus obtained was crystallized by adding a small amount of ethanol then crude crystals thus obtained were collected by filtration and recrystallized from ethanol to obtain 1.4 g of 6-[1-hydroxy-3-(4-phenyl-1-piperidyl)-propyl]-3,4-dihydrocarbostyril in colorless plate-like crystals. Melting point: 155.5°–156° C.

By a method similar to that described in Example 438, by using a suitable starting material, there were obtained compounds of Examples 439–441 as follows:

EXAMPLE 439

6-[1-Hydroxy-3-(4-phenyl-4-hydroxy-1-piperidyl)-propyl]-3,4-dihydrocrbostyril

Colorless needle-like crystals (from ethanol)
Melting point: 102°–103° C.

EXAMPLE 440

6-[1-Hydroxy-3-(4-phenyl-1,2,5,6-tetrahydro-1-pyridyl)propyl]-3,4-dihydrocarbostryril Colorless plate-like crystals (from ethanol)
Melting point: 144°–145° C.

EXAMPLE 441

6-{1-Hydroxy-3-[4-(4-chlorophenyl)-1,2,5,6-tetrahydro-1-pyridyl]propyl}-3,4-dihydrocarbostyril Colorless plate-like crystal (from ethanol)
Melting point: 169°–170° C.

EXAMPLE 442

2.2 Grams of 6-[1-oxo-3-(4-phenyl-1-piperidyl)-propyl]-3,4-dihydrocarbostyril and 0.5 g of 5%-palladium carbon were dispersed in 80 ml of ethanol and stirred under 2 atmospheric pressure of hydrogen gas at a room temperature for 5 hours. The reaction mixture was filtered to remove the palladium black and the mother liquor was concentrated under a reduced pressure. The residue thus obtained was recrystallized from ethanol to obtain 1.5 g of 6-[1-hydroxy-3-(4-phenyl-1-piperidyl)propyl]-3,4-dihydrocarbostyril in colorless plate-like crystals. Melting point: 155.5°–156° C.

By a method similar to that described in Example 442 there was obtained compounds of Examples 443–445 as follows:

EXAMPLES 443

6-[1-Hydroxy-3-(4-phenyl-4-hydroxy-1-piperidyl)-propyl]3,4-dihydrocrbostyril

Colorless needle-like crystals (from ethanol)
Melting point: 102°–103° C.

EXAMPLE 444

6-[1-Hydroxy-3-(4-phenyl-1,2,5,6-tetrahydro-1-pyridyl)propyl]-3,4-dihydrocarbostyril Colorless plate-like crystals (from ethanol)
Melting point: 144°–145° C.

EXAMPLE 445

6-{1-Hydroxy-3-[4-(4-chlorophenyl)-1,2,5,6-tetrahydro-1-pyridyl]propyl}-3,4-dihydrocarbostyril Colorless plate-like crystals (from ethanol)
Melting point: 169°–170° C.

EXAMPLE 446

1.9 Grams of 6-[1-oxo-3-(4-phenyl-1,2,5,6-tetrahydro-1-pyridyl]-3,4-dihydrocarbostrryil and 1.0 g of lithium aluminium hydride were dispersed in 80 ml of anhydrous tetrahydrofuran and stirred at a room temperature for hours. Then saturated sodium chloride aqueous solution was added gradually to the reaction mixture. Then the tetrahydrofuran solution was obtained by decantation. The tetrahydrofuran was removed by distillation and the residue thus obtained was recrystallized from ethanol to obtain 0.8 g of 6-[1-hydroxy-3-(4-phenyl-1,2,5,6-tetrahydro-1-pyridyl)propyl]-3,4-dihydrocarbostyril in colorless plate-like crystals.
Melting point: 144°–145° C.

By a method similar to that described in Example 446, there were obtained compounds of Examples 447–450 as follows:

EXAMPLE 447

6-[1-Hydroxy-3-(4-phenyl-1-piperidyl)propyl]-3,4-dihydrocarbostyril

Colorless plate-lie crystals (from ethanol)
Melting point: 155.5°–156.5° C.

EXAMPLE 448

6-[1-Hydroxy-3-(4-benzyl-1-piperidyl)propyl]-3,4-dihydrocarbostyril

Colorless plate-like crystals (from methanol)
Melting point: 168°–169° C.

EXAMPLE 449

6-[1-Hydroxy-3-(4-phenyl-4-hydroxyl-1-piperidyl)-propyl]-3,4-dihydrocarbostyril

Colorless needle-like crystals (from ethanol)
Melting point: 102°–103° C.

EXAMPLE 450

6-{1-Hydroxy-3-[4-(4-chlorophenyl)-1,2,5,6-tetrahydro-1-pyridyl]propyl}-3,4-dihydrocarbostyril Colorless plate-like crystals (from ethanol)
Melting point: 169°–170° C.

EXAMPLE 451

To 2.9 g of 6-{1-oxo-3-[4-chlorophenyl)-1,2,5,6-tetrahydro-1-pyridyl]propyl}-3,4-dihydrocarbostyril was added 100 ml of methanol and 1.2 g of sodium borohydride was added gradually to the mixture under stirring condition, further stirred at room temperature for 5 hours. Then 5 ml of concentrated hydrochloric acid was added to the reaction mixture and concentrated under a reduced pressure to dryness. To the residue thus obtained was added 50 ml of 2%-sodium hydroxide aqueous solution and was extracted with dichloromethane. The dichloromethane layer was washed with water and dried then dichloromethane was removed by distillation. The residue thus obtained was purified by a silica-gel column chromatography and recrystallized from ethanol to obtain 6-{1-hydroxy-3-[4-(4-chlorophenyl)-1,2,5,6-tetrahydro-1-pyridyl]-propyl}-3,4-dihydrostyril in colorless plate-like crystas. Melting point: 169°–170° C.

By a method similar to that described in Example 451, there was obtained compounds of Examples 452–455 as follows:

EXAMPLE 452

6-[1-Hydroxy-3-(4-phenyl-1-piperidyl)propyl]-3,4-dihydrocarbostyril

Colorless plate-like crystals (from ethanol)
Melting point: 155.5°–156° C.

EXAMPLE 453

6-[1-Hydroxy-3-(4-benzyl-1-piperidyl)propyl]-3,4-dihydrocarbostyril

Colorless plate-like crystals (from methanol)
Melting point: 168°–169° C.

EXAMPLE 454

6-[1-Hydroxy-3-(4-phenyl-4-hydroxy-1-piperidyl)-propyl]-3,4-dihydrocarbostyril

Colorless needle-like crystals (from ethanol)
Melting point: 102°–103° C.

EXAMPLE 455

6-[1-Hydroxy-3-(4-phenyl-1,2,5,6-tetrahydro-1-pyridyl)propyl]-3,4-dihydrocarbostril Colorless plate-like crystals (from ethanol)
Melting point: 144°–145° C.

6-{1-Hydroxy-3-[4-(4-chlorophenyl)-1,2,5,6-tetrahydro-1-pyridyl]propyl}-3,4-dihydrocarbostyril Colorless plate-like crystals (from ethanol)
Melting point: 169°–170° C.

6-{1-Hydroxy-3-[4-(3-methylphenyl)-1,2,5,6-tetrahydro-1-pyridyl]propyl}-3,4-dihydrocarbostyril Colorless plate-like crystals (from ethanol)
Melting point: 142°-143° C.

6-{1-Hydroxy-3-[4-(4-methylphenyl)-1,2,5,6-tetrahydro-1-pyridyl]propyl}-3,4-dihydrocarbostyril Colorless mica-like crystals (from ethanol)
Melting point: 159°-160° C.

7-[1-Hydroxy-3-(4-phenyl-1-piperidyl)propyll]-3,4-dihydrocarbostryil

Colorless prism-like crystals (from ethanol)
Melting point: 146°-149° C.

EXAMPLE 456

2.5 Grams of 6-[1-hydroxy-3-chloropropyl]-3,4-dihydrocarobstyril and 3.0 g of 4-phenyl-1,2,5,6-tetrahydropyridine were mixed in 50 ml of toluene and the mixture was refluxed by heating for 5 hours, then toluene was removed by distillation. To the residue thus obtained was added 50 ml of 5%-sodium hydrogencarbonate aqueous solution and was extracted with chloroform. The chloroform layer was washed with water and dried, then chloroform was remove by distillation. The residue thus obtained was recrystallized from ethanol to obtain 2.1 g of 6-[3-(4-phenyl-1,2,5,6-tetrahydropyridyl)-1-propenyl]-3,4-dihydrocarbostryil in light yellow plate-like crystals. Melting point: 182°-183° C. (decomposed).

By a method similar to that described in Example 456, there were obtained compounds of Examples 457–463 as follows:

EXAMPLE 457

6-[3-(4-Phenyl-1-piperidyl)-1-propenyl]-3,4-dihydrocarbostyril

Colorless plate-like crystals (from methanol)
Melting point: 163°-164° C.

EXAMPLE 458

6-[3-(4-Benzyl-1-piperidyl)-1-propenyl]-3,4-dihydrocarbostyril

Colorless needle-like crystals (from ethanol)
Melting point: 160°-161° C.

EXAMPLE 459

6-[4-(4-Phenyl-4-acetyl-1-piperidyl)-1-butenyl]-3,4-dihydrocarbostyril

Colorless plate-like crystals (from ethanol)
Melting point: 169°-170° C.

EXAMPLE 460

6-{3-[4-(4-Methylphenyl)-1,2,5,6-tetrahydro-1-pyridyl]-1-propenyl}-3,4-dihydrocarbostyril Light yellow plate-like crystals (from ethanol)
Melting point: 214°-215° C.

EXAMPLE 461

6-[3-(4-Phenyl-1,2,5,6-tetrahydro-1-pyridyl)-1-propenyl]-3,4-dihydrocarbostyril

Light yellow plate-like crystals (from ethanol)
Melting point: 182°-183° C. (decomposed)

EXAMPLE 462

7-[3-(4-Phenyl-1-piperidyl)-1-propenyl]-3,4-dihydrocarbostyril

Colorless needle-like crystals (from methanol)
Melting point: 165°-168° C.

EXAMPLE 463

6-{3-[4-(2-Methoxyphenyl)-1,2,5,6-tetrahydropyridyl]-propenyl}-3,4-dihydrocarbostyril monooxalate Colorless flake-like crystals (from
Melting point: 201°-205° C.

EXAMPLE 464

1.0 Gram of 6-[1-hydroxy-3-(4-phenyl-1,2,5,6-tetrahydro-1-pyridyl)propyl]-3,4-dihydrocarbostyril was dissolved in 30 ml of methanol, then 2 ml of concentrated hydrochloric acid was added to the solution and the mixture was refluxed by heating for 2 hours. The reaction mixture was concentrated under a reduced pressure, then thus obtained residue was treated with 50 ml of 0.5% of sodium hydroxide and the mixture was extracted with chloroform. The chloroform layer was washed with water and dried, next chloroform was removed by distillation at a room temperature then the residue thus obtained was recrystallized from ethanol to obtain 0.6 g of 6-[3-(4-phenyl-1,2,5,6-tetrahydro-1-pyridyl)-1-propenyl]-3,4-dihydrocarbostyril in light yellow plate-like crystals. Melting point: 182°-183° C. (decomposed).

By a method similar to that described in Example 464, there were obtained compounds of Examples 465–470 as follows:

EXAMPLE 465

6-[3-(4-Phenyl-1-piperidyl)-1-propenyl]-3,4-dihydrocarbostyril

Colorless plate-like crystals (from methanol)
Melting point: 163°-164° C.

EXAMPLE 466

6-[3-(4-Benzyl-1-piperidyl)-1-propenyl]-3,4-dihydrocarbostyril

Colorless needle-like crystals (from ethanol)
Melting point: 160°-161° C.

EXAMPLE 467

6-[4-(4-Phenyl-4-acetyl-1-piperidyl)-1-butenyl]-3,4-dihydrocarbostyril

Colorless plate-like crystals (from ethanol)
Melting point: 169°-170° C.

EXAMPLE 468

6-{3-[4-(4-Methylphenyl)-1,2,5,6-tetrahydro-1-pyridyl]-1-propenyl}-3,4-dihydrocarbostyril Light yellow plate-like crystals (from ethanol)
Melting point: 214°-215° C.

EXAMPLE 469

6-[3-(4-Phenyl-1,2,5,6-tetrahydro-1-pyridyl)-1-propenyl]-3,4-dihydrocarbostyril monohydrochloride Light yellow plate-like crystals (from ethanol)
Melting point: 182°-183° C. (decomposed)

EXAMPLE 470

7-[3-(4-Phenyl-1-piperidyl)-1-propenyl]-3,4-dihydrocarbostyril

Colorless needle-like crystals (from methanol)
Melting point: 165°–168° C.

EXAMPLE 471

6-{3-[4-(2-Methoxyphenyl)-1,2,5,6-tetrahydropyridyl]-1-propenyl}-3,4-dihydrocarbostyril monooxalate Colorless flake-like crystals (from ethanol-water)
Melting point: 201°–205° C.

EXAMPLE 472

2.0 Grams of 6-[3-(4-phenyl-1,2,5,6-tetrahydro-1-pyridyl)-1-propenyl]-3,4-dihydrocarbostyril and 0.2 g of palladium black were dispersed in 50 ml of dioxane and the dispersion was stirred under 2 atmospheric pressure of hydrogen gas for 5 hours. The reaction mixture was filtered and to the mother liquor was added 3 ml of concentrated hydrochloric acid and concentrated under a reduced pressure to dryness. The residue thus obtained was recrystallized from a small amount of ethanol and acetone, and crude crystals formed were collected by filtration, and recrystallized from methanol to obtain 1.6 g of 6-[3-(4-phenyl-1-piperidyl)propyl]-3,4-dihydrocarbostyril monohydrochloride in colorless plate-like crystals. Melting point: 232°–233° C. (decomposed).

By a method similar to that described in Example 472, there were obtained compounds of Examples 473°–476 as follows:

EXAMPLE 473

6-[3-(4-Phenyl-1-piperidyl)propyl]-3,4-dihydrocarbostyril monohydrochloride

Colorless plate-like crystals (from methanol)
Melting point: 232°–233° C.

EXAMPLE 474

6-[3-(4-Benzyl-1-piperidyl)propyl]-3,4-dihydrocarbostyril

Colorless plate-like crystals (from ethanol)
Melting point: 99°–100° C.

EXAMPLE 475

6-{3-[4-(4-Methylphenyl)-1-piperidyl]propyl}-3,4-dihydrocarbostyril

Colorless plate-like crystals (from isopropanol-n-hexane)
Melting point: 125°–126° C.

EXAMPLE 476

7-[3-(4-Phenyl-1-piperidyl)propyl]-3,4-dihydrocarbostyril

Colorless needle-like crystals (from ethanol-water)
Melting point: 114°–118° C.

EXAMPLE 477

5-[3-(4-Phenyl-1-piperidyl)propyl]-3,4-dihydrocarbostyril

EXAMPLE 478

6-{3-[4-(2-Methoxyphenyl)-1-piperidyl]propyl}-3,4-dihydrocarbostyril monooxalate Colorless flake-like crystals (from ethanol-water)
Melting point: 178°–181° C.

EXAMPLE 479

45.8 Grams of 8-methanesulfoxy-5-[1-oxo-3-(4-phenyl-1-piperazinyl)propyl]-3,4-dihydrocarbostyril and 5.9 g of potassium hydroxide were dissolved in ethanol. To this solution was added 1.0 g of 5%-palladium carbon and the mixture we catalytically hydrogenated under a normal atmospheric pressure and at a normal temperature for 8 hours. The catalyst was removed by filtration and the mother liquor was concentrated under a reduced pressure to dryness. The residue thus obtained was washed with water and recrystallized from ethanol-chloroform to obtain 5-[1-oxo-3-(4-phenyl-1-piperazinyl)propyl]-3,4-dihydrocarbostyril. Yield: 26.4 g.

| Elemental analysis for $C_{22}H_{25}O_2N_3$ | | | |
|---|---|---|---|
| | C | H | N |
| Calculated (%): | 72.70 | 6.93 | 11.56 |
| Found (%): | 72.62 | 6.95 | 11.56 |

EXAMPLE 480

2.0 Grams of 6-methylsulfonyloxy-7-[1-oxo-3-(4-phenyl-1-piperidyl)propyl]-3,4-dihydrocarbostyril and 0.5 g of palladium black were dispersed in 50 ml of ethanol and the mixture was catalytically reduced under 3 atmospheric pressure of hydrogen gas for 5 hours. The reaction mixture was filtered and the mother liquor was concentrated under a reduced pressure to obtain a residue. Then the residue was recrystallized from ethanol to obtain 1.1 g of 7-1-oxo-3-(4-phenyl-1-piperidyl)propyl-3,4-dihydrocarbostyril in colorless needle-like crystals. Melting point: 171°–173° C.

| Elemental analysis for $C_{23}H_{26}O_2N_2$ (M.W. 362.45) | | | |
|---|---|---|---|
| | C | H | N |
| Calculated (%): | 76.21 | 7.23 | 7.73 |
| Found (%): | 76.01 | 7.28 | 7.92 |

By method similar to that described in Example 480, there were obtained compounds of Examples 481–524 as follows:

EXAMPLE 481

5-[1-Oxo-3-(4-phenyl-1-piperazinyl)propyl]-3,4-dihydrocarbostyril

Colorless needle-like crystals (from ethanol-methanol)
Melting point: 180°–182° C.

EXAMPLE 482

5-{1-Oxo-3-[4-(2-ethoxyphenyl)-1-piperazinyl]propyl}-3,4-dihydrocarbostyril monohydrochloride White crystals (from methanol-water)

Melting point: 223°–235° C. (decomposed)

EXAMPLE 483

5-{1-Oxo-3-[4-(2-hydroxyphenyl)-1-piperazinyl]-propyl}-3,4-dihydrocarbostyril

EXAMPLE 484

5-{1-Oxo-3-[4-(4-n-butylphenyl)-1-piperazinyl]propyl}-3,4-dihydrocarbostyril

Colorless needle-like crystals (from ethanol-water)
Melting point: 218°–222° C. (decomposed)

EXAMPLE 485

5-{1-Oxo-3-[4-(2-chlorophenyl)-1-piperazinyl]propyl}-3,4-dihydrocarbostyril

EXAMPLE 486

5-{1-Oxo-3-[4-(2,3-dimethyl)-1-piperazinyl]propyl}-3,4-dihydrocarbostyril monohydrochloride White crystals (from methanol-water)
Melting point: 231°–234° C.

EXAMPLE 487

7-[1-Oxo-3-(4-phenyl-1-piperidyl)propyl]-3,4-dihydrocabostyril

Colorless needle-like crystals (from methanol)
Melting point: 171°–173° C.

EXAMPLE 488

7-{1-Oxo-3-[4-(4-methylphenyl)-1-piperidyl]propyl}-3,4-dihydrocarbostyril monohydrochloride White crystals (from ethanol-water)
Melting point: 212°–216° C. (decomposed)

EXAMPLE 489

7-{1-Oxo-3-[4-(4-fluorophenyl)-1-piperidyl]-propyl}-3,4-dihydrocarbostyril

EXAMPLE 490

7-{1-Oxo-3-[4-(2,4-dimethylphenyl)-1-piperidyl]-propyl}-3,4-dihydrocarbostyril monohydrochloride White crystals (from methanol-water)
Melting point: 226°–229° C.

5-[1-Oxo-2-(4-phenyl-1-piperazinyl)ethyl]-3,4-dihydrocarbostyril.

Colorless needle-like crystals (from methanol)
Melting point: 195°–198° C. (decomposed)

EXAMPLE 491

5-[1-Hydroxy-3-(4-phenyl-1-piperazynil)propyl]-3,4-dihydrocarbostyril

Colorless needle-like crystals (from ethanol)
Melting point: 158°–160° C.

EXAMPLE 492

7-[1-Hydroxy-3-(4-phenyl-1-piperidyl)propyl]-3,4-dihydrocarbostyril

Colorless prism-like crystals (from ethanol)
Melting point: 146°–149° C.

EXAMPLE 493

5-[3-(4-Phenyl-1-piperazinyl)propyl]-3,4-dihydrocarbostyril monohydrochloride

Colorless needle-like crystals (from ethanol-water)
Melting point: 230°–233° C.

EXAMPLE 494

7-[3-(4-Phenyl-1-piperidyl)propyl]-3,4-dihydrocarbostyril

Colorless needle-like crystal (from ethanol-water)
Melting point: 114°–118° C.

EXAMPLE 495

6-{1-Oxo-4-[4-(4-acetylphenyl)-1-piperzinyl]butyl}-3,4-dihydrocarbostyril

Yellow needle-like crystals (from dimethylformamide-water)
Melting point: 218°–219° C.

EXAMPLE 496

6-{1-Oxo-4-[4-(4-methylphenyl)-1-piperzinyl]butyl}-3,4-dihydrocarbostyril

Light yellow needle-like crystals (from ethanol)
Melting point: 187°–188° C.

EXAMPLE 497

6-{1-Oxo-4-[4-(4-carboxyphenyl)-1-piperazinyl]butyl}-3,4-dihydrocarbostyril monohyrochloride Colorless powdery crystals (from ethanol)
Melting point: 264°–265° C.

EXAMPLE 498

6-{1-Oxo-4-[4-(4-hydroxyphenyl)-1-piperazinyl]butyl}-3,4-dihydrocarbostyril

Colorless powdery crystals (from ethanol)
Melting point: 192°–194° C.

EXAMPLE 499

6-{1-Oxo-2-[4-(4-nitrophenyl)-1-piperazinyl]butyl}-3,4-dihydrocarbostyril

Yellow powdery crystals (from ethanol)
Melting point: 239°–241° C.

EXAMPLE 500

1-Benzyl-6-[1-hydroxy-3-(4-phenyl-1-piperazinyl)-propyl]-3,4-dihydrocarbostyril monooxalate Colorless needle-like crystals (from ethano-water)
Melting point: 161°–162° C.

EXAMPLE 501

6-[1-Oxo-4-(4-phenyl-1-piperazinyl)butyl-]3,4-dihydrfocarbostyril monohydrochloride Yellow powdery crystals
Melting point: 195°–196° C.

EXAMPLE 502

6-{1-Hydroxy-3-[4-(2,3-dimethylphenyl)-1-piperazinyl]propyl}-3,4-dihydrocarbostyril Colorless needle-like crystals (from ethanol)
Melting point: 173°–175° C. (decomposed)

Exmaple 503

6-{3-[4-(2-Ethoxyphenyl)-1-piperazinyl]-propyl}3,4-dihydrocarbostyril

Colorless prism-like crystals (from diethyl ether)
Melting point: 122°–123° C.

EXAMPLE 504

6-{4-[4-(2-Ethoxyphenyl)-1-piperzinyl]butyl}-3,4-dihydrocarbostyril

Colorless prism-like crystals (from isopropanol-diisopropyl ether)
Melting point: 131.5°–132.5° C.

EXAMPLE 505

6-{1-Oxo-4-[4-(3,4,5-trimethoxyphenyl)-1-piperazinyl]butyl}-3,4-dihydrocarbostyril dihydrochloride Colorless powdery crystals (from methanol water)
Melting point: 261°–263° C. (decomposed)

EXAMPLE 506

6-{1-Oxo-3-[4-(4-cyanophenyl)-1-piperzinyl]-propyl}-3,4-dihydrocarbostyril

Colorless plate-like crystals (from ethanol)
Melting point: 206°–207° C.

EXAMPLE 507

6-[1-Oxo-3-(4-benzyl-1-piperazinyl)propyl]-3,4-dihydrocarbostyril

Colorless needle-like crystals (from ethanol-water)
Melting point: 177°–178° C.

EXAMPLE 508

6-{1-Oxo-3-[4-(1-tetralinyl)-1-piperazinyl]propyl}-3,4-dihydrocarbostyril

Colorless prism-like crystals (from ethanol-water)
Melting point: 187°–188° C.

EXAMPLE 509

6-{1-Hydroxy-3-[4-(2-methoxyphenyl)-1-piperazinyl]propyl}-3,4-dihydrocarbostyril Colorless needle-like crystals (from isopropanol)
Melting point: 145°–147° C.

EXAMPLE 510

6-{1-Hydroxy-4-[4-(4-aminophenyl)-1-piperazinyl]butyl}-3,4-dihydrocarbostyril

Brown powdery crystals (from methanol)
Melting point: 243°–245° C.

EXAMPLE 511

1-Methyl-6-[1-oxo-3-(4-phenyl-1-piperazinyl)propyl]-3,4-dihydrocarbostyril monooxalate Corlorless flake-like crystals (from ethanol-water)
Melting point: 164°–165° C.

EXAMPLE 512

1-Allyl-6-[1-oxo-3-(4-phenyl-1-piperazinyl)propyl]-3,4-dihydrocarbostyril monooxalate Colorless flake-like crystals (from ethanol-water)
Melting point: 169°–170° C.

EXAMPLE 513

6-{4-[4-(3-Methylphenyl)-1-piperazinyl]butyl}-3,4-dihydrocarbostyril

Colorless flake-like crystals (from isopropanol-diisopropyl ether)
Melting point: 138.5°–139.5° C.

EXAMPLE 514

6-{1-Oxo-4-[4-(3,4-methylenedioxyphenyl)-1-piperazinyl]butyl}-3,4-dihydrocarbostyril monohydrochloride Colorless powdery crystals (from ethanol-water)
Melting point: 246°–248° C. (decomposed)

EXAMPLE 515

1-(2-Propynyl)-6-[1-oxo-3-(4-phenyl-1-piperidyl)-propyl]-3,4-dihydrocarbostyril monohydrochloride Colorless plate-like crystals (from ethanol-water)
Melting point: 203°–204° C. (decomposed)

EXAMPLE 516

6-[1-Oxo-3-(4-benzyl-1-piperidyl)propyl]-3,4-dihydrocarbostyril

Light-yellow plate-like crystals (from ethanol)
Melting point: 170°–171° C.

EXAMPLE 517

6-[1-Oxo-(4-phenyl-4-acetyl-1-piperidyl)butyl]-3,4-dihydrocarbostyril

Light yellow plate-like crystals (from ethanol)
Melting point: 166°–167° C.

EXAMPLE 518

6-{1-Oxo-3-[4-(2-benzimidazolinon-1-yl)-1-piperidyl]-propyl}-3,4-dihydrocarbostyril monohydrochloride Colorless plate-like crystals (from methanol-chloroform)
Melting point: 242°–243° C.

EXAMPLE 519

6-{1-Hydroxy-3-[4-(4-phenyl-4-hydroxy)-1-piperidyl]-propyl}-3,4-dihydrocarbostyril Colorless needle-like crystals (from ethanol)
Melting point: 102°–103° C.

EXAMPLE 520

6-[3-(4-Phenyl-1-piperidyl)propyl]-3,4-dihydrocarbostyril monohydrochloride

Colorless plate-like crystals (from methanol)
Melting point: 232°–233° C.

EXAMPLE 521

6-[3-(4-Benzyl-1-piperidyl)propyl]-3,4-dihydrocarbostyril

Colorless plate-like crystals (from ethanol)
Melting point: 99°–100° C.

EXAMPLE 522

6-{3-[4-(4-Methylphenyl)-1-piperidyl]propyl}-3,4-dihydrocarbostyril

Colorless plate-like crystals (from isopropanol-n-hexane)
Melting point: 125°–126° C.

EXAMPLE 523

5-[3-(4-Phenyl-1-piperidyl)propyl]-3,4-dihydrocarbostyril

EXAMPLE 524

6-{3-[4-(2-Methoxyphenyl)-1-piperidyl]-propyl}-3,4-dihydrocarbostyril monooxalate Colorless flake-like crystals (from ethanol-water)
Melting point: 178°-181° C.

EXAMPLE 525

4-(2,3-Dimethylphenyl)piperazine hydrochloride (0.2 mol) and 37%-formalin aqueous solution (0.2 mol) were mixed and to this mixture was added acetic anhydride (10 times amount by weight) at 80°-90° C. The reaction mixture was kepy at 50°-90° C. for 1 hour, then 5-acetyl-3,4-dihydrocarbostyril (0.1 mol was added thereto and stirred at 80° to 90° C. for 1 hour. After the reaction was completed an excess amount of acetone was added to the reaction mixture and crystals precipitated were collected by filtration. The crystals were dissolved in methanol and then neutralized by adding 1N-NaOH aqueous solution and allowed to stand. The crystals precipitated were collected by filtration, treated with concentrated hydrochloric acid and methanol to form monohydrochloride and recrystallized from ethanol-water to obtain 5{1-oxo-3-[4-(2,3-dimethylphenyl)-1-piperazinyl]propyl}-3,4-dihydrocarbostyril monohydrochloride. Yield: 35%. White crystals. Melting point: 231°-234° C.

EXAMPLE 526

By a procedure similar to that used in Example 525, by using paraformaldehyde (0.2 mol) in place of 37%-formalin aqueous solution, there was obtained 5-{1-oxo-3-[4-(2,3-dimethylphenyl)-1-piperazinyl]propyl}-3,4-dihydrocarbostyril monohydrochloride. Yield: 34%. White crystals. Melting point: 231°-234° C.

EXAMPLE 527

By a procedure similar to that used in Example 525, by using trioxane (0.2 mol) in place of 37%-formalin aqueous solution, there was obtained 5-{1-oxo-3-[4-(2,3-dimethylphenyl)-1-piperazinyl]propyl}-3,4-dihydrocarbostyril monohydrochloride.
Yield: 39%. White crystals.
Melting point: 231°-234° C.

By a procedure similar to that used in Example 525, there were obtained compounds of Examples 528–564 as follows:

EXAMPLE 528

5-{1-Oxo-3-[4-(2-ethoxyphenyl)-1-piperazinyl]-propyl}-3,4-dihydrocarbostyril monohydrochloride White crystals (from methanol-water)
Melting point: 223°-235° C. (decomposed)

EXAMPLE 529

5-{1-Oxo-3-[4-(2-chlorophenyl)-1-piperazinyl]-propyl}-3,4-dihydrocarbostyril

EXAMPLE 530

5-{1-Oxo-3-[4-(2-hydroxyphenyl)-1-piperazinyl]-propyl}-3,4-dihydrocarbostyril

EXAMPLE 531

7-{1-Oxo-3-[4-(4-methylphenyl)-1-piperidyl]propyl}-3,4-dihydrocarbostyril monohydrochloride White crystals (from ethanol-water)
Melting point: 212°-216° C.

EXAMPLE 532

7-{1-Oxo-3-[4-(4-fluorophenyl)-1-piperidyl]propyl}-3,4-dihydrocarbostyril

EXAMPLE 533

7-{1-Oxo-3-[4-(2,4-dimethylphenyl)-1-piperidyl]-propyl}-3,4-dihydrocarbostyril monohydrochloride White crystals (from ethanol-water)
Melting point: 226°-229° C.

EXAMPLE 534

6-[1-Oxo-3-(4-phenyl-1-piperazinyl)propyl]-3,4-dihydrocarbostyril

Colorless flake-like crystals
Melting point: 196°-197° C.

EXAMPLE 535

6-{1-Oxo-3-[4-(2,3-dimethylphenyl)-1-piperazinyl]-propyl}-3,4-dihydrocarbostyril monohydrochloride Colorless needle-like crystals
Melting point: 273°-274° C.

EXAMPLE 536

5-[1-Oxo-3-(4-phenyl-1-piperazinyl)propyl]-3,4-dihydrocarbostyril

Colorless needle-like crystals (from ethanol-methanol)
Melting point: 180°-182° C.

EXAMPLE 537

6-[1-Oxo-3-(4-benzyl-1-piperazinyl)propyl]-3,4-dihydrocarbostyril

EXAMPLE 538

6-{1-Oxo-3-[4-(1-tetralinyl)-1-piperazinyl]propyl}-3,4-dihydrocarbostyril

Colorless prism-like crystals (from ethanol-water)
Melting point: 187°-188° C.

EXAMPLE 539

1-Methyl-6-[1-oxo-3-(4-phenyl-1-piperazinyl)propyl]-3,4-dihydrocarbostyril monooxalate Colorless flake-like crystals (from ethanol-water)
Melting point: 164°-165° C.

EXAMPLE 540

6-{1-Oxo-3-[4-(3-chlorophenyl)-1-piperazinyl]propyl}-3,4-dihydrocarbostyril monohydrochloride monohydrate Colorless needle-like crystals (from ethanol-water)

Melting point: 233°–234° C. (decomposed)

EXAMPLE 541

6-{1-Oxo-3-[4-(4-methylphenyl)-1-piperazinyl]propyl}-3,4-dihydrocarbostyril monohydrochloride Light- yellow needle-like crystals (from ethanol-water)
Melting point: 224°–226° C.

EXAMPLE 542

6-{1-Oxo-3-[4-(2-fluorophenyl)-1-piperazinyl]propyl}-3,4-dihydrocarbostyril

Colorless powdery crystals (from dimethylformamide-water)
Melting point: 200°–201° C.

EXAMPLE 543

6-{1-Oxo-2-[4-(3-chlorophenyl)-1-piperazinyl]butyl} carbostyril monohydrochloride Colorless needle-like crystals (from isopropanol)
Melting point: 209°–210° C. (decomposed)

EXAMPLE 544

6-{1-Oxo-2-[4-(3-chlorophenyl)-1-piperazinyl]butyl}-3,4-dihydrocarbostyril monooxalate Colorless needle-like crystals (from isopropanol)
Melting point: 135°–136° C.

EXAMPLE 545

6-{1-Oxo-3-[4-(4-cyanophenyl)-1-piperazinyl]propyl}-3,4-dihydrocarbostyril

Colorless plate-like crystals (from ethanol)
Melting point: 206°–207° C.

EXAMPLE 546

6-{1-Oxo-3-[4-(2-methoxyphenyl)-1-piperazinyl]propyl}-3,4-dihydrocarbostyril monohydrochloride Light yellow needle-like crystals (from dioxane-water)
Melting point: 212.5°–213° C.

EXAMPLE 547

1-Ally-6-[1-oxo-3-(4-phenyl-1-piperazinyl)propyl]-3,4-dihydrocarbostyril monooxalate Colorless flake-like crystals (from ethanol-water)
Melting point: 169°–170° C.

EXAMPLE 548

1-Benzyl-6-[1-oxo-3-(4-phenyl-1-piperazinyl)propyl]-3,4-dihydrocarbostyril monooxalate Colorless needle-like crystals (from ethanol-water)
Melting point: 171°–172° C.

EXAMPLE 549

6-[1-Oxo-3-(4-benzyl-1-piperidyl)propyl]-3,4-dihydrocarbostyril

Light yellow plate-like crystals (from ethanol)
Melting point: 170°–171° C.

EXAMPLE 550

6-[1-Oxo-3-(4-phenyl-1,2,5,6-tetrahydro-1-pyridyl)-propyl]-3,4-dihydrocarbostyril Light yellow plate-like crystals (from ethanol)
Melting point: 167°–168° C.

EXAMPLE 551

6-[1-Oxo-3-(4-phenyl-1-piperidyl)propyl]-3,4-dihydrocarbostyril

Colorless needle-like crystals (from ethanol)
Melting point: 183°–184° C.

EXAMPLE 552

6-[1-Oxo-3-(4-phenyl-4-hydroxy-1-piperidyl)propyl]-3,4-dihydrocarbostyril

Colorless needle-like crystals (from ethanol-ethyl acetate)
Melting point: 205°–206° C.

EXAMPLE 553

6-{1-Oxo-3-[4-(2-benzimidazolinon-1-yl)-1-piperidyl]-propyl}-3,4-dihydrocarbostyril monohydrochloride Colorless plate-like crystals (from methanol-chloroform)
Melting point: 242°–243° C.

EXAMPLE 554

1-Isopentyl-6-[1-oxo-3-(4-phenyl-1-piperidyl)propyl]-3,4-dihydrocarbostyril monohydrochloride Colorless mica-like crystals (from ethanol-water)
Melting point: 205°–206° C.

EXAMPLE 555

1-Allyl-6-[1-oxo-3-(4-phenyl-1-piperidyl)propyl]-3,4-dihydrocarbostyril monohydrochloride Colorless plate-like crystals (from ethanol-water)
Melting point: 198°–199° C. (decomposed)

EXAMPLE 556

1-(2-Propynyl)-6-[1-oxo-3-(4-phenyl-1-piperidyl)-propyl]-3,4-dihydrocarbostyril monohydrochloride Colorless plate-like crystals (from ethanol-water)
Melting point: 203°–204° C. (decomposed)

EXAMPLE 557

1-(3-Phenylpropyl)-6-[1-oxo-3-(4-phenyl-1-piperidyl)-propyl]-3,4-dihydrocarbostyril monohydrochloride Colorless powdery crystals (from isopropanol)
Melting point: 164°–165° C.

EXAMPLE 558

1-Methyl-6-[1-oxo-3-(4-phenyl-1-piperidyl)propyl]-3,4-dihydrocarbostyril monohydrochloride Light yellow plate-like crystals (from ethanol-water)
Melting point: 213°–214° C. (decomposed)

EXAMPLE 559

6-{1-Oxo-3-[4-(4-chlorophenyl)-1,2,5,6-tetrahydro-1-pyridyl]propyl}-3,4-dihydrocarbostyril ½hydrate Light yellow flake-like crystals (from ethanol)
Melting point: 170°–171° C.

EXAMPLE 560

6-{1-Oxo-3-[4-(4-methylphenyl)-1,2,5,6-tetrahydro-1-pyridyl]propyl}-3,4-dihydrocarbostyril Light yellow mica-like crystals (from methanol-water)
Melting point: 189°–190° C.

EXAMPLE 561

6-{1-Oxo-3-[4-(4-fluorophenyl)-1,2,5,6-tetrahydro-1-pyridyl]propyl}-3,4-dihydrocarbostyril Light yellow plate-like crystals (from ethanol-water)
Melting point: 181°–182° C.

EXAMPLE 562

6-{1-Oxo-3-[4-(3-methylphenyl)-1,2,5,6-tetrahydro-1-pyridyl]propyl}-3,4-dihydrocarbostyril Light yellow plate-like crystals (from ethanol-water
Melting point: 152°–153° C.

EXAMPLE 563

6-{1-Oxo-3-[4-(3,5-dimethoxyphenyl)-1,2,5,6-tetrahydro-1-pyridyl]propyl}-3,4-dihydrocarbostyril

EXAMPLE 564

6-{1-Oxo-3-[4-(3-methoxyphenyl)-1,2,5,6-tetrahydro-1-pyridyl]propyl}-3,4-dihydrocarbostyril Light yellow needle-like crystals (from ethanol-water)
Melting point: 155°–156° C.

What is claimed is:

1. A carbostyril derivative or a pharmaceutically acceptable salt thereof, wherein said carbostyril derivative is represented by thereof, wherein said carbostyril derivative is represented by the general formula (1),

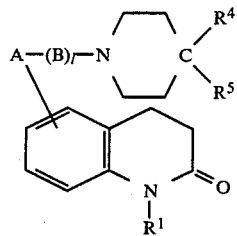  (1)

wherein $R^1$ is a hydrogen atom, a lower alkyl group, a phenyl-lower alkyl group, a lower alkenyl group or a lower alkynyl group; A is a group of the formula,

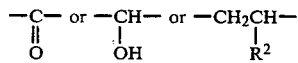

(wherein $R^2$ is a hydrogen atom or a lower alkyl group); B is a lower alkylene group; l is 1 when A is a group of the formula

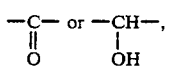

or l is 0 or 1 when A is a group of the formula

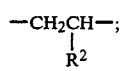

$R^4$ is an unsubstituted or substituted-phenyl group having 1 to 3 substituents, on the phenyl ring, selected from the group consisting of a halogen atom, a lower alkyl group and a lower alkoxy group; or $R^4$ is a substituted-phenyl group having a lower alkylene-dioxy group as the substituent, on the phenyl ring, a phenyl-lower alkyl group, 1,2,3,4-tetrahydronaphthyl group or a group of the formula,

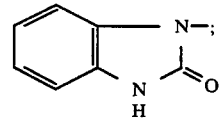

$R^5$ is a hydrogen atom, a hydroxy group or a lower alkanoyl group; the carbon-carbon bond between the 3- and 4-positions in the piperidine ring of formula (1) may be a double bond, in which case $R^5$ does not exist; the carbon-carbon bond between the 3- and 4-positions in the carbostyril skeleton is a single or double bond; provided that (a) when $R^1$ is a hydrogen atom, (b) when the substituted position of a group of the formula

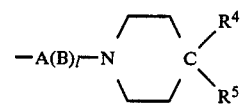

is at the 6-position in the carbostyril skeleton (A is a group of the formula

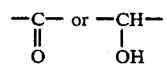

B is a group of the formula

(wherein R is a hydrogen atom or a lower-alkyl group); $R^4$ is a phenyl-lower alkyl group or an unsubstituted phenyl group) and (c) when the carbon-carbon bond between the 3- and 4-positions in the carbostyril skeleton is a single bond, then $R^5$ should not be a hydrogen atom.

2. The carbostyril derivatives and salts thereof according to claim 1, wherein $R^4$ is an unsubstituted-or substituted-phenyl group having 1 to 3 substituents, on the phenyl ring, selected from the group consisting of a halogen atom, a lower alkyl group and a lower alkoxy group.

3. The carbostyril derivatives and salts thereof according to claim 1, wherein $R^4$ is a substituted-phenyl group having a lower alkylenedioxy group as the substituent, on the phenyl ring, or 1,2,3,4-tetrahydronaphthyl group.

4. The carbostyril derivatives and salts thereof according to claim 1, wherein $R^4$ is a phenyl-lower alkyl group.

5. The carbostyril derivatives and salts thereof according to claim 1, wherein $R^1$ is a hydrogen atom.

6. The carbostyril derivatives and salts thereof according to claim 1, wherein $R^1$ is a lower alkyl group, a phenyl-lower alkyl group, a lower alkenyl group, or a lower alkynyl group.

7. The carbostyril derivative or pharmaceutically acceptable salt thereof according to any one of claims 1 to 4, wherein the carbon-carbon bond between the 3- and 4-positions in the carbostyril skeleton is a single bond.

8. The carbostyril derivative or pharmaceutically acceptable salt thereof according to claim 7, wherein B is ethylene, trimethylene, 2-methyltrimethylene, 2,2-dimethyltrimethylene, 1-methyltrimethylene, tetramethylene, pentamethylene or hexamethylene.

9. The carbostyril derivative or pharmaceutically acceptable salt thereof according to claim 8, wherein the substituted position of the group of the formula

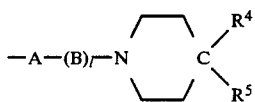

is the 6-position in the carbostyril skeleton.

10. The carbostyril derivative or pharmaceutically acceptable salt thereof according to claim 9, wherein B is trimethylene or tetramethylene.

11. The carbostyril derivative or pharmaceutically acceptable salt thereof according to claim 10, wherein $R^1$ is a hydrogen atom.

12. The carbostyril derivative or pharmaceutically acceptable salt thereof according to claim 10, wherein $R^1$ is a lower alkyl, a phenyl-lower alkyl, a lower alkenyl or a lower alkynyl group.

13. The carbostyril derivative or pharmaceutically acceptable salt thereof according to any one of claims 1 to 4, wherein the carbon-carbon bond between the 3- and 4-positions in the carbostyril skeleton is a double bond.

14. The carbostyril derivative or pharmaceutically acceptable salt thereof according to claim 13, wherein B is ethylene, trimethylene, 2-methyltrimethylene, 2,2-dimethyltrimethylene, 1-methyltrimethylene, tetramethylene, pentamethylene or hexamethylene.

15. The carbostyril derivative or pharmaceutically acceptible salt thereof according to claim 14, wherein the substituted position of the group of the formula

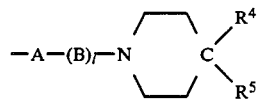

is the 6-position in the carbostyril skeleton.

16. The carbostyril derivative or pharmaceutically acceptable salt thereof according to claim 15, wherein B is ethylene, trimethylene or tetramethylene.

17. The carbostyril derivative or pharmaceutically acceptable salt thereof according to any one of claims 1 to 4, wherein the substituted position of the group of the formula

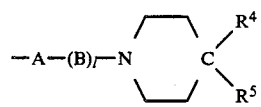

is the 6-position in the carbostyril skeleton and the carbon-carbon bond between the 3- and 4-positions in the carbostyril skeleton is a single bond.

18. The carbostyril derivative or pharmaceutically acceptable salt thereof according to any one of claims 1 to 4, wherein the substituted position of the group of the formula is the 6-position in the carbostyril skeleton and the carbon-carbon bond between the 3- and 4-positions in the carbostyril skeleton is a double bond.

19. 6-[1-Oxo-3-(4-phenyl-1,2,5,6-tetrahydro-1-pyridyl)propyl]-3,4-dihydrocarbostyril.

20. 6-{1-Oxo-3-[4-(4-chlorophenyl)-1,2,5,6-tetrahydro-1-pyridyl]propyl}-3,4-dihydrocarbostyril ¼-hydrate.

21. A pharmaceutical composition comprising an antihistaminic agent containing an effective amount of at least one carbostyril derivative represented by the general formula (1) of claim 1, or a pharmaceutically acceptable salt thereof, as the active ingredient.

* * * * *

UNITED STATES PATENT AND TRADEMARK OFFICE
CERTIFICATE OF CORRECTION

PATENT NO. : 4,567,187          Page 1 of 2

DATED      : January 28, 1986

INVENTOR(S) :
          Kazuo BANNO et al.

It is certified that error appears in the above-identified patent and that said Letters Patent is hereby corrected as shown below:

Claim 1, column 129, lines 28-29, delete "by thereof, wherein said carbostyril derivative is represented";

lines 35-40, correct the lower portion of formula (1) to appear as follows:

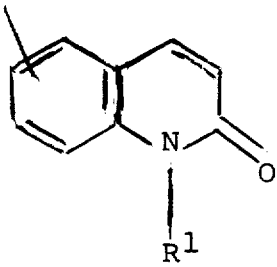

and

--$l$ is 0 or 1--.

line 51, change "1 is 1" to --$l$ is 1--;

line 57, change "1 is 0 or 1" to

UNITED STATES PATENT AND TRADEMARK OFFICE
CERTIFICATE OF CORRECTION

PATENT NO. : 4,567,187

DATED : January 28, 1986

INVENTOR(S) : Kazuo BANNO et al.

It is certified that error appears in the above-identified patent and that said Letters Patent is hereby corrected as shown below:

Please note that in the changes to lines 51 and 57, the handwritten symbol " $\downarrow$ " is intended to be the printed symbol which immediately follows (B) in formula (1) in claim 1 at column 129, approximately line 32.

Signed and Sealed this

Eighth Day of September, 1987

Attest:

DONALD J. QUIGG

*Attesting Officer*      *Commissioner of Patents and Trademarks*